(12) United States Patent
Pavlakis et al.

(10) Patent No.: US 6,794,498 B2
(45) Date of Patent: *Sep. 21, 2004

(54) METHOD OF ELIMINATING INHIBITORY/INSTABILITY REGIONS OF MRNA

(75) Inventors: George N. Pavlakis, Rockville, MD (US); Barbara K. Felber, Rockville, MD (US)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 0 days.

This patent is subject to a terminal disclaimer.

(21) Appl. No.: 09/943,722

(22) Filed: Aug. 31, 2001

(65) Prior Publication Data

US 2002/0192660 A1 Dec. 19, 2002

Related U.S. Application Data

(63) Continuation of application No. 09/678,437, filed on Oct. 2, 2000, now Pat. No. 6,414,132, which is a continuation of application No. 09/414,117, filed on Oct. 8, 1999, now Pat. No. 6,291,664, which is a continuation of application No. 08/850,049, filed on May 2, 1997, now Pat. No. 5,965,726, which is a continuation of application No. 08/050,478, filed as application No. PCT/US93/02908 on Mar. 29, 1993, now Pat. No. 5,972,596, which is a continuation-in-part of application No. 07/858,747, filed on Mar. 27, 1992, now Pat. No. 6,174,666.

(51) Int. Cl.[7] ............ C07H 19/00; C07H 21/00; C07H 21/02; C07H 21/04; C12Q 1/68

(52) U.S. Cl. ............ 536/22.1; 435/5; 435/6; 435/41; 435/7.1; 435/69.1; 435/91.1; 435/70.3; 435/91.2; 536/23.1; 536/24.3; 536/24.31; 536/24.32; 536/24.33

(58) Field of Search ............ 435/5, 6, 41, 7.1, 435/69.1, 91.1, 70.3, 91.2; 536/22.1, 23.1, 24.3–33

(56) References Cited

U.S. PATENT DOCUMENTS 4,652,639 A 3/1987 Stabinsky .......... 536/27

(List continued on next page.)

FOREIGN PATENT DOCUMENTS

| EP | 0 335 635 | 10/1989 |
| EP | 0 345 242 A2 | 12/1989 |
| WO | WO 90/11092 | 10/1990 |

OTHER PUBLICATIONS

B.A. Bunnell et al., "A Dominant Negative Mutation in Two Proteins Created by Ectopic Expression of an Au–Rich 3' Untranslated Region", Somataic Cell and Mol. Genet. 16:151–162 (1990).

(List continued on next page.)

*Primary Examiner*—Jeffrey Siew
(74) *Attorney, Agent, or Firm*—Townsend and Townsend and Crew

(57) ABSTRACT

A method of locating an inhibitory/instability sequence or sequences within the coding region of an mRNA and modifying the gene encoding that mRNA to remove these inhibitory/instability sequences by making clustered nucleotide substitutions without altering the coding capacity of the gene is disclosed. Constructs containing these mutated genes and host cells containing these constructs are also disclosed. The method and constructs are exemplified by the mutation of a Human Immunodeficiency Virus-1 Rev-dependent gag gene to a Rev-independent gag gene. Constructs useful in locating inhibitory/instability sequences within either the coding region or the 3' untranslated region of an mRNA are also disclosed. The exemplified constructs of the invention may also be useful in HIV-1 immunotherapy and immunoprophylaxis.

4 Claims, 18 Drawing Sheets

U.S. PATENT DOCUMENTS

Figure 1A:
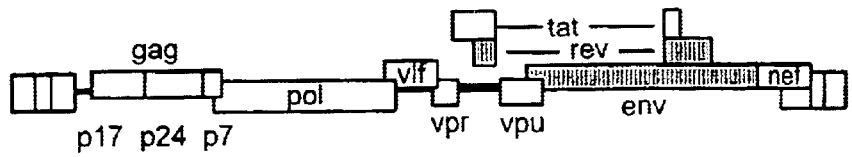

| | | | | |
|---|---|---|---|---|
| 4,959,455 | A | * 9/1990 | Clark et al. | 530/351 |
| RE33,653 | E | 7/1991 | Mark et al. | 424/85.1 |
| 5,073,627 | A | 12/1991 | Curtis et al. | 530/351 |
| 5,082,767 | A | 1/1992 | Hatfield et al. | 435/6 |
| 5,965,726 | A | * 10/1999 | Pavlakis et al. | 536/23.72 |
| 5,972,596 | A | * 10/1999 | Pavlakis et al. | 435/5 |
| 6,174,666 | B1 | * 1/2001 | Pavlakis et al. | 435/5 |
| 6,291,664 | B1 | * 9/2001 | Pavlakis et al. | 536/23.72 |
| 6,414,132 | B1 | * 7/2002 | Pavlakis et al. | 536/23.7 |

OTHER PUBLICATIONS

D. Caput et al., "Identification of a common nucleotide sequence in the 3'–untranslated region of mRNA molecules specifying inflammatory mediators", Proc. Natl. Acad. Sci. 83:1670–1674 (1986).

P. Carter–Muenchau and R. Wolf, "Growth–rate–dependent regulation of 6–phosphogluconate dehydrogenase level mediated by an anti–Shine–Dalgarno sequence located within the *Escherichia coli gnd* structural gene", Proc. Natl. Acad. Sci., USA, 86:1138–1142 (1989).

A.W. Cochrane et al., "Identification and Characterization of Intragenic Sequences Which Repress Human Immunodeficiency Virus Structural Gene Expression", J. Virol. 65:5305–5313 (1991).

M.D. Cole and S.E. Mango, cis–Acting Determinants of c–*myc* mRNA Stability, Enzyme 44:167–180 (1990).

M.D. Edge et al., "Total synthesis of a human leukocyte interferon gene", Nature 292:756–762 (1981).

M. Emerman, "The *rev* Gene Product of the Human Immunodeficiency Virus Affects Envelope–Specific RNA Localization", Cell 57:1155–1165 (1989).

B. Felber et al., "rev protein of human immunodeficiency virus type 1 affects the stability and transport of the viral mRNA", Proc. Natl. Acad. Sci. USA 86:1495–1499 (1989).

M. Hadzopoulou–Cladaras et al., "The *rev* (*trs/art*) Protein of Human Immunodeficiency Virus Type 1 Affects Viral mRNA and Protein Expression via a cis–Acting Sequence in the *env* Region", J. Virol. 63:1265–1274 (1989).

M.W. Hentze, "Determinants and regulation of cytoplasmic mRNA stability in eukaryotic cells", Biochem. Biophys. Acta 1090: 281–292 (1991).

E. Jay et al., "Chemical Synthesis of a Biologically Active Gene for Human Immune Interferon–γ", J. Biol. Chem. 259:6311–6317 (1984).

T. R. Jones and M.D. Cole, "Rapid Cytoplasmic Turnover of c–*myc* mRNA: Requirement of the 3' Untranslated Sequences", Mol. Cell Biol. 7:4513–4521 (1987).

R. Kamen et al., "A Novel Mechanism of Post Transcriptional, Sequence–Specific Regulation of mRNA Stability", J. Cell Bio. Suppl. 10D (1986):152 (Abst. No. 0210).

D.M. Koeller et al., "Translation and the stability of mRNAs encoding the transferrin receptor and c–*fos*", Proc. Natl. Acad. Sci. USA, 88:7778–7782 (1991).

V. Kruys et al., "Constitutive activity of the tumor necrosis factor promoter is canceled by the 3' untranslated region in nonmacrophage cell lines; a trans–dominant factor overcomes this suppressive effect", Proc. Natl. Acad. Sci. USA, 89:673–677 (1992).

T.A. Kunkel, "Rapid and efficient site–specific mutagenesis without phenotypic selection", Proc. Natl. Acad. Sci. USA, 82:488–492 (1985).

I.A. Laird–Offringa et al., "Rapid c–*myc* mRNA degradation does not require (A+U)–rich sequences or complete translation of the mRNA", Nucleic Acids Res. 19:2387–2394 (1991).

M.D. Lundigran et al., "Transcribed sequences of the *Escherichia coli btuB* gene control its expression and regulation by vitamin $B_{12}$", Proc. Natl. Acad. Sci. USA, 88:1479–1483 (1991).

F. Maldarelli et al., "Identification of Posttranscriptionally Active Inhibitory Sequences in Human Immunodeficiency Virus Type 1 RNA: Novel Level of Gene Regulation", J. Virol. 65:5732–5743 (1991).

K.P. Nambiar et al., "Total synthesis and Cloning of a Gene Coding for the Ribonuclease S Protein", Science 223:1299–1301 (1984).

R. Parker and A. Jacobson, "Translation and a 42–nucleotide segment within the coding region of the mRNA encoded by the *MATα1* gene are involved in promoting rapid mRNA decay in yeast", Proc. Natl. Acad. Sci. USA, 87:2780–2784 (1990).

C.A. Rosen, "Intragenic cis–acting *art* gene–responsive sequences of the human immunodeficiency virus", Proc. Natl. Acad. Sci., USA, 85:2071–2075 (1988).

S. Schwartz et al., "Distinct RNA Sequences in the *gag* region of Human Immunodeficiency Virus Type 1 Decrease RNA Stability and Inhibit Expression in the Absence of Rev Protein", J. Virol. 66:150–159 (1992).

G. Shaw and R. Kamen, "A Conserved AU Sequence from the 3' Untranslated Region of GM–CSF mRNA Mediates Selective mRNA Degradation", Cell 46:659–667 (1986).

G. Shaw and R. Kamen, "A Conserved AU Sequence from the 3' Untranslated Region of GM–CSF mRNA Mediates Selective mRNA Degradation", J. Cell. Bio. Suppl. 11C (1987):132 (Abst. No. L541).

A.–B. Shyu et al., "Two distinct destabilizing elements in the c–*fos* message trigger deadenylation as a first step in rapid mRNA decay", Gen. & Devel. 5:221–231 (1991).

C.M. Stoltzfus and S.J. Fogarty, "Multiple Regions in the Rous Sarcoma Virus *src* Gene Intron Act in *cis* To Affect the Accumulation of Unspliced RNA", J. Virol. 63:1669–1676 (1989).

T. Wilson and R. Treisman, "Removal of poly(A) and consequent degradation of c–*fos* mRNA facilitated by 3' AU–rich sequences", Nature 336:396–399 (1988).

R. Wisdom and W. Lee, "The protein–coding region of c–*myc* mRNA contains a sequence that specifies rapid mRNA turnover and induction by protein synthesis inhibitors", Gen. & Devel. 5:232–243 (1991).

D.H. Wreschner and G. Rechavi, "Differential mRNA stability to reticulocyte ribonucleases correlates with 3' non-coding $(U)_nA$ sequences", Eur. J. Biochem. 172:333–340 (1988).

Schwartz et al., "Mutational Inactivation of an Inhibitory Sequence in HIV–1 Results in Rev–independent *gag* Expression", Journal of Virology, vol. 66, 12:7176–7182 (1992) (Published after filing date of 07/858,747 priority application.).

Copy of PCT Search Report.

Albert B Sabin, "Improbability of effective vaccination against human immunodeficiency virus because of its intracellular transmission and rectal portal of entry", Proc. Natl. Acad. Sci. USA, 89:8852–8855 (Sep. 1992) (See whole document, especially abstract and right column of p. 8854) ("Reference 1").

Saladin Osmanov et al., "HIV–1 Genetic Variability: Implications for the Development of HIV Vaccines", Antibiotics and Chemotherapy, 48:30–38 (1996) (See whole document, especially pp. 35–36) ("Reference 2").

Kavita S. Lole, et al., "Full–Length Human Immunodeficiency Virus Type 1 Genomes from Subtype C–Infected Seroconverters in India, with Evidence of Intersubtype Recombination", Journal of Virology, 73:152–160 (Jan. 1999) (See whole document, especially abstract) ("Reference 3").

"Nikkei Biotechnology Annual Report '98", Nikkei Biotech, (Nov. 30, 1997), Nikkei Business Publications, Inc., p. 214 (English translation of table on p. 214, lines 30–35 entitled "The recent stream of research and development on AIDS") ("Reference 4").

"Nikkei Biotechnology Annual Report '97", Ed. Nikkei Biotech, (Nov. 30, 1996), Nikkei Business Publications, Inc., p. 246 (English translation of a table on p. 246, lines 43–46 entitled "The recent stream of biotechnological research on AIDS") ("Reference 6").

"Nikkei Biotechnology Annual Report '99", Ed. Nikkei Biotech, (Nov. 30, 1998), Nikkei Business Publications, Inc., p. 79 (English translation of table on p. 79, lines 14–17 entitled "The main stream of research and development on AIDS") ("Reference 7").

R.I. Connor, et al., "Immunological and Virological Analyses of Persons Infected by Human Immunodeficiency Virus Type 1 while Participating in Trials of Recombinant gp120 Subunit Vaccines", Journal of Virology, 72:1552–1576 (Feb. 1998) (See whole document, especially abstract) ("Reference 5").

K.–C. Chou, et al., "Diagrammatization of Codon Usge in 339 Human Immunodeficiency Virus Proteins and Its Biological Implication", AIDS Research and Human Retroviruses, 8:1967–1976 (1992).

J. Cohen, et al., (abstract) "Expression of the HIV–1 env (gp160) in the yeast *Saccaromyces cerevisiae* via expression/secretion vectors and partial characterization of the gene product", in Modern Approaches New Vaccines, 64 (1988).

B. Coulombe, et al., "Expression of a synthetic human interferon–$\alpha_1$ gene with modified nucleotide sequence in mammalian cells", Gene, 46:89–95 (1986).

D. M. D'Agostino, et al., "The Rev Protein of Human Immunodeficiency Virus Type 1 Promotes Polysomal Association and Translation of *gag/pol* and *vpu/env* mRNAs", Molecular and Cellular Biology, 12:1375–1386 (1992).

M.B. Feinberg, et al., "HTLV–III Expression and Production Involve Complex Regulation at the Levels of Splicing and Translation of Viral RNA", Cell, 46:807–817 (1986).

E. Fortkamp, et al., "Cloning and Expression in *Escherichia coli* of a Synthetic DNA for Hirudin, the Blood Coagulation Inhibitor in the Leech", DNA, 5:511–517 (1986).

Grantham et al., "AIDS virus and HTLV–I differ in codon choices", Nature 319:727–728 (1986).

M.–L. Hammarskjöld, et al., "Regulation of Human Immunodeficiency Virus *env* Expression by the *rev* Gene Product," Journal of Virology, 63:1959–1966 (1989).

R.A. Hernan, et al., "Human Hemoglobin Expression in *Escherichia coli*: Importance of Optimal Codon Usage", Biochemistry 31:8619–8628 (1992).

H. Kamiya, et al., "Transformation of NIH3T3 Cells with Synthetic c–Ha–*ras* Genes", Jpn. J. Cancer Res. 80:200–203 (1989).

J. Kypr, et al., "Unusual codon usage of HIV", Nature 327:20 (1987).

J.R. McCarrey, "Molecular evolution of the human Pgk–2 retroposon", Nucleic Acids Res. 18:949–955 (1990).

T. Nakamura, et al., "Two types of linkage between codon usage and gene–expression levels", FEBS Letters 289:123–125 (1991).

C.B. Newgard, et al., "Sequence analysis of the cDNA encoding human liver glycogen phosphorylase reveals tissue–specific codon usage", Proc. Natl. Acad. Sci. USA 83:8132–8136 (1986).

S.H. Rangwala, et al., "High–level production of active HIV–1 protease in *Escherichia coli*", Gene 122:263–269 (1992).

M. Robinson, et al., "Codon usage can affect efficiency of translation of genes in *Escherichia coli*", Nucleic Acids Research 12:6663–6671 (1984).

C.A. Scorer, et al., "The intracellular production and secretion of HIV–1 envelope protein in the methylotrophic yeast *Pichia pastoris*", Gene 136:111–119 (1993).

R. Seetharam, et al., "Mistranslation in IGF–1 During Over-Expression of the Protein in *Escherichia coli* Using a Synthetic Gene Containing Low Frequency Codons," Biochem. Biophys. Res. Comm. 155:518–523 (1988).

P.M. Sharp, "What can AIDS virus codon usage tell us ?", Nature 324:114 (1986).

P.M. Sharp, et al., "Codon usage pataterns in *Escherichia coli, Bacillus subtilis, Saccharomyces cerevisiae, Schizosaccharomyces pombe, Drosophila melanogaster* and *Homo sapiens*; a review of the considerable within–species diversity", Nucleic Acids Res. 16:8207–8211 (1988).

F.J. van Hemert, et al., "The Tendency of Lentiviral Open Reading Frames to Become A–Rich: Constraints Imposed by Viral Genome Organization and Cellular tRNA Availability", Journal of Molecular Evolution, 41:132–140 (1995).

D.P. Williams, et al., "Design, synthesis and expression of a human interleukin–2 gene incorporating the codon usage bias found in highly expressed *Escherichia coli* genes", Nucleic Acids Research 16:10453–10467 (1988).

S. Zhang, et al., "Low–usage condons in *Escherichia coli*, yeast, fruit fly and primates", Gene, 105:61–72 (1991).

\* cited by examiner

A
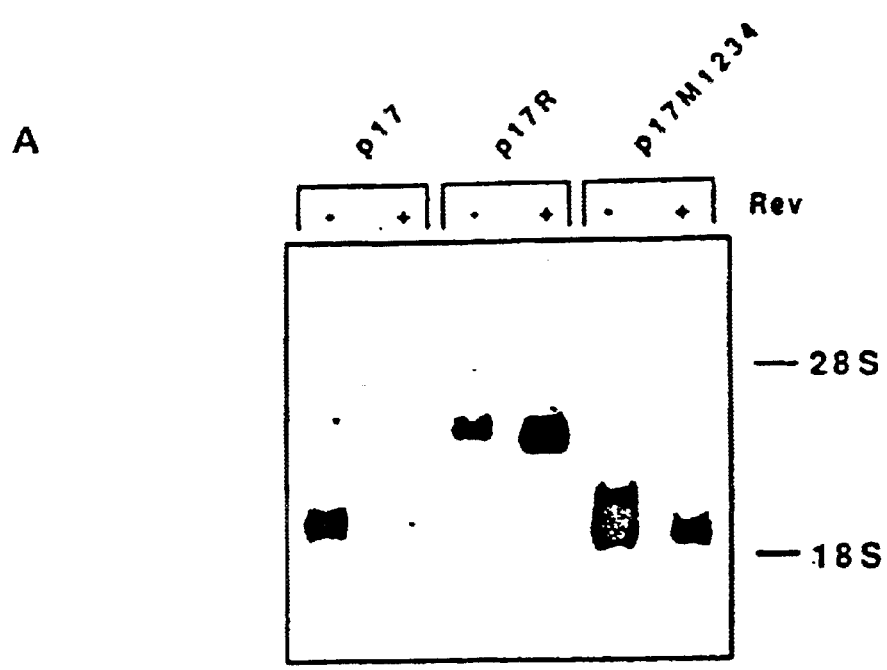
B
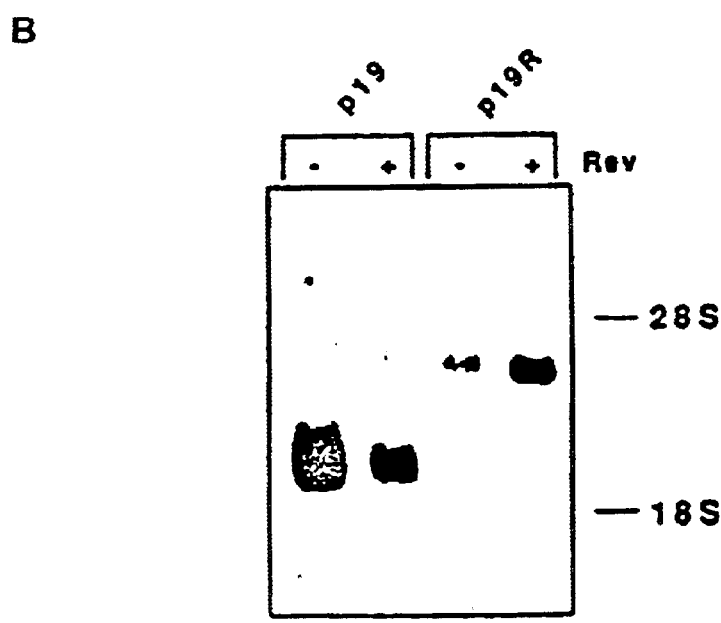
Figure 3

```
336
atg ggt gcg aga gcg tca gta tta agc ggg gga gaa tta gat cga tgg gaa aaa att cgg 396                           M1
tta agg cca gcc gga aag aaa aaa tat aaa tta aaa cat ata gta tgg gca agc agg gag
        G   G   C   G C       G   C   C 456
cta gaa cga ttc gca gtt aat cct ggc ctg tta gaa aca tca gaa ggc tgt aga caa ata 516                                    M2
ctg gga cag cta caa cca tcc ctt cag aca gga tca gaa gaa ctt aga tca tta tat aat
                         G   G   C         C       C   C 576                         M3
aca gta gca acc ctc tat tgt gtg cat caa agg ata gag ata aaa gac acc aag gaa gct
            C   G C       C           C   G 636                             M4
tta gac aag ata gag gaa gag caa aac aaa agt aag aaa aaa gca cag caa gca gca gct
                        G   TCC             G   G   C           G 696
gac aca gga cac agc aat cag gtc agc caa aat tac
```

Figure 4

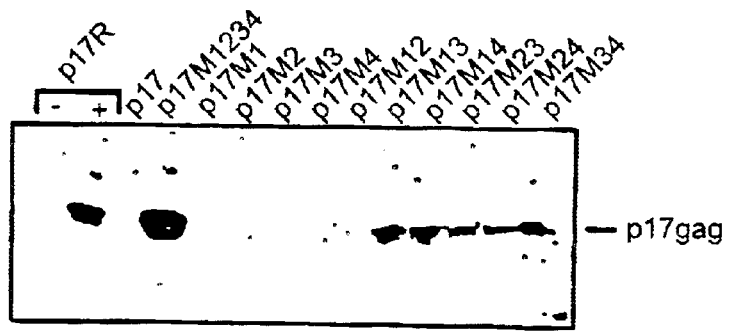

Figure 5

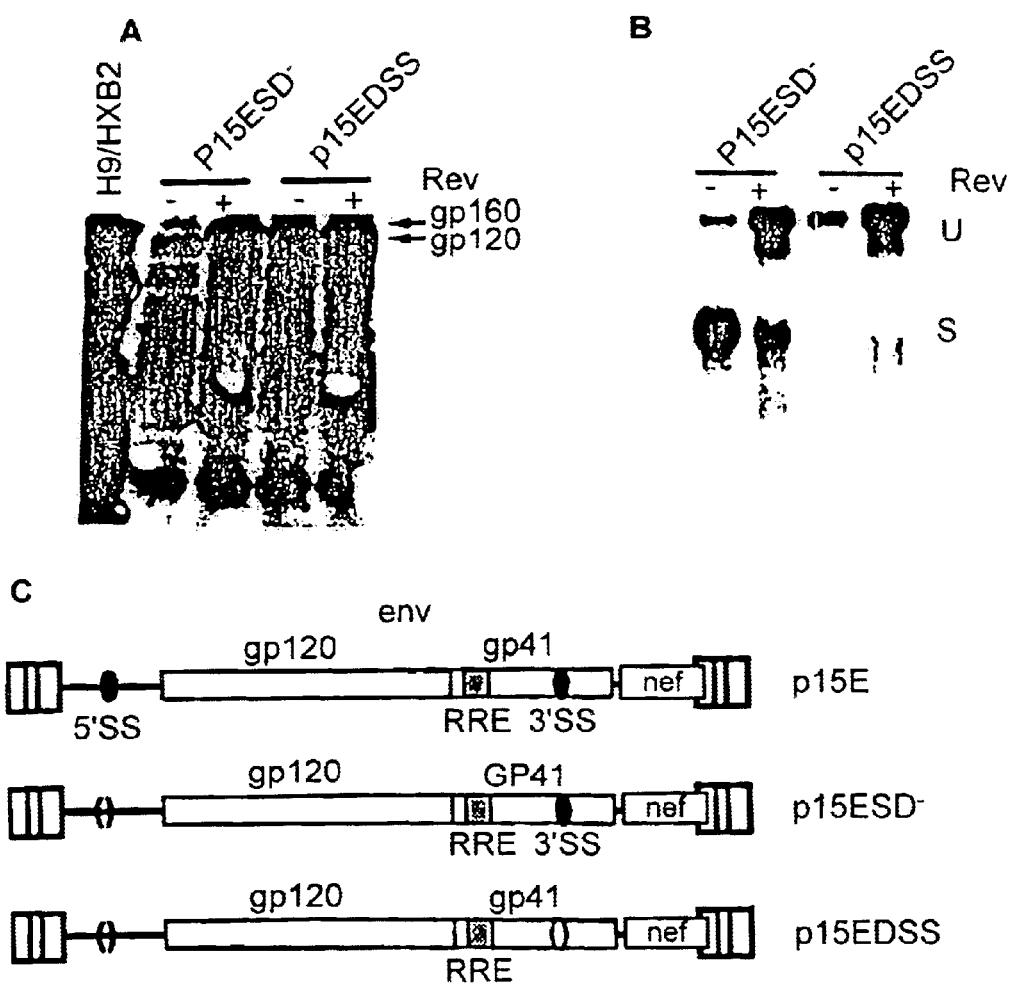

POINT MUTATIONS ELIMINATING THE NEGATIVE EFFECTS OF CRS IN THE pol REGION
(nucleotides 3700-4194) (SEQ ID NO:127)

GGTACCAGCACACAAAGGAATTGGAGGAAATGAACAAGTAGATAAATTAGTCAGTGCTGGAATCAGGAAAGTACTATTTT

TAGATGGAATAGATAAGGCCCAAGATGAACATGAGAAATATCACAGTAATTGGAGAGCAATGGCTAGTGATTTTAACCTG

CCACCTGTAGTAGCAAAAGAAATAGTAGCCAGCTGTGATAAATGTCAGCTAAAAGGAGAAGCCATGCATGGACAAGTAGA

CTGTAGTCCAGGAATATGGCAACTAGATTGTACACATTTAGAAGGAAAAGTTATCCTGGTAGCAGTTCATGTAGCCAGTG
g g c c g cc g g g g g

GATATATAGAAGCAGAAGTTATTCCAGCAGAAACAGGGCAGGAAACAGCATATTTTCTTTTAAAATTAGCAGGAAGATGG

CCAGTAAAAACAATACATACTGACAATGGCAGCAATTTCACCGGTGCTACGGTTAGGGCCGCCTGTTGGTGGGCGGGAAT
c g c a c t

CAAGCAGGAATTTGG

Figure 13

COMPLETE NUCLEOTIDE SEQUENCE OF p37M-1-10D
AND
AMINO ACID SEQUENCE OF p37$^{gag}$ PROTEIN (SEQ ID NO:129)

```
  1 TGGAAGGGCT AATTTGGTCC CAAAAAAGAC AAGAGATCCT TGATCTGTGG ATCTACCACA CACAAGGCTA

71 CTTCCCTGAT TGGCAGAACT ACACACCACG GCCAGGGATC AGATATCCAC TGACCTTTGG ATGGTGCTTC

141 AAGTTAGTAC CAGTTGAACC AGAGCAAGTA GAAGAGGCCA AATAAGGAGA GAAGAACAGC TTGTTACACC

211 CTATGAGCCA GCATGGGATG GAGGACCCGG AGGGAGAAGT ATTAGTGTGG AACTTTGACA GCCTCCTAGC

281 ATTTCGTCAC ATGGCCCGAG AGCTGGATCC GGAGTACTAC AAAGACTGCT GACATCGAGC TTTCTACAAG

351 GGACTTTCCG CTGGGGACTT TCCAGGGAGG TGTGGCCTGG GCGGGACTGG GGAGTGGCGA GCCCTCAGAT

421 GCTACATATA AGCAGCTGCT TTTTGCCTGT ACTGGGTCTC TCTGGTTAGA CCAGATCTGA GCCTGGGAGC

491 TCTCTGGCTA ACTAGGGAAC CCACTGCTTA AGCCTCAATA AAGCTTGCCT TGAGTGCTCA AAGTAGTGTG

561 TGCCCGTCTG TTGTGTGACT CTGGTAACTA GAGATCCCTC AGACCCTTTT AGTCAGTGTG GAAAATCTCT

631 AGCAGTGGCG CCCGAACAGG GACTTGAAAG CGAAAGTAAA GCCAGAGGAG ATCTCTCGAC GCAGGACTCG
              BssHII (711)
701 GCTTGCTGAAGCGCGCGTCGACAGAGAGATGGGTGCGAGAGCGTCAGTATTAAGCGGGGGAGAATTAGATCGATGG
                                        1▸MetGlyAlaArgAlaSerValLeuSerGlyGlyGluLeuAspArgTrp

777 GAAAAAATTCGGTTAAGGCCAGGGGGAAAGAAGAAGTACAAGCTAAAGCACATCGTATGGGCAAGCAGGGAGCTAG
    17▸GluLysIleArgLeuArgProGlyGlyLysLysLysTyrLysLeuLysHisIleValTrpAlaSerArgGluLeuG

853 AACGATTCGCAGTTAATCCTGGCCTGTTAGAAACATCAGAAGGCTGTAGACAAATACTGGGACAGCTACAACCATC
    42▸luArgPheAlaValAsnProGlyLeuLeuGluThrSerGluGlyCysArgGlnIleLeuGlyGlnLeuGlnProSe

929 CCTTCAGACAGGATCAGAGGAGCTTCGATCACTATACAACACAGTAGCAACCCTCTATTGTGTGCACCAGCGGATA
    67▸rLeuGlnThrGlySerGluGluLeuArgSerLeuTyrAsnThrValAlaThrLeuTyrCysValHisGlnArgIle

1005 GAGATCAAGGACACCAAGGAAGCTTTAGACAAGATAGAGGAAGAGCAAAACAAGTCCAAGAAGAAGGCCCAGCAGG
    93▸GluIleLysAspThrLysGluAlaLeuAspLysIleGluGluGluGlnAsnLysSerLysLysLysAlaGlnGlnA

1081 CAGCAGCTGACACAGGACACAGCAATCAGGTCAGCCAAAATTACCCTATAGTGCAGAACATCCAGGGGCAAATGGT
    118▸laAlaAlaAspThrGlyHisSerAsnGlnValSerGlnAsnTyrProIleValGlnAsnIleGlnGlyGlnMetVa

1157 ACATCAGGCCATATCACCTAGAACTTTAAATGCATGGGTAAAAGTAGTACAAGAGAAGGCTTTCAGCCCAGAAGTG
    11▸lHisGlnAlaIleSerProArgThrLeuAsnAlaTrpValLysValValGluGluLysAlaPheSerProGluVal

1233 ATACCCATGTTTTCAGCATTATCAGAAGGAGCCACCCCACAGGACCTGAACACGATGTTGAACACCGTGGGGGGAC
    37▸IleProMetPheSerAlaLeuSerGlyGlyAlaThrProGlnAspLeuAsnThrMetLeuAsnThrValGlyGlyH

1309 ATCAAGCAGCCATGCAAATGTTAAAAGAGACCATCAATGAGGAAGCTGCAGAATGGGATAGAGTGCATCCAGTGCA
    62▸isGlnAlaAlaMetGlnMetLeuLysGluThrIleAsnGluGluAlaAlaGluTrpAspArgValHisProValHi

1385 TGCAGGGCCTATTGCACCAGGCCAGATGAGAGAACCAAGGGGAAGTGACATAGCAGGAACTACTAGTACCCTTCAG
    87▸sAlaGlyProIleAlaProGlyGlnMetArgGluProArgGlySerAspIleAlaGlyThrThrSerThrLeuGln

1461 GAACAAATAGGATGGATGACAAATAATCCACCTATCCCAGTAGGAGAGATCTACAAGAGGTGGATAATCCTGGGAT
    113▸GluGlnIleGlyTrpMetThrAsnAsnProProIleProValGlyGluIleTyrLysArgTrpIleIleLeuGlyL

1537 TGAACAAGATCGTGAGGATGTATAGCCCTACCAGCATTCTGGACATAAGACAAGGACCAAAGGAACCCTTTAGAGA
    138▸euAsnLysIleValArgMetTyrSerProThrSerIleLeuAspIleArgGlnGlyProLysGluProPheArgAs
```

Figure 14B

```
1613 CTATGTAGACCGGTTCTATAAAACTCTAAGAGCTGAGCAAGCTTCACAGGAGGTAAAAAATTGGATGACAGAAACC
 163 pTyrValAspArgPheTyrLysThrLeuArgAlaGluGlnAlaSerGlnGluValLysAsnTrpMetThrGluThr

1689 TTGTTGGTCCAAAATGCGAACCCAGATTGTAAGACCATCCTGAAGGCTCTCGGCCCAGCGGCTACACTAGAAGAAA
 189 LeuLeuValGlnAsnAlaAsnProAspCysLysThrIleLeuLysAlaLeuGlyProAlaAlaThrLeuGluGluM
                                                                  stop (1818)   XbaI (1838)
1765 TGATGACAGCATGTCAGGGAGTAGGAGGACCCGGCCATAAGGCAAGAGTTTTGTAGGGATCCACTAGTTCTAGACT
 214 etMetThrAlaCysGlnGlyValGlyGlyProGlyHisLysAlaArgValLeu
                                                         ApaI(1848)
1841 CGAGGGGGGG CCCGGTACCT TTAAGACCAA TGACTTACAA GGCAGCTGTA GATCTTAGCC ACTTTTTAAA 1911 AGAAAAGGGG GGACTGGAAG GGCTAATTCA CTCCCAAAGA AGACAAGATA TCCTTGATCT GTGGATCTAC 1981 CACACACAAG GCTACTTCCC TGATTGGCAG AACTACACAC CAGGGCCAGG GGTCAGATAT CCACTGACCT 2051 TTGGATGGTG CTACAAGCTA GTACCAGTTG AGCCAGATAA GGTAGAAGAG GCCAATAAAG GAGAGAACAC 2121 CAGCTTGTTA CACCCTGTGA GCCTGCATGG AATGGATGAC CCTGAGAGAG AAGTGTTAGA GTGGAGGTTT 2191 GACAGCCGCC TAGCATTTCA TCACGTGGCC CGAGAGCTGC ATCCGGAGTA CTTCAAGAAC TGCTGACATC 2261 GAGCTTGCTA CAAGGGACTT TCCGCTGGGG ACTTTCCACG GAGGCGTGCC CTGGGCGGGA CTGGGGAGTG 2331 GCGAGCCCTC AGATGCTGCA TATAAGCAGC TGCTTTTTGC CTCTACTGGG TCTCTCTGGT TAGACCAGAT 2401 CTGAGCCTGG GAGCTCTCTG GCTAACTAGG GAACCCACTG CTTAAGCCTC AATAAAGCTT GCCTTGAGTG 2471 CTTCAAGTAG TGTGTGCCCG TCTGTTGTGT GACTCTGGTA ACTAGAGATC CCTCAGACCC TTTTAGTCAG 2541 TGTGGAAAAT CTCTAGCACC CCCCAGGAGG TAGAGGTTGC AGTGAGCCAA GATCGCGCCA CTGCATTCCA 2611 GCCTGGGCAA GAAAACAAGA CTGTCTAAAA TAATAATAAT AAGTTAAGGG TATTAAATAT ATTTATACAT
2681 GGAGGTCATA AAAATATATA TATTTGGGCT GGGCGCAGTG GCTCACACCT GCGCCCGGCC CTTTGGGAGG
2751 CCGAGGCAGG TGGATCACCT GAGTTTGGGA GTTCCAGACC AGCCTGACCA ACATGGAGAA ACCCCTTCTC
2821 TGTGTATTTT TAGTAGATTT TATTTTATGT GTATTTATT CACAGGTATT TCTGGAAAAC TGAAACTGTT
2891 TTTCCTCTAC TCTGATACCA CAAGAATCAT CAGCACAGAG GAAGACTTCT GTGATCAAAT GTGGTGGGAG
2961 AGGGAGGTTT TCACCAGCAC ATGAGCAGTC AGTTCTGCCG CAGACTCGGC GGGTGTCCTT CGGTTCAGTT
3031 CCAACACCGC CTGCCTGGAG AGAGGTCAGA CCACAGGGTG AGGGCTCAGT CCCCAAGACA TAAACACCCA
3101 AGACATAAAC ACCCAACAGG TCCACCCCGC CTGCTGCCCA GGCAGAGCCG ATTCACCAAG ACGGGAATTA
3171 GGATAGAGAA AGAGTAAGTC ACACAGAGCC GGCTGTGCGG GAGAACGGAG TTCTATTATG ACTCAAATCA
3241 GTCTCCCCAA GCATTCGGGG ATCAGAGTTT TTAAGGATAA CTTAGTGTGT AGGGGGCCAG TGAGTTGGAG
3311 ATGAAAGCGT AGGGAGTCGA AGGTGTCCTT TTGCGCCGAG TCAGTTCCTG GGTGGGGGCC ACAAGATCGG
3381 ATGAGCCAGT TTATCAATCC GGGGGTGCCA GCTGATCCAT GGAGTGCAGG GTCTGCAAAA TATCTCAAGC
3451 ACTGATTGAT CTTAGGTTTT ACAATAGTGA TGTTACCCCA GGAACAATTT GGGGAAGGTC AGAATCTTGT
3521 AGCCTGTAGC TGCATGACTC CTAAACCATA ATTTCTTTTT TGTTTTTTTT TTTTTATTTT TGAGACAGGG
                                                                    PstI (3639)
3591 TCTCACTCTG TCACCTAGGC TGGAGTGCAG TGGTGCAATC ACAGCTCACT GCAGCCCCTA GAGCGGCCGC
3661 CACCGCGGTG GAGCTCCAAT TCGCCCTATA GTGAGTCGTA TTACAATTCA CTGGCCGTCG TTTTACAACG
3731 TCGTGACTGG GAAAACCCTG GCGTTACCCA ACTTAATCGC CTTGCAGCAC ATCCCCCTTT CGCCAGCTGG
3801 CGTAATAGCG AAGAGGCCCG CACCGATCGC CCTTCCCAAC AGTTGCGCAG CCTGAATGGC GAATGGCGCG
3871 AAATTGTAAA CGTTAATATT TTGTTAAAAT TCGCGTTAAA TTTTTGTTAA ATCAGCTCAT TTTTTAACCA
3941 ATAGGCCGAA ATCGGCAAAA TCCCTTATAA ATCAAAAGAA TAGACCGAGA TAGGGTTGAG TGTTGTTCCA
4011 GTTTGGAACA AGAGTCCACT ATTAAAGAAC GTGGACTCCA ACGTCAAAGG GCGAAAAACC GTCTATCAGG
4081 GCGATGGCCC ACTACGTGAA CCATCACCCT AATCAAGTTT TTTGGGGTCG AGGTGCCGTA AAGCACTAAA
4151 TCGGAACCCT AAAGGGAGCC CCCGATTTAG AGCTTGACGG GGAAAGCCGG CGAACGTGGC GAGAAAGGAA
4221 GGGAAGAAAG CGAAAGGAGC GGGCGCTAGG GCGCTGGCAA GTGTAGCGGT CACGCTGCGC GTAACCACCA
4291 CACCCGCCGC GCTTAATGCG CCGCTACAGG GCGCGTCCCA GGTGGCACTT TTCGGGGAAA TGTGCGCGGA
4361 ACCCCTATTT GTTTATTTTT CTAAATACAT TCAAATATGT ATCCGCTCAT GAGACAATAA CCCTGATAAA
```

Figure 14C

```
4431 TGCTTCAATA ATATTGAAAA AGGAAGAGTA TGAGTATTCA ACATTTCCGT GTCGCCCTTA TTCCCTTTTT
4501 TGCGGCATTT TGCCTTCCTG TTTTTGCTCA CCCAGAAACG CTGGTGAAAG TAAAAGATGC TGAAGATCAG
4571 TTGGGTGCAC GAGTGGGTTA CATCGAACTG GATCTCAACA GCGGTAAGAT CCTTGAGAGT TTTCGCCCCG
4641 AAGAACGTTT TCCAATGATG AGCACTTTTA AAGTTCTGCT ATGTGGCGCG GTATTATCCC GTATTGACGC
4711 CGGGCAAGAG CAACTCGGTC GCCGCATACA CTATTCTCAG AATGACTTGG TTGAGTACTC ACCAGTCACA
4781 GAAAAGCATC TTACGGATGG CATGACAGTA AGAGAATTAT GCAGTGCTGC CATAACCATG AGTGATAACA
4851 CTGCGGCCAA CTTACTTCTG ACAACGATCG GAGGACCGAA GGAGCTAACC GCTTTTTTGC ACAACATGGG
4921 GGATCATGTA ACTCGCCTTG ATCGTTGGGA ACCGGAGCTG AATGAAGCCA TACCAAACGA CGAGCGTGAC
4991 ACCACGATGC CTGTAGCAAT GGCAACAACG TTGCGCAAAC TATTAACTGG CGAACTACTT ACTCTAGCTT
5061 CCCGGCAACA ATTAATAGAC TGGATGGAGG CGGATAAAGT TGCAGGACCA CTTCTGCGCT CGGCCCTTCC
5131 GGCTGGCTGG TTTATTGCTG ATAAATCTGG AGCCGGTGAG CGTGGGTCTC GCGGTATCAT TGCAGCACTG
5201 GGGCCAGATG GTAAGCCCTC CCGTATCGTA GTTATCTACA CGACGGGGAG TCAGGCAACT ATGGATGAAC
5271 GAAATAGACA GATCGCTGAG ATAGGTGCCT CACTGATTAA GCATTGGTAA CTGTCAGACC AAGTTTACTC
5341 ATATATACTT TAGATTGATT TAAAACTTCA TTTTTAATTT AAAAGGATCT AGGTGAAGAT CCTTTTTGAT
5411 AATCTCATGA CCAAAATCCC TTAACGTGAG TTTTCGTTCC ACTGAGCGTC AGACCCCGTA GAAAAGATCA
5481 AAGGATCTTC TTGAGATCCT TTTTTTCTGC GCGTAATCTG CTGCTTGCAA ACAAAAAAAC CACCGCTACC
5551 AGCGGTGGTT TGTTTGCCGG ATCAAGAGCT ACCAACTCTT TTTCCGAAGG TAACTGGCTT CAGCAGAGCG
5621 CAGATACCAA ATACTGTCCT TCTAGTGTAG CCGTAGTTAG GCCACCACTT CAAGAACTCT GTAGCACCGC
5691 CTACATACCT CGCTCTGCTA ATCCTGTTAC CAGTGGCTGC TGCCAGTGGC GATAAGTCGT GTCTTACCGG
5761 GTTGGACTCA AGACGATAGT TACCGGATAA GGCGCAGCGG TCGGGCTGAA CGGGGGGTTC GTGCACACAG
5831 CCCAGCTTGG AGCGAACGAC CTACACCGAA CTGAGATACC TACAGCGTGA GCTATGAGAA AGCGCCACGC
5901 TTCCCGAAGG GAGAAAGGCG GACAGGTATC CGGTAAGCGG CAGGGTCGGA ACAGGAGAGC GCACCAGGGA
5971 GCTTCCAGGG GGAAACGCCT GGTATCTTTA TAGTCCTGTC GGGTTTCGCC ACCTCTGACT TGAGCGTCGA
6041 TTTTTGTGAT GCTCGTCAGG GGGCGGAGC CTATGGAAAA ACGCCAGCAA CGCGGCCTTT TTACGGTTCC
6111 TGGCCTTTTG CTGGCCTTTT GCTCACATGT TCTTTCCTGC GTTATCCCCT GATTCTGTGG ATAACCGTAT
6181 TACCGCCTTT GAGTGAGCTG ATACCGCTCG CCGCAGCCGA ACGACCGAGC GCAGCGAGTC AGTGAGCGAG
6251 GAAGCGGAAG AGCGCCCAAT ACGCAAACCG CCTCTCCCCG CGCGTTGGCC GATTCATTAA TGCAGCTGGC
6321 ACGACAGGTT TCCCGACTGG AAAGCGGGCA GTGAGCGCAA CGCAATTAAT GTGAGTTAGC TCACTCATTA
6391 GGCACCCCAG GCTTTACACT TTATGCTTCC GGCTCGTATG TTGTGTGGAA TTGTGAGCGG ATAACAATTT
6461 CACACAGGAA ACAGCTATGA CCATGATTAC GCCAAGCTCG GAATTAACCC TCACTAAAGG GAACAAAAGC
     PstI (6533)
6531 TGCTGCAGGG TCCCTAACTG CCAAGCCCCA CAGTGTGCCC TGAGGCTGCC CCTTCCTTCT AGCGGCTGCC
6601 CCCACTCGGC TTTGCTTTCC CTAGTTTCAG TTACTTGCGT TCAGCCAAGG TCTGAAACTA GGTGCGCACA
6671 GAGCGGTAAG ACTGCGAGAG AAAGAGACCA GCTTTACAGG GGGTTTATCA CAGTGCACCC TGACAGTCGT
6741 CAGCCTCACA GGGGGTTTAT CACATTGCAC CCTGACAGTC GTCAGCCTCA CAGGGGGTTT ATCACAGTGC
6811 ACCCTTACAA TCATTCCATT TGATTCACAA TTTTTTTAGT CTCTACTGTG CCTAACTTGT AAGTTAAATT
6881 TGATCAGAGG TGTGTTCCCA GAGGGGAAAA CAGTATATAC AGGGTTCAGT ACTATCGCAT TTCAGCCTC
6951 CACCTGGGTC TTGGAATGTG TCCCCCGAGG GGTGATGACT ACCTCAGTTG GATCTCCACA GGTCACAGTG
7021 ACACAAGATA ACCAAGACAC CTCCCAAGGC TACCACAATG GGCCGCCCTC CACGTGCACA TGGCCGGAGG
7091 AACTGCCATG TCGGAGGTGC AAGCACACCT GCGCATCAGA GTCCTTGGTG TGGAGGGAGG GACCAGCGCA
7161 GCTTCCAGCC ATCCACCTGA TGAACAGAAC CTAGGGAAAG CCCCAGTTCT ACTTACACCA GGAAAGGC
```

Figure 14D

METHOD OF ELIMINATING INHIBITORY/ INSTABILITY REGIONS OF MRNA

This application is a continuation of U.S. Ser. No. 09/678,437, filed Oct. 2, 2000, now U.S. Pat. No. 6,414,132; which is a continuation of U.S. Ser. No. 09/414,117, filed Oct. 8, 1999, now U.S. Pat. No. 6,291,664; which is a continuation of U.S. Ser. No. 08/850,049, filed May 2, 1997, now U.S. Pat. No. 5,965,726; which is a continuation of U.S. Ser. No. 08/050,478, field Jan. 26, 1994 now U.S. Pat. No. 5,972,596; which is a 371 of PCT/US93/02908, filed Mar. 29, 1993; which is a continuation-in part of U.S. Ser. No. 07/858,747, filed Mar. 27, 1992, now U.S. Pat. No. 6,174,666B1. The disclosures of each of these applications is hereby incorporated by reference.

I. TECHNICAL FIELD

The invention relates to methods of increasing the stability and/or utilization of a mRNA produced by a gene by mutating regulatory or inhibitory/instability sequences (INS) in the coding region of the gene which prevent or reduce expression. The invention also relates to constructs, including expression vectors, containing genes mutated in accordance with these methods and host cells containing these constructs.

The methods of the invention are particularly useful for increasing the stability and/or utilization of a mRNA without changing its protein coding capacity. These methods are useful for allowing or increasing the expression of genes which would otherwise not be expressed or which would be poorly expressed because of the presence of INS regions in the mRNA transcript. Thus, the methods, constructs and host cells of the invention are useful for increasing the amount of protein produced by any gene which encodes an mRNA transcript which contains an INS.

The methods, constructs and host cells of the invention are useful for increasing the amount of protein produced from genes such as those coding for growth factors, interferons, interleukins, the fos proto-oncogene protein, and HIV-1 gag and env, for example.

The invention also relates to using the constructs of the invention in immunotherapy and immunoprophylaxis, e.g., as a vaccine, or in genetic therapy after expression in humans. Such constructs can include or be incorporated into retroviral or other expression vectors or they may also be directly injected into tissue cells resulting in efficient expression of the encoded protein or protein fragment. These constructs may also be used for in-vivo or in-vitro gene replacement, e.g., by homologous recombination with a target gene in-situ.

The invention also relates to certain exemplified constructs which can be used to simply and rapidly detect and/or define the boundaries of inhibitory/instability sequences in any mRNA, methods of using these constructs, and host cells containing these constructs. Once the INS regions of the mRNAs have been located and/or further defined, the nucleotide sequences encoding these INS regions can be mutated in accordance with the method of this invention to allow the increase in stability and/or utilization of the mRNA and, therefore, allow an increase in the amount of protein produced from expression vectors encoding the mutated mRNA.

II. BACKGROUND ART

While much work has been devoted to studying transcriptional regulatory mechanisms, it has become increasingly clear that post-transcriptional processes also modulate the amount and utilization of RNA produced from a given gene. These post-transcriptional processes include nuclear post-transcriptional processes (e.g., splicing, polyadenylation, and transport) as well as cytoplasmic RNA degradation. All these processes contribute to the final steady-state level of a particular transcript. These points of regulation create a more flexible regulatory system than any one process could produce alone. For example, a short-lived message is less abundant than a stable one, even if it is highly transcribed and efficiently processed. The efficient rate of synthesis ensures that the message reaches the cytoplasm and is translated, but the rapid rate of degradation guarantees that the mRNA does not accumulate to too high a level. Many RNAs, for example the mRNAS for proto-oncogenes c-myc and c-fos, have been studied-which exhibit this kind of regulation in that they are expressed at very low levels, decay rapidly and are modulated quickly and transiently under different conditions. See, M. Hentze, Biochim. Biophys. Acta 1090:281–292 (1991) for a review. The rate of degradation of many of these mRNAs has been shown to be a function of the presence of one or more instability/inhibitory sequences within the mRNA itself.

Some cellular genes which encode unstable or short-lived mRNAs have been shown to contain A and U-rich (AU-rich) INS within the 3' untranslated region (3' UTR) of the transcript mRNA. These cellular genes include the genes encoding granulocyte-monocyte colony stimulating factor (GM-CSF), whose AU-rich 3'UTR sequences (containing 8 copies of the sequence motif AUUUA) are more highly conserved between mice and humans than the protein encoding sequences themselves (93% versus 65%) (G. Shaw, and R. Kamen, Cell 46:659–667 (1986)) and the myc proto-oncogene (c-myc), whose untranslated regions are conserved throughout evolution (for example, 81% for man and mouse) (M. Cole and S. E. Mango, Enzyme 44:167–180 (1990)). Other unstable or short-lived mRNAs which have been shown to contain AU-rich sequences within the 3' UTR include interferons (alpha, beta and gamma IFNs); interleukins (IL1, IL2 and IL3); tumor necrosis factor (TNF); lymphotoxin (Lym); IgG1 induction factor (IgG IF); granulocyte colony stimulating factor (G-CSF), myb proto-oncogene (c-myb); and sis proto-oncogene (c-sis) (G. Shaw, and R. Kamen, Cell 46:659–667 (1986)). See also, R. Wisdom and W. Lee, Gen. & Devel. 5:232–243 (1991) (c-myc; A. Shyu et al., Gen. & Devel. 5:221–231 (1991) (c-fos); T. Wilson and R. Treisman, Nature 336:396–399 (1988) (c-fos); T. Jones and M. Cole, Mol. Cell Biol. 7:4513–4521 (1987) (c-myc); V. Kruys et al., Proc. Natl. Acad. Sci. USA. 89:673–677 (1992) (TNF); D. Koeller et al., Proc. Natl. Acad. Sci. USA. 88:7778–7782 (1991) (transferrin receptor (TfR) and c-fos); I. Laird-Offringa et al., Nucleic Acids Res. 19:2387–2394 (1991) (c-myc); D. Wreschner and G. Rechavi, Eur. J. Biochem. 172:333–340 (1988) (which contains a survey of genes and relative stabilities); Bunnell et al., Somatic Cell and Mol. Genet. 16:151–162 (1990) (galactosyltransferase-associated protein (GTA), which contains an AU-rich 3' UTR with regions that are 98% similar among humans, mice and rats); and Caput et al. Proc. Natl. Acad. Sci. 83:1670–1674 (1986) (TNF, which contains a 33 nt AU-rich sequence conserved in toto in the murine and human TNF mRNAs).

Some of these cellular genes which have been shown to contain INS within the 3' UTR of their mRNA have also been shown to contain INS within the coding region. See, e.g., R. Wisdom, and W. Lee, Gen. & Devel. 5:232–243 (1991) (c-myc); A. Shyu et al., Gen. & Devel. 5:221–231 (1991) (c-fos).

Like the cellular mRNAs, a number of HIV-1 mRNAs have also been shown to contain INS within the protein coding regions, which in some cases coincide with areas of high AU-content. For example, a 218 nucleotide region with high AU content (61.5%) present in the HIV-1 gag coding sequence and located at the 5' end of the gag gene has been implicated in the inhibition of gag expression. S. Schwartz et al., J. Virol. 66:150–159 (1992). Further experiments have indicated the presence of more than one INS in the gag-protease gene region of the viral genome (see below). Regions of high AU content have been found in the HIV-1 gag/pol and env INS regions. The AUUUA sequence is not present in the gag coding sequence, but it is present in many copies within gag/pol and env coding regions. S. Schwartz et al., J. Virol. 66:150–159 (1992). See also, e.g., M. Emerman, Cell 57:1155–1165 (1989) (env gene contains both 3' UTR and internal inhibitory/instability sequences); C. Rosen, Proc. Natl. Acad. Sci., USA 85:2071–2075 (1988) (env); M. -Hadzopoulou-Cladaras et al., J. Virol. 63:1265–1274 (1989) (env); F. Maldarelli et al., J. Virol. 65:5732–5743 (1991) (gag/pol); A. Cochrane et al., J. Virol. 65:5303–5313 (1991) (pol). F. Maldarelli et al., supra, note that the direct analysis of the function of INS regions in the context of a replication-competent, full-length HIV-1 provirus is complicated by the fact that the intragenic INS are located in the coding sequences of virion structural proteins. They further note that changes in these intragenic INS sequences would in most cases affect protein sequences as well, which in turn could affect the replication of such mutants.

The INS regions are not necessarily AU-rich. For example, the c-fos coding region INS is structurally unrelated to the AU-rich 3' UTR INS (A. Shyu et al., Gen. & Devel. 5:221–231 (1991), and some parts of the env coding region, which appear to contain INS elements, are not AU-rich. Furthermore, some stable transcripts also carry the AUUUA motif in their 3' UTRs, implying either that this sequence alone is not sufficient to destabilize a transcript, or that these messages also contain a dominant stabilizing element (M. Cole and S. E. Mango, Enzyme 44:167–180 (1990)). Interestingly, elements unique to specific mRNAs have also been found which can stabilize a mRNA transcript. One example is the Rev responsive element, which in the presence of Rev protein promotes the transport, stability and utilization of a mRNA transcript (B. Felber et al., Proc. Natl. Acad. Sci. USA 86:1495–1499 (1989)).

It is not yet known whether the AU sequences themselves, and specifically the Shaw-Kamen sequence, AUUUA, act as part or all of the degradation signal. Nor is it clear whether this is the only mechanism employed for short-lived messages, or if there are different classes of RNAS, each with its own degradative system. See, M. Cole and S. E. Mango, Enzyme 44:167–180 (1990) for a review; see also, T. Jones and M. Cole, Mol. Cell. Biol. 7:4513–4521 (1987). Mutation of the only copy of the AUUUA sequence in the c-myc RNA INS region has no effect on RNA turnover, therefore the inhibitory sequence may be quite different from that of GM-CSF (M. Cole and S. E. Mango, Enzyme 44:167–180 (1990)), or else the mRNA instability may be due to the presence of additional INS regions within the mRNA.

Previous workers have made mutations in genes encoding AU-rich inhibitory/instability sequences within the 3' UTR of their transcript mRNAs. For example, G. Shaw and R. Kamen, Cell 46:659–667 (1986), introduced a 51 nucleotide AT-rich sequence from GM-CSF into the 3' UTR of the rabbit β-globin gene. This insertion caused the otherwise stable β-globin mRNA to become highly unstable in vivo, resulting in a dramatic decrease in expression of β-globin as compared to the wild-type control. The introduction of another sequence of the same length, but with 14 G's and C's interspersed among the sequence, into the same site of the 3' UTR of the rabbit β-globin gene resulted in accumulation levels which were similar to that of wild-type β-globin mRNA. This control sequence did not contain the motif AUUUA, which occurs seven times in the AU-rich sequence. The results suggested that the presence of the AU-rich sequence in the β-globin mRNA specifically confers instability.

A. Shyu et al., Gen. & Devel. 5:221–231 (1991), studied the AU-rich INS in the 3' UTR of c-fos by disrupting all three AUUUA pentanucleotides by single U-to-A point mutations to preserve the AU-richness of the element while altering its sequence. This change in the sequence of the 3' UTR INS dramatically inhibited the ability of the mutated 3' UTR to destabilize the β-globin message when inserted into the 3' UTR of a β-globin mRNA as compared to the wild-type INS. The c-fos protein-coding region INS (which is structurally unrelated to the 3' UTR INS) was studied by inserting it in-frame into the coding region of a β-globin and observing the effect of deletions on the stability of the heterologous c-fos-β-globin mRNA.

Previous workers have also made mutations in genes encoding inhibitory/instability sequences within the coding region of their transcript mRNAs. For example, P. Carter-Muenchau and R. Wolf, Proc. Natl. Acad. Sci., USA, 86:1138–1142 (1989) demonstrated the presence of a negative control region that lies deep in the coding sequence of the E. coli 6-phosphogluconate dehydrogenase (gnd) gene. The boundaries of the element were defined by the cloning of a synthetic "internal complementary sequence" (ICS) and observing the effect of this internal complementary element on gene expression when placed at several sites within the gnd gene. The effect of single and double mutations introduced into the synthetic ICS element by site-directed mutagenesis on regulation of expression of a gnd-lacz fusion gene correlated with the ability of the respective mRNAs to fold into secondary structures that sequester the ribosome binding site. Thus, the gnd gene's internal regulatory element appears to function as a cis-acting antisense RNA.

M. Lundigran et al., Proc. Natl. Acad. Sci. USA 88:1479–1483 (1991), conducted an experiment to identify sequences linked to btuB that are important for its proper expression and transcriptional regulation in which a DNA fragment carrying the region from −60 to +253 (the coding region starts at +241) was mutagenized and then fused in frame to lacZ. Expression of β-galactosidase from variant plasmids containing a single base change were then analyzed. The mutations were all G•C to A•T transitions, as expected from the mutagenesis procedures used. Among other mutations, a single base substitution at +253 resulted in greatly increased expression of the btuB-lacZ gene fusion under both repressing and nonrepressing conditions.

R. Wisdom and W. Lee, Gen. & Devel. 5:232–243 (1991), conducted an experiment which showed that mRNA derived from a hybrid full length c-myc gene, which contains a mutation in the translation initiation codon from ATG to ATC, is relatively stable, implying that the c-myc coding region inhibitory sequence functions in a translation dependent manner.

R. Parker and A. Jacobson, Proc. Natl. Acad. Sci. USA 87:2780–2784 (1990) demonstrated that a region of 42 nucleotides found in the coding region of *Saccharomyces cerevisiae* MATα1 mRNA, which normally confers low stability, can be experimentally inactivated by introduction of a translation stop codon immediately upstream of this 42 nucleotide segment. The experiments suggest that the decay of MATα1 mRNA is promoted by the translocation of ribosomes through a specific region of the coding sequence. This 42 nucleotide segment has a high content (8 out of 14) of rare codons (where a rare codon is defined by its occurrence fewer than 13 times per 1000 yeast codons (citing S. Aota et al., Nucl. Acids. Res. 16:r315-r402 (1988))) that may induce slowing of translation elongation. The authors of the study, R. Parker and A. Jacobson, state that the concentration of rare codons in the sequences required for rapid decay, coupled with the prevalence of rare codons in unstable yeast mRNAs and the known ability of rare codons to induce translational pausing, suggests a model in which mRNA structural changes may be affected by the particular positioning of a paused ribosome. Another author stated that it would be revealing to find out whether (and how) a kinetic change in translation elongation could affect mRNA stability (M. Hentze, Bioch. Biophys. Acta 1090:281–292 (1991)). R. Parker and A. Jacobson, note, however, that the stable PGK1 mRNA can be altered to include up to 40% rare codons with, at most, a 3-fold effect on steady-state mRNA level and that this difference may actually be due to a change in transcription rates. Thus, these authors conclude, it seems unlikely that ribosome pausing per se is sufficient to promote rapid mRNA decay.

None of the aforementioned references describe or suggest the present invention of locating inhibitory/instability sequences within the coding region of an mRNA and modifying the gene encoding that mRNA to remove these inhibitory/instability sequences by making multiple nucleotide substitutions without altering the coding capacity of the gene.

III. DISCLOSURE OF THE INVENTION

The invention relates to methods of increasing the stability and/or utilization of a mRNA produced by a gene by mutating regulatory or inhibitory/instability sequences (INS) in the coding region of the gene which prevent or reduce expression. The invention also relates to constructs, including expression vectors, containing genes mutated in accordance with these methods and host cells containing these constructs.

As defined herein, an inhibitory/instability sequence of a transcript is a regulatory sequence that resides within an mRNA transcript and is either (1) responsible for rapid turnover of that mRNA and can destabilize a second indicator/reporter mRNA when fused to that indicator/reporter mRNA, or is (2) responsible for underutilization of a mRNA and can cause decreased protein production from a second indicator/reporter mRNA when fused to that second indicator/reporter mRNA or (3) both of the above. The inhibitory/instability sequence of a gene is the gene sequence that encodes an inhibitory/instability sequence of a transcript. As used herein, utilization refers to the overall efficiency of translation of an mRNA.

The methods of the invention are particularly useful for increasing the stability and/or utilization of a mRNA without changing its protein coding capacity. However, alternative embodiments of the invention in which the inhibitory/instability sequence is mutated in such a way that the amino acid sequence of the encoded protein is changed to include conservative or non-conservative amino acid substitutions, while still retaining the function of the originally encoded protein, are also envisioned as part of the invention.

These methods are useful for allowing or increasing the expression of genes which would otherwise not be expressed or which would be poorly expressed because of the presence of INS regions in the mRNA transcript. The invention provides methods of increasing the production of a protein encoded by a gene which encodes an mRNA containing an inhibitory/instability region by altering the portion of the nucleotide sequence of any gene encoding the inhibitory/instability region.

The methods, constructs and host cells of the invention are useful for increasing the amount of protein produced by any gene which encodes an mRNA transcript which contains an INS. Examples of such genes include, for example, those coding for growth factors, interferons, interleukins, and the fos proto-oncogene protein, as well as the genes coding for HIV-1 gag and env proteins.

The method of the invention is exemplified by the mutational inactivation of an INS within the coding region of the HIV-1 gag gene which results in increased gag expression, and by constructs useful for Rev-independent gag expression in human cells. This mutational inactivation of the inhibitory/instability sequences involves introducing multiple point mutations into the AU-rich inhibitory sequences within the coding region of the gag gene which, due to the degeneracy of nucleotide coding sequences, do not affect the amino acid sequence of the gag protein.

The constructs of the invention are exemplified by vectors containing the gag env, and pol genes which have been mutated in accordance with the methods of this invention and the host cells are exemplified by human HLtat cells containing these vectors.

The invention also relates to using the constructs of the invention in immunotherapy and immunoprophylaxis, e.g., as a vaccine, or in genetic therapy after expression in humans. Such constructs can include or be incorporated into retroviral vectors or other expression vectors or they may also be directly injected into tissue cells resulting in efficient expression of the encoded protein or protein fragment. These constructs may also be used for in-vivo or in-vitro gene replacement, e.g., by homologous recombination with a target gene in-situ.

The invention also relates to certain exemplified constructs which can be used to simply and rapidly detect and/or further define the boundaries of inhibitory/instability sequences in any mRNA which is known or suspected to contain such regions, whether the INS are within the coding region or in the 3'UTR or both. Once the INS regions of the genes have been located and/or further defined through the use of these vectors, the same vectors can be used in mutagenesis experiments to eliminate the identified INS without affecting the coding capacity of the gene, thereby allowing an increase in the amount of protein produced from expression vectors containing these mutated genes. The invention also relates to methods of using these constructs and to host cells containing these constructs.

Figure 1B:
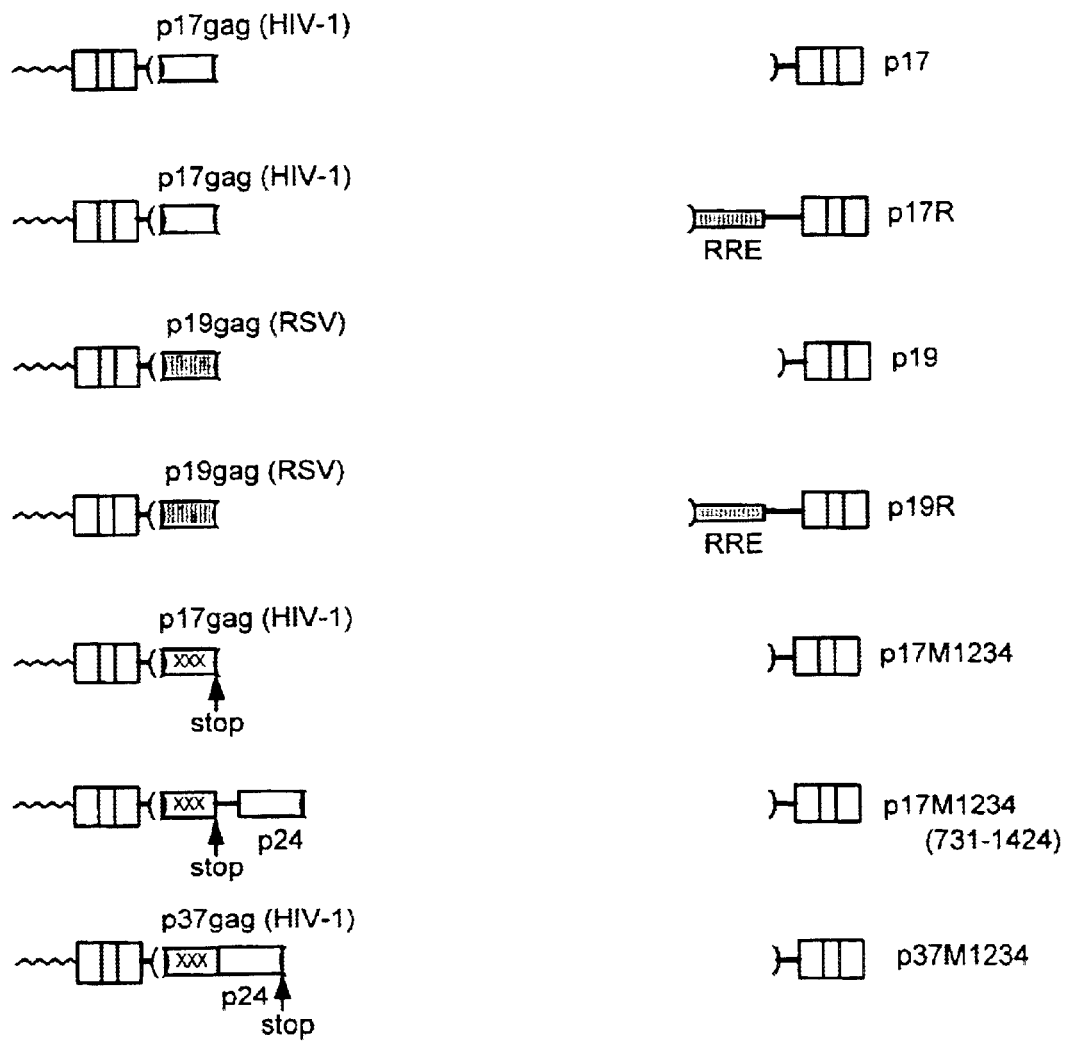
Figure 1C:
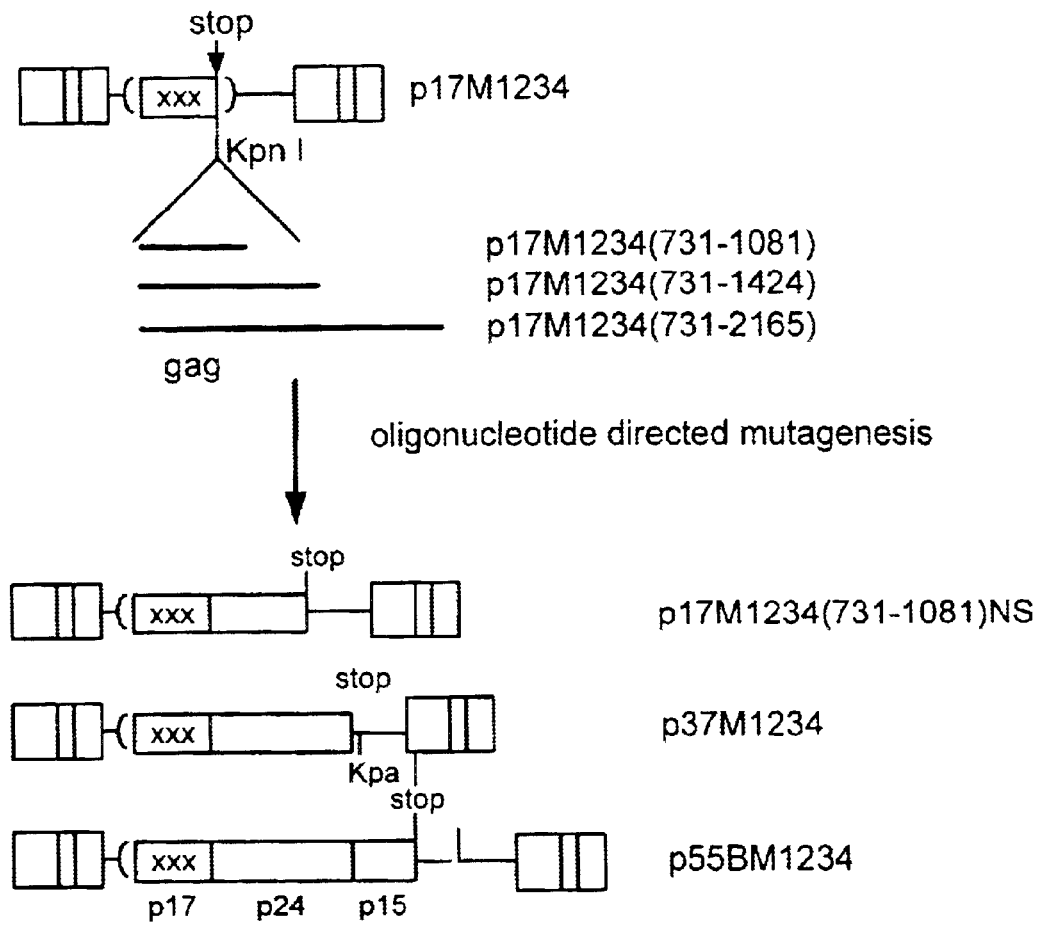
Figure 6:
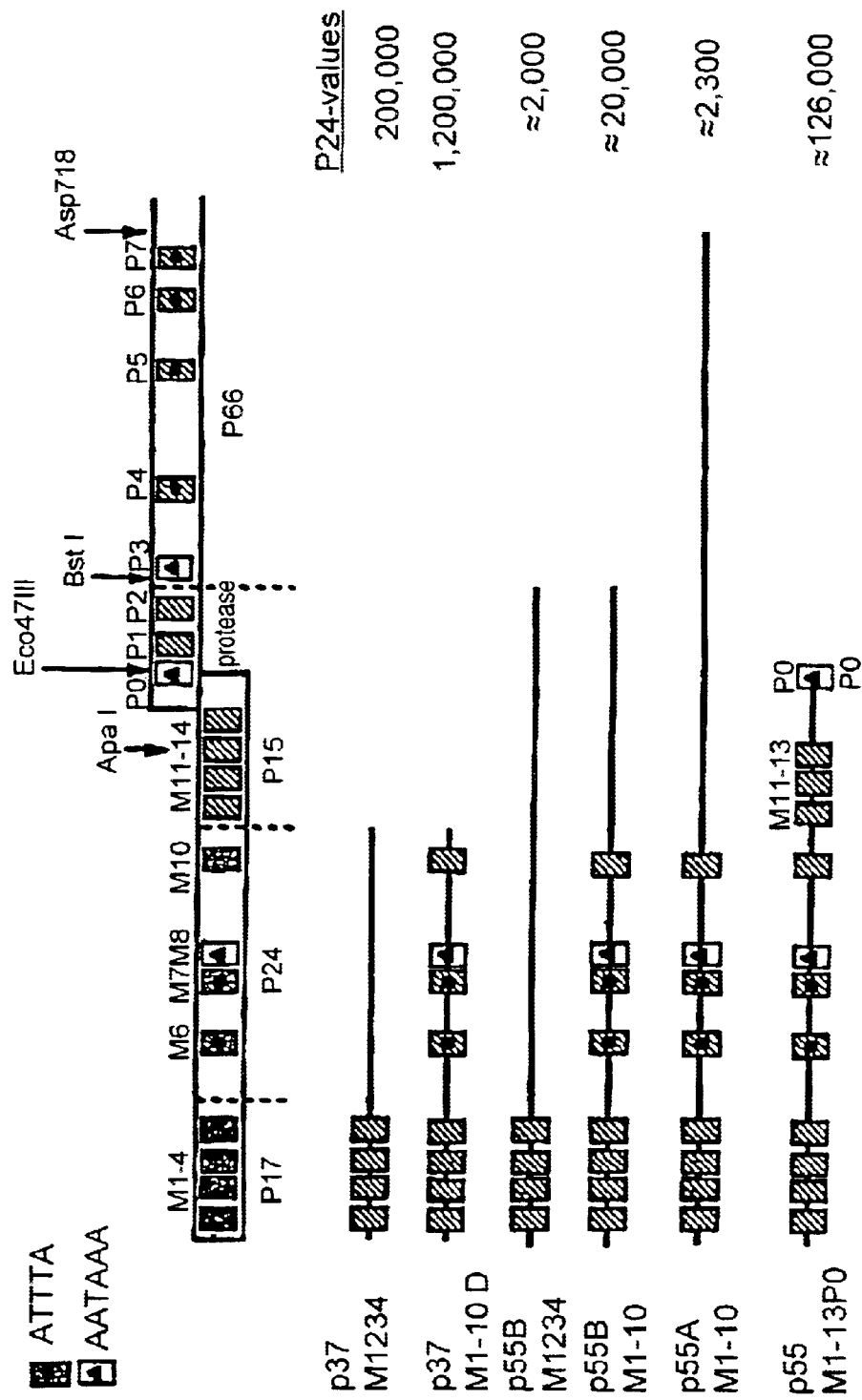

The constructs of the invention which can be used to detect instability/inhibitory regions within an mRNA are exemplified by the vectors, p19, p17M1234, p37M1234 and p37M1-10D, which are set forth in FIG. 1.(B) and FIG. 6. p37M1234 and p37M1-10D are the preferred constructs, due to the existence of a commercially available ELISA test which allows the simple and rapid detection of any changes in the amount of expression of the gag indicator/reporter protein. However, any constructs which contain the elements depicted between the long terminal repeats in the afore-mentioned constructs of FIG. 1.(B) and FIG. 6, and which can be used to detect instability/inhibitory regions within a mRNA, are also envisioned as part of this invention.

The existence of inhibitory/instability sequences has been known in the art, but no solution to the problem which allowed increased expression of the genes encoding the mRNAs containing these sequences within coding regions by making multiple nucleotide substitutions, without altering the coding capacity of the gene, has heretofore been disclosed.

IV. BRIEF DESCRIPTION OF THE DRAWINGS

FIG. 1.(A) Structure of the HIV-1 genome. Boxes indicate the different viral genes. (B) Structure of the gag expression plasmids (see infra). Plasmid p17 contains the complete HIV-1 5' LTR and sequences up to the BssHII restriction site at nucleotide (nt) 257. (The nucleotide numbering refers to the revised nucleotide sequence of the HIV-1 molecular clone pHXB2 (G. Myers et al., Eds. *Human retroviruses and AIDS. A compilation and analysis of nucleic acid and amino acid sequences* (Los Alamos National Laboratory, Los Alamos, N.Mex., 1991), incorporated herein by reference). This sequence is followed by the $p17^{gag}$ coding sequence spanning nt 336–731 (represented as an open box) immediately followed by a translational stop codon and a linker sequence. Adjacent to the linker is the HIV-1 3' LTR from nt 8561 to the last nucleotide of the U5 region. Plasmid p17R contains in addition the 330 nt StyI fragment encompassing the RRE (L. Solomin et al., J Virol 64:6010–6017 (1990)) (represented as a stippled box) 3' to the $p17^{gag}$ coding sequence. The RRE is followed by HIV-1 sequences from nt 8021 to the last nucleotide of the U5 region of the 3' LTR. Plasmids p19 and p19R were generated by replacing the HIV-1 $p17^{gag}$ coding sequence in plasmids p17 and p17R, respectively, with the RSV $p19^{gag}$ coding sequence (represented as a black box). Plasmid p17M1234 is identical to p17, except for the presence of 28 silent nucleotide substitutions within the gag coding region, indicated by XXX. Wavy lines represent plasmid sequences. Plasmid p17M1234(731–1424) and plasmid p37M1234 are described immediately below and in the description. These vectors are illustrative of constructs which can be used to determine whether a particular nucleotide sequence encodes an INS. In this instance, vector p17M1234, which contains an indicator gene (here, $p17^{gag}$) represents the control vector and vectors p17M1234(731–1424) and p37M1234 represent vectors in which the nucleotide sequence of interest (here the $p24^{gag}$ coding region) is inserted into the vector either 3' to the stop codon of the indicator gene or is fused in frame to the coding region of the indicator gene, respectively. (C) Construction of expression vectors for identification of gag INS and for further mutagenesis. p17M1234 was used as a vector to insert additional HIV-1 gag sequences downstream from the coding region of the altered $p17^{gag}$ gene. Three different fragments indicated by nucleotide numbers were inserted into vector p17M1234 as described below. To generate plasmids p17M1234(731–1081), p17M1234 (731–1424) and p17M1234(731–2165), the indicated fragments were inserted 3' to the stop codon of the $p17^{gag}$ coding sequence in p17M1234. In expression assays (data not shown), p17M1234(731–1081) and p17M1234(731–1424) expressed high levels of $p17^{gag}$ protein. In contrast, p17M1234(731–2165) did not express $p17^{gag}$ protein, indicating the presence of additional INS within the HIV-1 gag coding region. To generate plasmids p17M1234(731–1081) NS, p37M1234 and p55M1234, the stop codon at the end of the altered $p17^{gag}$ gene and all linker sequences in p17M1234 were eliminated by oligonucleotide-directed mutagenesis and the resulting plasmids restored the gag open reading frame as in HIV-1. In expression assays (data not shown) p37M1234 expressed high levels of protein as determined by western blotting and ELISA assays whereas p55M1234 did not express any detectable gag protein. Thus, the addition of sequences 3' to the p24 region resulted in the elimination of protein expression, indicating that nucleotide sequence 1424–2165 contains an INS. This experiment demonstrated that p37M1234 is an appropriate vector to analyze additional INS.

Figure 2:

FIG. 2. Gag expression from the different vectors. (A) HLtat cells were transfected with plasmid p17, p17R, or p17M1234 in the absence (−) or presence (+) of Rev (see infra). The transfected cells were analyzed by immunoblotting using a human HIV-1 patient serum. (B) Plasmid p19 or p19R was transfected into HLtat cells in the absence (−) or presence (+) of Rev. The transfected cells were analyzed by immunoblotting using rabbit and anti-RSV $p19^{gag}$ serum. HIV or RSV proteins served as markers in the same gels. The positions of $p17^{gag}$ and $p19^{gag}$ are indicated at right.

FIG. 3. mRNA analysis on northern blots. (A) HLtat cells were transfected with the indicated plasmids in the absence (−) or presence (+) of Rev. 20 µg of total RNA prepared from the transfected cells were analyzed (see infra). (B) RNA production from plasmid p19 or p19R was similarly analyzed in the absence (−) or presence (+) of Rev. FIG. 4. Nucleotide sequence of the EIV-1 $p17^{gag}$ region. The locations of the 4 oligonucleotides (M1–M4) used to generate all mutants are underlined. The silent nucleotide substitutions introduced by each mutagenesis oligonucleotide are indicated below the coding sequence. Numbering starts from nt +1 of the viral mRNA.

FIG. 5. Gag expression by different mutants. HLtat cells were transfected with the various plasmids indicated at the top of the figure. Plasmid p17R was transfected in the absence (−) or presence (+) of Rev, while the other plasmids were analyzed in the absence of Rev. $p17^{gag}$ production was assayed by immunoblotting as described in FIG. 2.

FIG. 6. Expression vectors used in the identification and elimination of additional INS elements in the gag region. The gag and pol region nucleotides included in each vector are indicated by lines. The position of some gag and pol oligonucleotides is indicated at the top of the figure, as are the coding regions for $p17^{gag}$, $p24^{gag}$, $p15^{gag}$, protease and $p66^{pol}$ proteins. Vector p37M1234 was further mutagenized using different combinations of oligonucleotides. One obtained mutant gave high levels of p24 after expression. It was analyzed by sequencing and found to contain four mutant oligonucleotides M6gag, M7gag, M8gag and M10gag. Other mutants containing different combinations of oligos did not show an increase in expression, or only partial increase in expression. p55BM1-10 and p55AM1-10 were derived from p37M1-10D. p55M1-13P0 contains additional mutations in the gag and pol regions included in the oligonucleotides M11gag, M12gag, M13gag and M0pol. The hatched boxes indicate the location of the mutant oligonucleotides; the hatched boxes containing circles indicate mutated regions containing ATTTA sequences, which may contribute to instability and/or inhibition of the mRNA; and the open boxes containing triangles indicate mutated regions containing AATAAA sequences, which may contribute to instability and/or inhibition of the mRNA. Typical levels of $p24^{gag}$ expression in human cells after transfections as described supra are shown at the-right (in pg/ml).

Figure 7:
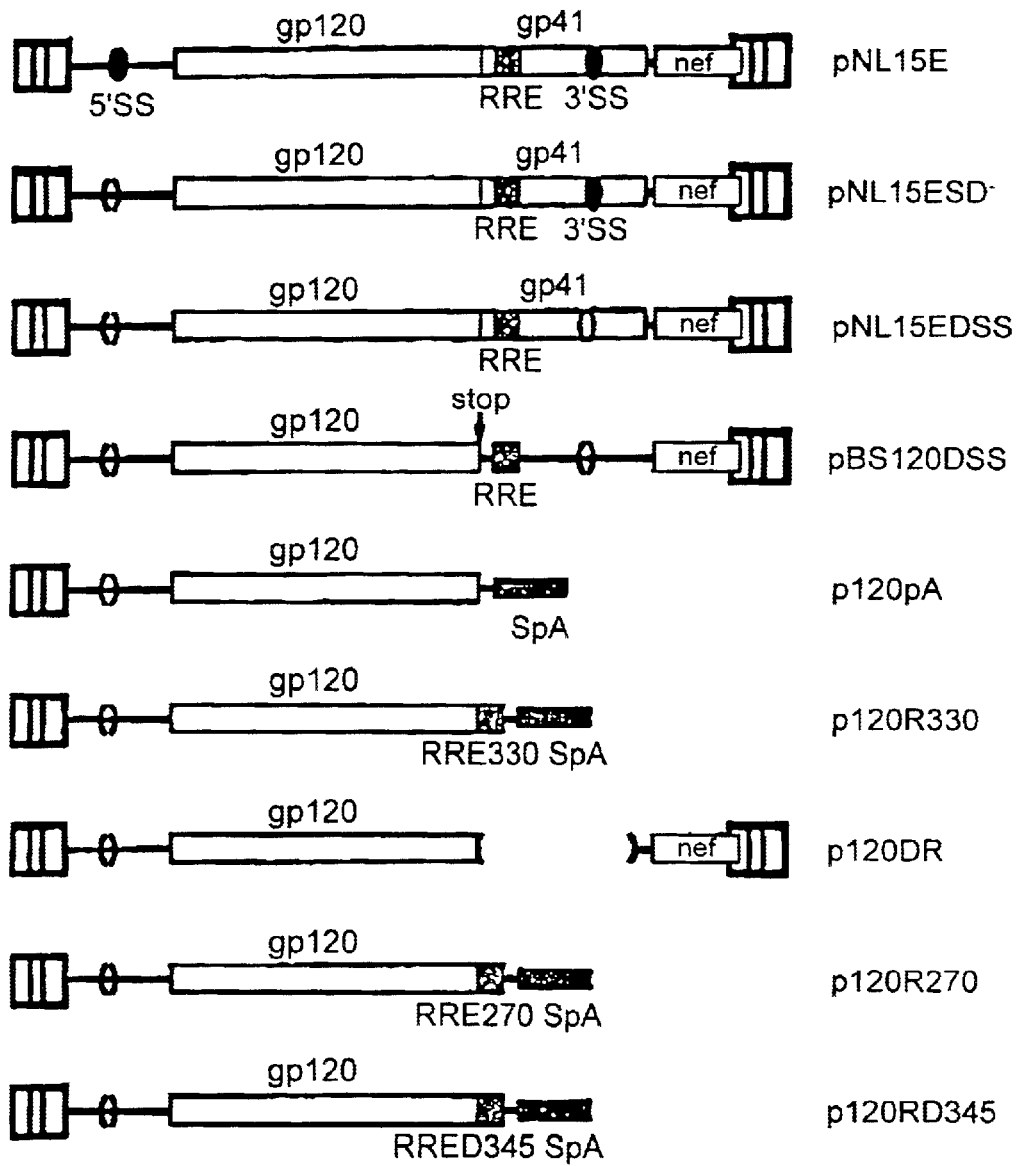

FIG. 7. Eukaryotic expression plasmids used to study env expression. The different expression plasmids are derived from pNL15E (Schwartz, et al. J. Virol. 64:5448–5456 (1990). The generation of the different constructs is described in the text. The numbering follows the corrected HXB2 sequence (Myers et al., 1991, supra; Ratner et al., Hamatol. Bluttransfus. 31:404–406 (1987); Ratner et al., AIDS Res. Hum. Retroviruses 3:57–69 (1987); Solomin, et al. J. Virol. 64:6010–6017 (1990), starting with the first nucleotide of R as +1. 5'SS, 5' splice site; 3'SS, 3' splice site.

FIG. 8. Env expression is Rev dependent in the absence of functional splice sites. Plasmids p15ESD- and p15EDSS (C) were transfected in the absence or presence of a rev expression plasmid (pL3crev) into HLtat cells. One day later, the cells were harvested for analyses of RNA and protein. Total RNA was extracted and analyzed on Northern blots (B). The blots were hybridized with a nick-translated probe spanning XhoI-SacI (nt 8443 to 9118) of HXB2. Protein production was measured by western blots to detect cell-associated Env using a mixture of HIV-1 patient sera and rabbit anti-gp120 antibody (A).

Figure 9A:
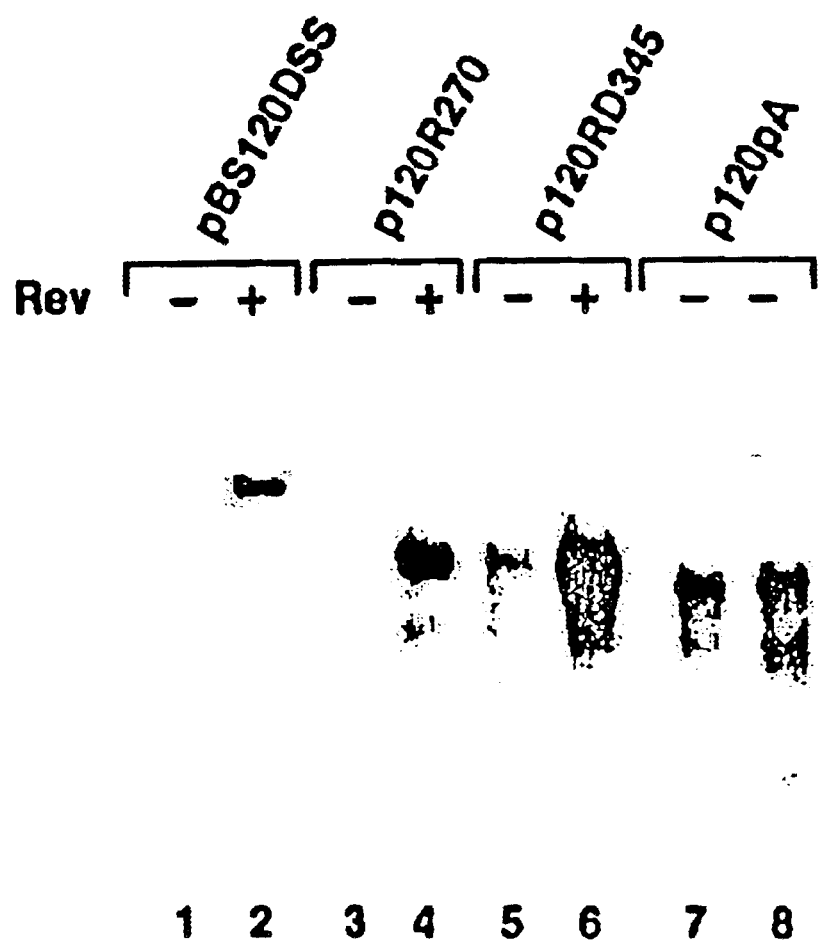

FIG. 9. Env production from the gp120 expression plasmids. The indicated plasmids were transfected into HLtat cells in duplicate plates. A rev expression plasmid (pL3srev) was cotransfected as indicated. One day later, the cells were harvested for analyses of RNA and protein. Total RNA was extracted and analyzed on Northern blots (A). The blots were hybridized using a nick-translated probe spanning nt 6158 to 7924. Protein production (B) was measured by immunoprecipitation after labeling for 5 h with 200 mCi/ml of $^{35}$S-cysteine to detect secreted processed Env (gp120).

Figure 10:
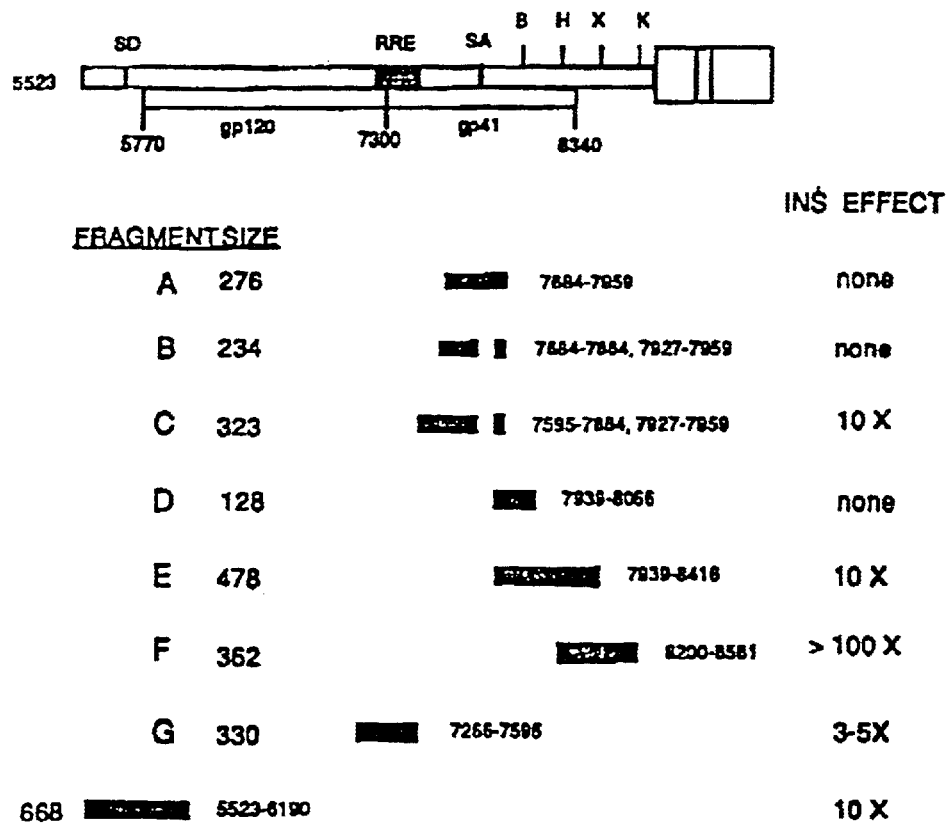

FIG. 10. The identification of INS elements within gp120 and gp41 using the p19 (RSV gag) test system. Schematic structure of exon SE containing the env ORF. Different fragments (A to G) of the gp41 portion and fragment H of the vpu/gp120 portion were PCR amplified and inserted into the unique EcoRI site located downstream of the RSV gag gene in p19. The location of the sequences included in the amplified fragments is indicated to the right using HXB2R numbering system. Fragments A and B are amplified from pNL15E and pNL15EDSS (in which the splice acceptor sites 7A, 7B and 7 have been deleted) respectively, using the same oligonucleotide primers. They are 276 and 234 nucleotides long, respectively. Fragment C was amplified from pNL15EDSS as a 323 nucleotide fragment. Fragment F is a HpaI-KpnI restriction fragment of 362 nucleotides. Fragment E was amplified as a 668 nucleotide fragment from pNL15EDSS, therefore the major splice donor at nucleotide 5592 of HXB2 has been deleted. The rest of the fragments were amplified from PNL15E as indicated in the figure. HLtat cells were transfected with these constructs. One day later, the cells were harvested and p19gag production was determined by Western blot analysis using the anti-RSVGag antibody. The expression of Gag from these plasmids was compared to Gag production of p19. SA, splice acceptor; B, BamHI; H, HpaI; X, XhoI; K, KpnI. The down regulatory effect of INS contained within the different fragments is indicated at right.

Figure 11:
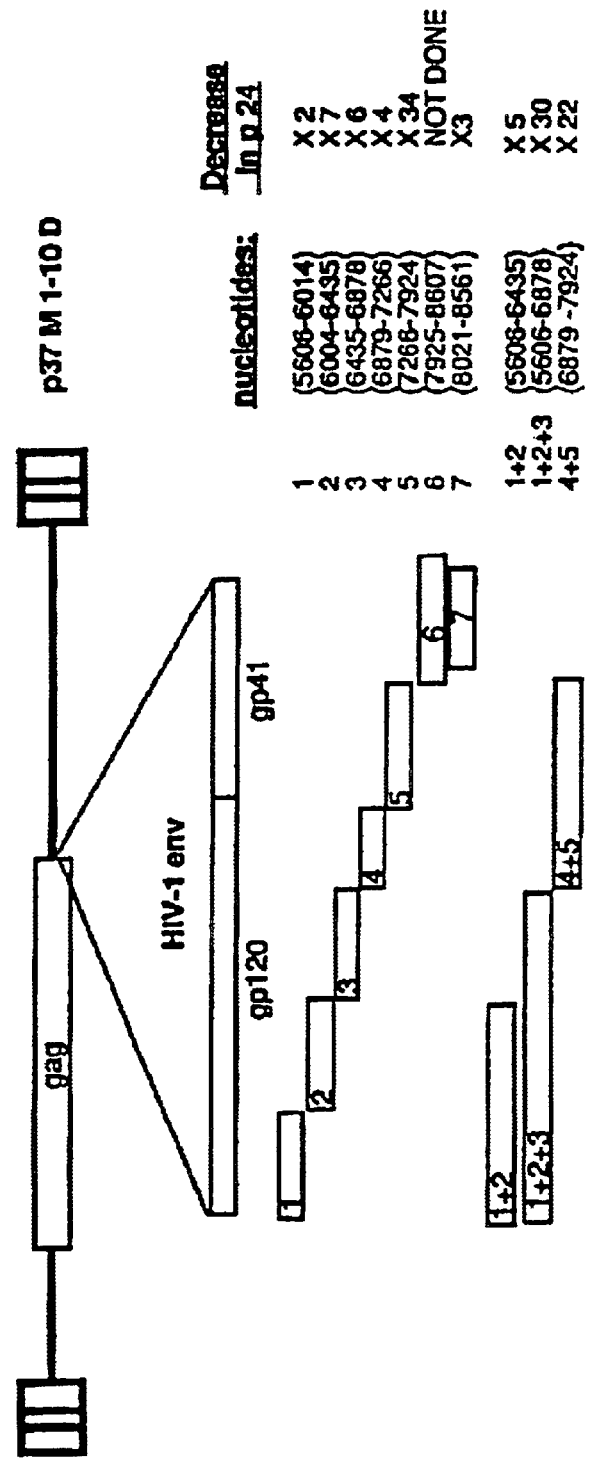

FIG. 11. The identification of INS elements within gp120 and gp41 using the p37M1-10D (mutant INS p37$^{gag}$ expression system) test system. Schematic structure of the env ORF. Different fragments (1 to 7) of env were PCR amplified as indicated in the figure and inserted into the polylinker located downstream of the p37 mutant gag gene in p37M1-10D. Fragments 1 to 6 were amplified from the molecular clone pLW2.4, a gift of Dr. M. Reitz, which is very similar to HXB2R. Clone pLW2.4 was derived from an individual infected by the same HIV-1 strain IIIB, from which the HXB2R molecular clone has been derived. Fragment 7 was cloned from pNL43. For consistency and clarity, the numbering follows the HXB2R system. HLtat cells were transfected with these constructs. One day later, the cells were harvested and p24$^{gag}$ production was determined by antigen capture assay. The expression of Gag from these plasmids was compared to Gag production of p37M1-10D. The down regulatory effect of each fragment is indicated at right.

Figure 12:
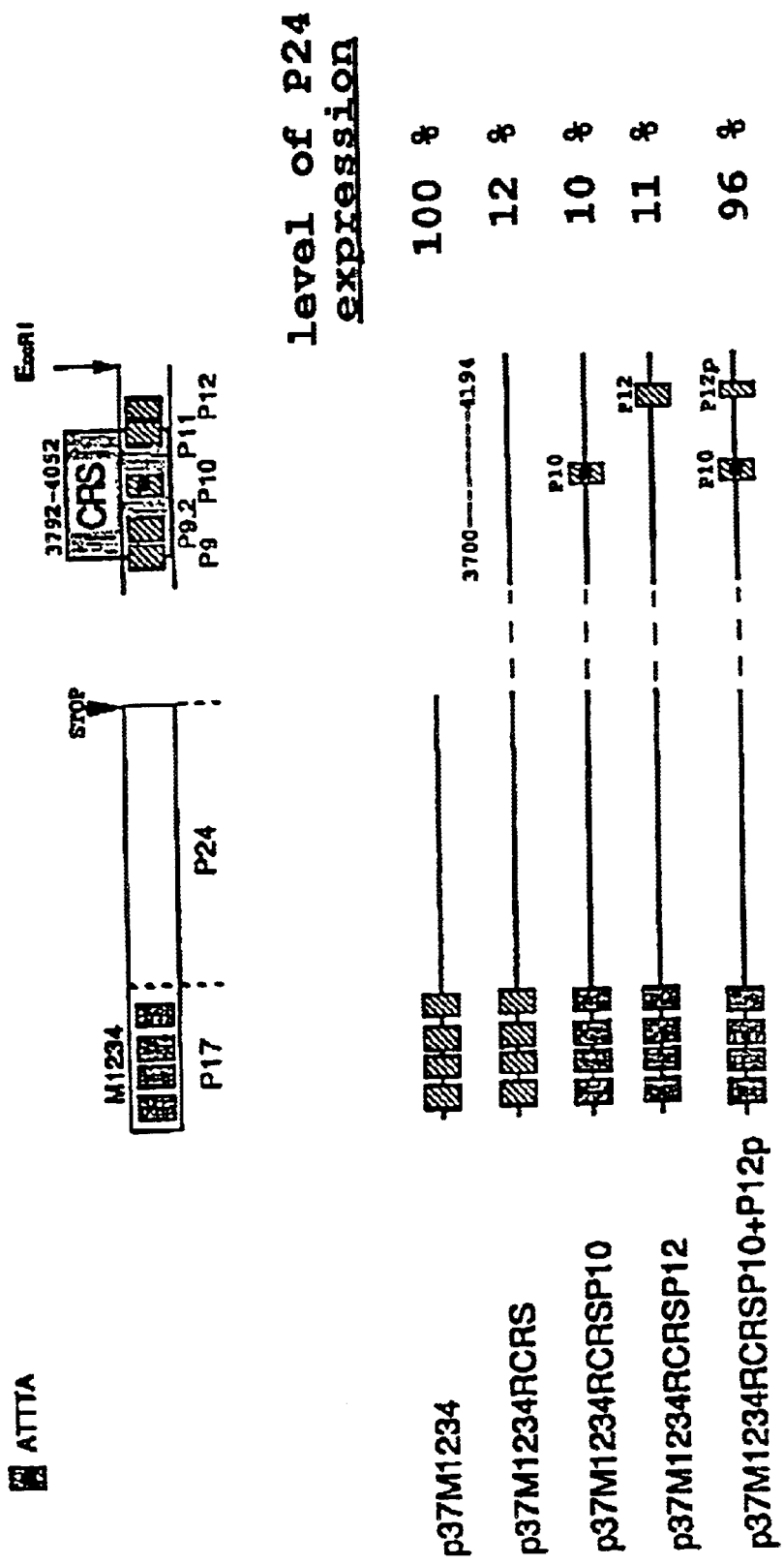

FIG. 12. Elimination of the negative effects of CRS in the pol region. Nucleotides 3700–4194 of HIV-1 were inserted in vector p37M1234 as indicated. This resulted in the inhibition of gag expression. Using mutant oligonucleotides M9pol–M12pol (P9–P12), several mutated CRS clones were isolated and characterized. One of them, p37M1234RCRSP10+P12p contains the mutations indicated in FIG. 13. This clone produced high levels of gag. Therefore, the combination of mutations in p37M1234RCRSP10+P12p eliminated the INS, while mutations only in the region of P10 or of P12 did not eliminate the INS.

FIG. 13. point mutations eliminating the negative effects of CRS in the pol region (nucleotides 3700–4194). The combination of mutations able to completely inactivate the inhibitory/instability element within the CRS region of HIV-1 pol (nucleotides 3700–4194) is shown under the sequence in small letters. These mutations are contained within oligonucleotides M10pol and M12pol (see Table 2). M12pol oligonucleotide contains additional mutations that were not introduced into p37M1234RCRSP10+P12p (see FIG. 12), as determined by DNA sequencing.

Figure 14A:
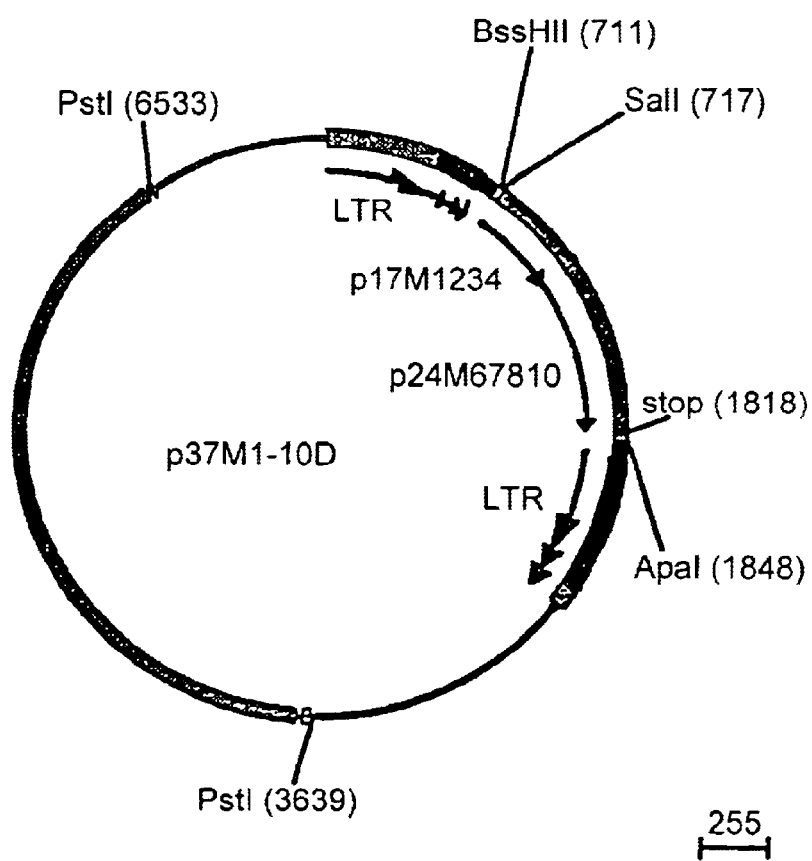

FIG. 14. plasmid map and nucleotide sequence of the efficient gag expression vector p37M1-10D. (A) Plasmid map of vector p37M1-10D. The plasmid contains a pBluescriptKS(-) backbone, human genomic sequences flanking the HIV-1 sequences as found in pNL43 genomic clone, HIV-1 LTRs and the p37$^{gag}$ region (p17 and p24). The p17 region has been mutagenized using oligonucleotides M1 to M4, and the p24 region has been mutagenized using oligonucleotides M6, M7, M8 and M10, as described in the test. The coding region for p37 is flanked by the 5' and 3 HIV-1 LTRs, which provide promoter and polyadenylation signals, as indicated by the arrows. Three consecutive arrows indicate the U5, R, and U3 regions of the LTR, respectively. The transcribed portions of the LTRs are shown in black. The translational stop codon inserted at the end of the p24 coding region is indicated at position 1818. Some restriction endonuclease cleavage sites are also indicated. (B-D) Complete nucleotide sequence of p37M1-10D. The amino acid sequence of the p37$^{gag}$ protein is shown under the coding region. Symbols are as above. Numbering starts at the first nucleotide of the 5' LTR.

V. MODES FOR CARRYING OUT THE INVENTION

It is to be understood that both the foregoing general description and the following detailed description are exemplary and explanatory only, and are not restrictive of the invention, as claimed. The accompanying drawings, which are incorporated in and constitute a part of the specification, illustrate an embodiment of the invention and, together with the description, serve to explain the principles of the invention.

The invention comprises methods for eliminating intragenic inhibitory/instability regions of an mRNA by (a) identifying the intragenic inhibitory/instability regions, and (b) mutating the intragenic inhibitory/instability regions by making multiple point mutations. These mutations may be clustered. This method does not require the identification of the exact location or knowledge of the mechanism of function of the INS. Nonetheless, the results set forth herein allow the conclusion that multiple regions within mRNAs participate in determining stability and utilization and that many of these elements act at the level of RNA transport, turnover, and/or localization. Generally, the mutations are such that the amino acid sequence encoded by the mRNA is unchanged, although conservative and non-conservative amino acid substitutions are also envisioned as part of the invention where the protein encoded by the mutated gene is substantially similar to the protein encoded by the non-mutated gene.

The nucleotides to be altered can be chosen randomly, the only requirement being that the amino acid sequence encoded by the protein remain unchanged; or, if conservative and non-conservative amino acid substitutions are to be made, the only-requirement is that the protein encoded by the mutated gene be substantially similar to the protein encoded by the non-mutated gene.

If the INS region is AT rich or GC rich, it is preferable that it be altered so that it has a content of about 50% G and C and about 50% A and T. If the INS region contains less-preferred codons, it is preferable that those be altered to more-preferred codons. If desired, however (e.g., to make an A and T rich region more G and C rich), more-preferred codons can be altered to less-preferred codons. If the INS region contains conserved nucleotides, some of those conserved nucleotides could be altered to non-conserved nucleotides. Again, the only requirement is that the amino acid sequence encoded by the protein remain unchanged; or, if conservative and non-conservative amino acid substitutions are to be made, the only requirement is that the protein encoded by the mutated gene be substantially similar to the protein encoded by the non-mutated gene.

As used herein, conserved nucleotides means evolutionarily conserved nucleotides for a given gene, since this conservation may reflect the fact that they are part of a signal involved in the inhibitory/instability determination. Conserved nucleotides can generally be determined from published references about the gene of interest or can be determined by using a variety of computer programs available to practitioners of the art.

Less-preferred and more-preferred codons for various organisms can be determined from codon usage charts, such as those set forth in T. Maruyama et al., Nucl. Acids Res. 14:r151–r197 (1986) and in S. Aota et al., Nucl. Acids. Res. 16:r315–r402 (1988), or through use of a computer program, such as that disclosed in U.S. Pat. No. 5,082,767 entitled "Codon Pair Utilization", issued to G. W. Hatfield et al. on Jan. 21, 1992, which is incorporated herein by reference.

Generally, the method of the invention is carried out as follows:
1. Identification of an mRNA Containing an INS The rate at which a particular protein is made is usually proportional to the cytoplasmic level of the mRNA which encodes it. Thus, a candidate for an mRNA containing an inhibitory/instability sequence is one whose mRNA or protein is either not detectably expressed or is expressed poorly as compared to the level of expression of a reference mRNA or protein under the control of the same or similar strength promoter. Differences in the steady state levels of a particular mRNA (as determined, for example, by Northern blotting), when compared to the steady state level of mRNA from another gene under the control of the same or similar strength promoter, which cannot be accounted for by changes in the apparent rate of transcription (as determined, for example, by nuclear run-on assays) indicate that the gene is a candidate for an unstable mRNA. In addition or as an alternative to being unstable, cytoplasmic mRNAs may be poorly utilized due to various inhibitory mechanisms acting in the cytoplasm. These effects may be mediated by specific mRNA sequences which are named herein as "inhibitory sequences".

Candidate mRNAs containing inhibitory/instability regions include mRNAs from genes whose expression is tightly regulated, e.g., many oncogenes, growth factor genes and genes for biological response modifiers such as interleukins. Many of these genes are expressed at very low levels, decay rapidly and are modulated quickly and transiently under different conditions. The negative regulation of expression at the level of mRNA stability and utilization has been documented in several cases and has been proposed to be occurring in many other cases. Examples of genes for which there is evidence for post-transcriptional regulation due to the presence of inhibitory/instability regions in the mRNA include the cellular genes encoding granulocyte-monocyte colony stimulating factor (GM-CSF), proto-oncogenes c-myc, c-myb, c-sis, c-fos; interferons (alpha, beta and gamma IFNs); interleukins (IL1, IL2 and IL3); tumor necrosis factor (TNF); lymphotoxin (Lym); IgG1 induction factor (IgG IF); granulocyte colony stimulating factor (G-CSF); transferrin receptor (TfR); and galactosyltransferase-associated protein (GTA); HIV-1 genes encoding env, gag and pol; the *E. coli* genes for 6-phosphogluconate dehydrogenase (gnd) and btuB; and the yeast gene for MATα1 (see the discussion in the "Background Art" section, above). The genes encoding the cellular proto-oncogenes c-myc and c-fos, as well as the yeast gene for MATα1 and the HIV-1 genes for gag, env and pol are genes for which there is evidence for inhibitory/instability regions within the coding region in addition to evidence for inhibitory/instability regions within the non-coding region. Genes encoding or suspected of encoding mRNAs containing inhibitory/instability regions within the coding region are particularly relevant to the invention.

After identifying a candidate unstable or poorly utilized mRNA, the in vivo half-life (or stability) of that mRNA can be studied by conducting pulse-chase experiments (i.e., labeling newly synthesized RNAs with a radioactive precursor and monitoring the decay of the radiolabeled mRNA in the absence of label); or by introducing in vitro transcribed mRNA into target cells (either by microinjection, calcium phosphate co-precipitation, electroporation, or other methods known in the art) to monitor the in vivo half-life of the defined mRNA population; or by expressing the mRNA under study from a promoter which can be induced and which shuts off transcription soon after induction, and estimating the half-life of the mRNA which was synthesized during this short transcriptional burst; or by blocking transcription pharmacologically (e.g., with Actinomycin D) and following the decay of the particular mRNA at various time points after the addition of the drug by Northern blotting or RNA protection (e.g. S1 nuclease) assays. Methods for all the above determinations are well established. See, e.g., M. W. Hentze et al., Biochim. Biophys. Acta 1090:281–292 (1991) and references cited therein. See also, S. Schwartz et al., J. Virol. 66:150–159 (1992). The most useful measurement is how much protein is produced, because this includes all possible INS mechanisms. Examples of various mRNAs which have been shown to contain or which are suspected to contain INS regions are described above. Some of these mRNAs have been shown to have half-lives of less than 30 minutes when their mRNA levels are measured by Northern blots (see, e.g., D. Wreschner and G. Rechavi, Eur. J. Biochem. 172:333–340 (1988)).

2. Localization of Instability Determinants

When an unstable or poorly utilized mRNA has been identified, the next step is to search for the responsible (cis-acting) RNA sequence elements. Detailed methods for localizing the cis-acting inhibitory/instability regions are set forth in each of the references described in the "Background Art" section, above, and are also discussed infra. The exemplified constructs of the present invention can also be used to localize INS (see below). Cis acting sequences responsible for specific mRNA turnover can be identified by deletion and point mutagenesis as well as by the occasional identification of naturally occurring mutants with an altered mRNA stability.

In short, to evaluate whether putative regulatory sequences are sufficient to confer mRNA stability control, DNA sequences coding for the suspected INS regions are fused to an indicator (or reporter) gene to create a gene coding for a hybrid mRNA. The DNA sequences fused to the indicator (or reporter) gene can be cDNA, genomic DNA or synthesized DNA. Examples of indicator (or reporter) genes that are described in the references set forth in the "Background Art" section include the genes for neomycin, β-galactosidase, chloramphenicol acetyltransferase (CAT), and luciferase, as well as the genes for β-globin, PGK1 and ACT1. See also Sambrook et al., *Molecular Cloning, A Laboratory Manual*, 2d. ed. Cold Spring Harbor Laboratory, Cold Spring Harbor, N.Y., (1989), pp. 16.56–16.67. Other genes which can be used as indicator genes are disclosed herein (i.e., the gag gene of the Rous Sarcoma Virus (which lacks an inhibitory/instability region) and the Rev independent HIV-1 gag genes of constructs p17M1234, p37M1234 and p37M1-10D, which have been mutated to inactivate the inhibitory/instability region and which constitute one aspect of the invention. In general, virtually any gene encoding a mRNA which is stable or which is expressed at relatively high levels (defined here as being stable enough or expressed at high enough level so that any decrease in the level of the mRNA or expressed protein can be detected by standard methods) can be used as an indicator or reporter gene, although the constructs p37M1234 and p37M1-10D, which are exemplified herein, are preferred for reasons set forth below. Preferred methods of creating hybrid genes using these constructs and testing the expression of mRNA and protein from these constructs are also set forth below.

In general, the stability and/or utilization of the mRNAs generated by the indicator gene and the hybrid genes consisting of the indicator gene fused to the sequences suspected of encoding an INS region are tested by transfecting the hybrid genes into host cells which are appropriate for the expression vector used to clone and express the mRNAs. The resulting levels of mRNA are determined by standard methods of determining mRNA stability, e.g. Northern blots, S1 mapping or PCR methods, and the resulting levels of protein produced are quantitated by protein measuring assays, such as ELISA, immunoprecipitation and/or western blots. The inhibitory/instability region (or regions, if there are more than one) will be identified by a decrease in the protein expression and/or stability of the hybrid mRNA as compared to the control indicator mRNA. Note that if the ultimate goal is to increase production of the encoded protein, the identification of the INS is most preferably carried out in the same host cell as will be used for the production of the protein.

Examples of some of the host cells that have been used to detect INS sequences include somatic mammalian cells, Xenopus oocytes, yeast and *E. coli*. See, e.g., G. Shaw and R. Kamen, Cell 46:659–667 (1986) (discussed supra) which localized instability sequences in GM-CSF by inserting putative inhibitory sequences into the 3' UTR of the β-globin gene, causing the otherwise stable β-globin mRNA to become unstable when transfected into mouse or human cells. See also I. Laird-Offringa et al., Nucleic Acids Res. 19:2387–2394 (1991) which localized inhibitory/instability sequences in c-myc using hybrid c-myc-neomycin resistance genes introduced into rat fibroblasts, and M. Lundigran et al., Proc. Natl. Acad. Sci. USA 88:1479–1483 (1991) which localized inhibitory/instability sequences in btuB gene by using hybrid btuB-lacZ genes introduced into *E. coli*. For examples of reported localization of specific inhibitory/instability sequences within a transcript of HIV-1 by destabilization of an otherwise long-lived indicator transcript, see, e.g., M. Emerman, Cell 57:1155–1165 (1989) (replaced 3' UTR of env gene with part of HBV and introduced into COS-1 cells); S. Schwartz et al., J. Virol. 66:150–159 (1992) (gag gene fusions with Rev independent tat reporter gene introduced into HeLa cells); F. Maldarelli et al., J. Virol. 65:5732–5743 (1991) (gag/pol gene fusions with Rev independent tat reporter gene or chloramphenicol acetyltransferase (CAT) gene introduced into HeLa and SW480 cells); and A. Cochrane et al., J. Virol. 65:5303–5313 (1991) (pol gene fusions with CAT gene or rat proinsulin gene introduced into COS-1 and CHO cells).

It is anticipated that in vitro mRNA degradation systems (e.g., crude cytoplasmic extracts) to assay mRNA turnover in vitro will complement ongoing in vivo analyses and help to circumvent some of the limitations of the in vivo systems. See M. W. Hentze et al., Biochim. Biophys. Acta 1090:281–292 (1991) and references cited therein. See also D. Wreschner and G. Rechavi, Eur. J. Biochem. 172:333–340 (1988), which analyzed exogenous mRNA stability in a reticulocyte lysate cell-free system.

In the method of the invention, the whole gene of interest may be fused to an indicator or reporter gene and tested for its effect on the resulting hybrid mRNA in order to determine whether that gene contains an inhibitory/instability region or regions. To further localize the INS within the gene of interest, fragments of the gene of interest may be prepared by sequentially deleting sequences from the gene of interest from either the 5' or 3' ends or both. The gene of interest may also be separated into overlapping fragments by methods known in the art (e.g., with restriction endonucleases, etc.) See, e.g., S. Schwartz et al., J. Virol. 66:150–159 (1992). Preferably, the gene is separated into overlapping fragments about 300 to 2000 nucleotides in length. Two types of vector constructs can be made. To permit the detection of inhibitory/instability regions that do not need to be translated in order to function, vectors can be constructed in which the gene of interest (or its fragments or suspected INS) can be inserted into the 3' UTR downstream from the stop codon of an indicator or reporter gene. This does not permit translation through the INS. To test the possibility that some inhibitory/instability sequences may act only after translation of the mRNA, vectors can be constructed in which the gene of interest (or its fragments or suspected INS) is inserted into the coding region of the indicator/reporter gene. This method will permit the detection of inhibitory/instability regions that do need to be translated in order to function. The hybrid constructs are transfected into host cells, and the resulting mRNA levels are determined by standard methods of determining mRNA stability, e.g.

Northern blots, S1 mapping or PCR methods, as set forth above and as described in most of the references cited in the "Background Art" section. See also, Sambrook et al. (1989), supra, for experimental methods. The protein produced from such genes is also easily quantitated by existing assays, such as ELISAS, immunoprecipitation and western blots, which are also described in most of the references cited in the "Background Art" section. See also, Sambrook et al. (1989), supra, for experimental methods. The hybrid DNAs containing the inhibitory/instability region (or regions, if there are more than one) will be identified by a decrease in the protein expression and/or stability of the hybrid mRNA as compared to the control indicator mRNA. The use of various fragments of the gene permits the identification of multiple independently functional inhibitory/instability regions, if any, while the use of overlapping fragments lessen the possibility that an inhibitory/instability region will not be identified as a result of its being cut in half, for example.

The exemplified test vectors set forth in FIG. 1.(B) and FIG. 6 and described herein, e.g., vectors p17M1234, p37M1234, P37M1-10D and p19, can be used to assay for the presence and location of INS in various RNAs, including INS which are located within coding regions. These vectors can also be used to determine whether a gene of interest not yet characterized has INS which are candidates for mutagenesis curing. These vectors have a particular advantage over the prior art in that the same vectors can be used in the mutagenesis step of the invention (described below) in which the identified INS is eliminated without affecting the coding capacity of the gene.

The method of using these vectors involves introducing the entire gene, entire cDNA or fragments of the gene ranging from approximately 300 nucleotides to approximately 2 kilobases 3' to the coding region for gag protein using unique restriction sites which are engineered into the vectors. The expression of the gag gene in HLtat cells is measured at both the RNA and protein levels, and compared to the expression of the starting vectors. A decrease in expression indicates the presence of INS candidates that may be cured by mutagenesis. The method of using the vectors exemplified in FIG. 1 herein involves introducing the entire gene and fragments of the gene of interest into vectors p17M1234, p37M1234 and p19. The size of the fragments are preferably 300–2000 nucleotides long. Plasmid DNA is prepared in *E. coli* and purified by the CsCl method.

To permit detection of inhibitory/instability regions which do not need to be translated in order to function, the entire gene and fragments of the gene of interest are introduced into vectors p17M1234, p37M1234 or p19 3' of the stop codon of the p17$^{gag}$ coding region. To allow the detection of inhibitory/instability regions that affect expression only when translated, the described vectors can be manipulated so that the coding region of the entire gene or fragments of the gene of interest are fused in frame to the expressed gag protein gene. For example, a fragment containing all or part of the coding region of the gene of interest can be inserted exactly 3' to the termination codon of the gag coding sequence in vector p37M1234 and the termination codon of gag and the linker sequences can be removed by oligonucleotide mutagenesis in such a way as to fuse the gag reading frame to the reading frame of the gene of interest.

RNA and protein production from the two expression vectors (e.g. p37M1234 containing the, fragment of the gene of interest inserted directly 3' of the stop codon of the gag coding region, with the gag termination codon intact, and p37M1234 containing the fragment of the gene of interest inserted in frame with the gag coding region, with the gag termination codon deleted) are then compared after transfection of purified DNA into HLtat cells.

The expression of these vectors after transfection into human cells is monitored at both the level of RNA and protein production. RNA levels are guantitated by, e.g., Northern blots, S1 mapping or PCR methods. Protein levels are quantitated by, e.g., western blot or ELISA methods. p37M1234 and p37M1-10D are ideal for quantitative analysis because a fast non-radioactive ELISA protocol can be used to detect gag protein (DUPONT or COULTER gag antigen capture assay). A decrease in the level of expression of the gag antigen indicates the presence of inhibitory/instability regions within the cloned gene or fragment of the gene of interest.

After the inhibitory/instability regions have been identified, the vectors containing the appropriate INS fragments can be used to prepare single-stranded DNA and then used in mutagenesis experiments with specific chemically synthesized oligonucleotides in the clustered mutagenesis protocol described below.

3. Mutation of the Inhibitory/Instability Regions to Generate Stable mRNAs

Once the inhibitory/instability sequences are located within the coding region of an mRNA, the gene is modified to remove these inhibitory/instability sequences without altering the coding capacity of the gene. Alternatively, the gene is modified to remove the inhibitory/instability sequences, simultaneously altering the coding capacity of the gene to encode either conservative or non-conservative amino acid substitutions.

In the method of the invention, the most general method of eliminating the INS in the coding region of the gene of interest is by making multiple mutations in the INS region of the gene or gene fragments, without changing the amino acid sequence of the protein encoded by the gene; or, if conservative and non-conservative amino acid substitutions are to be made, the only requirement is that the protein encoded by the mutated gene be substantially similar to the protein encoded by the non-mutated gene. It is preferred that all of the suspected inhibitory/instability regions, if more than one, be mutated at once. Later, if desired, each inhibitory/instability region can be mutated separately in order to determine the smallest region of the gene that needs to be mutated in order to generate a stable mRNA. The ability to mutagenize long DNA regions at the same time can decrease the time and effort needed to produce the desired stable and/or highly expressed mRNA and resulting protein. The altered gene or gene fragments containing these mutations will then be tested in the usual manner, as described above, e.g., by fusing the altered gene or gene fragment with a reporter or indicator gene and analyzing the level of mRNA and protein produced by the altered genes after transfection into an appropriate host cell. If the level of mRNA and protein produced by the hybrid gene containing the altered gene or gene fragment is about-the same as that produced by the control construct encoding only the indicator gene, then the inhibitory/instability regions have been effectively eliminated from the gene or gene fragment due to the alterations made in the INS.

In the method of the invention, more than two point mutations will be made in the INS region. Optionally, point mutations may be made in at least about 10% of the nucleotides in the inhibitory/instability region. These point mutations may also be clustered. The nucleotides to be altered can be chosen randomly (i.e., not chosen because of AT or GC content or the presence or absence of rare or preferred codons), the only requirement being that the amino acid sequence encoded by the protein remain unchanged; or, if conservative and non-conservative amino acid substitutions are to be made, the only requirement is that the protein encoded by the mutated gene be substantially similar to the protein encoded by the non-mutated gene.

In the method of the present invention, the gene sequence can be mutated so that the encoded protein remains the same due to the fact that the genetic code is degenerate, i.e., many of the amino acids may be encoded by more than one codon. The base code for serine, for example, is six-way degenerate such that the codons TCT, TCG, TCC, TCA, AGT, and AGC all code for serine. Similarly, threonine is encoded by any one of codons ACT, ACA, ACC and ACG. Thus, a plurality of different DNA sequences can be used to code for a particular set of amino acids. The codons encoding the other amino acids are TTT and TTC for phenylalanine; TTA, TTG, CTT, CTC, CTA and CTG for leucine; ATT, ATC and ATA for isoleucine; ATG for methione; GTT, GTC, GTA and GTG for valine; CCT, CCC, CCA and CCG for proline; GCU, GCC, GCA and GCG for alanine; TAT and TAC for tyrosine; CAT and CAC for histidine; CAA and CAG for glutamine; AAT and AAC for asparagine; AAA and AAG for lysine; GAT and GAC for aspartic acid; GAA and GAG for glutamic acid; TGT and TGC for cysteine; TGG for tryptophan; CGT, CGC, CGA and CGG for arginine; and GGU, GGC, GGA and GGG for glycine. Charts depicting the codons (i.e., the genetic code) can be found in various general biology or biochemistry textbooks.

In the method of the present invention, if the portion(s) of the gene encoding the inhibitory/instability regions are AT-rich, it is preferred, but not believed to be necessary, that most or all of the mutations in the inhibitory/instability region be the replacement of A and T with G and C nucleotides, making the regions more GC-rich, while still maintaining the coding capacity of the gene. If the portion(s) of the gene encoding the inhibitory/instability regions are GC-rich, it is preferred, but not believed to be necessary, that most or all of the mutations in the inhibitory/instability region be the replacement of G and C nucleotides with A and T nucleotides, making the regions less GC-rich, while still maintaining the coding capacity of the gene. If the INS region is either AT-rich or GC-rich, it is most preferred that it be altered so that it has a content of about 50% G and C and about 50% A and T. The AT- (or AU-) content (or, alternatively, the GC-content) of an inhibitory/instability region or regions can be calculated by using a computer program designed to make such calculations. Examples of such programs, used to determine the AT-richness of the HIV-1 gag inhibitory/instability regions exemplified herein, are the GCG Analysis Package for the VAX (University of Wisconsin) and the Gene Works Package (Intelligenetics).

In the method of the invention, if the INS region contains less-preferred codons, it is preferable that those be altered to more-preferred codons. If desired, however (e.g., to make an AT-rich region more GC-rich), more-preferred codons can be altered to less-preferred codons. It is also preferred, but not believed to be necessary, that less-preferred or rarely used codons be replaced with more-preferred codons. Optionally, only the most rarely used codons (identified from published codon usage tables, such as in T. Maruyama et al., Nucl. Acids Res. 14(Supp):r151–197 (1986)) can be replaced with preferred codons, or alternatively, most or all of the rare codons can be replaced with preferred codons. Generally, the choice of preferred codons to use will depend on the codon usage of the host cell in which the altered gene is to be expressed. Note, however, that the substitution of more-preferred codons with less-preferred codons is also functional, as shown in the example below.

As noted above, coding sequences are chosen on the basis of the genetic code and, preferably on the preferred codon usage in the host cell or organism in which the mutated gene of this invention is to be expressed. In a number of cases the preferred codon usage of a particular host or expression system can be ascertained from available references (see, e.g., T. Maruyama et al., Nucl. Acids Res. 14(Supp) :r151–197 (1986)), or can be ascertained by other methods (see, e.g., U.S. Pat. No. 5,082,767 entitled "Codon Pair Utilization", issued to G. W. Hatfield et al. on Jan. 21, 1992, which is incorporated herein by reference). Preferably, sequences will be chosen to optimize transcription and translation as well as mRNA stability so as to ultimately increase the amount of protein produced. Selection of codons is thus, for example, guided by the preferred use of codons by the host cell and/or the need to provide for desired restriction endonuclease sites and could also be guided by a desire to avoid potential secondary structure constraints in the encoded mRNA transcript. Potential secondary structure constraints can be identified by the use of computer programs such as the one described in M. Zucker et al., Nucl. Acids Res. 9:133 (1981). More than one coding sequence may be chosen in situations where the codon preference is unknown or ambiguous for optimum codon usage in the chosen host cell or organism. However, any correct set of codons would encode the desired protein, even if translated with less than optimum efficiency.

In the method of the invention, if the INS region contains conserved nucleotides, it is also preferred, but not believed to be necessary, that conserved nucleotides sequences in the inhibitory/instability region be mutated. Optionally, at least approximately 75% of the mutations made in the inhibitory/ instability region may involve the mutation of conserved nucleotides. Conserved nucleotides can be determined by using a variety of computer programs available to practitioners of the art.

In the method of the invention, it is also anticipated that inhibitory/instability sequences can be mutated such that the encoded amino acids are changed to contain one or more conservative or non-conservative amino acids yet still provide for a functionally equivalent protein. For example, one or more amino acid residues within the sequence can be substituted by another amino acid of a similar polarity which acts as a functional equivalent, resulting in a neutral substitution in the amino acid sequence. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

In the exemplified method of the present invention, all of the regions in the HIV-1 gag gene suspected to have inhibitory/instability activity were first mutated at once over a region approximately 270 nucleotides in length using clustered site-directed mutagenesis with four different oligonucleotides spanning a region of approximately 300 nucleotides to generate the construct p17M1234, described infra, which encodes a stable mRNA.

The four oligonucleotides, which are depicted in FIG. 4, are

M1:
ccaggggggaaagaagaagtacaagctaaagcacatcgtatgggcaagcagg  (SEQ ID NO:6);

M2:
ccttcagacaggatcagaggagcttcgatcactatacaacacagtagc  (SEQ ID NO:7);

M3:
accctctattgtgtgcaccagcggatcgagatcaaggacaccaaggaagc  (SEQ ID NO:8); and

M4:
gagcaaaacaagtccaagaagaaggcccagcaggcagcagctgacacagg  (SEQ ID NO:9).

These oligonucleotides are 51 (M1), 48 (M2), 50 (M3) and 50 (M4) nucleotides in length. Each oligonucleotide introduced several point mutations over an area of 19–22 nucleotides (see infra). The number of nucleotides 5' to the first mutated nucleotide were 14 (M1); 18 (M2); 17 (M3); and 11 (M4); and the number of nucleotides 3' to the last mutated nucleotide were 15 (M1); 8 (M2); 14 (M3); and 17 (M4). The ratios of AT to GC nucleotides present in each of these regions before mutation was 33AT/18GC (M1); 30AT/18GC (M2); 29AT/21GC (M3) and 27AT/23GC (M4). The ratios of AT to GC nucleotides present in each of these regions after mutation was 25AT/26GC (M1); 24AT/24GC (M2); 23AT/27GC (M3) and 22AT/28GC (M4). A total of 26 codons were changed. The number of times the codon appears in human genes per 1000 codons (from T. Maruyama et al., Nuc. Acids Res. 14 (Supp.):r151–r197 (1986)) is listed in parentheses next to the codon. In the example, 8 codons encoding lysine (Lys) were changed from aaa (22.0) to aag (35.8); two codons encoding tyrosine (Tyr) were changed from tat (12.4) to tac (18.4); two codons encoding leucine (Leu) were changed from tta (5.9) to cta (6.1); two codons encoding histidine (His) were changed from cat (9.8) to cac (14.3); three codons encoding isoleucine (Ile) were changed from ata (5.1) to atc (24.0); two codons encoding glutamic acid (Glu) were changed from gaa (26.8) to gag (41.6); one codon encoding arginine (Arg) was changed from aga (10.8) to cga (5.2) and one codon encoding arginine (Arg) was changed from agg (11.4) to cgg (7.7); one codon encoding asparagine (Asn) was changed from aat (16.9) to aac (23.6); two codons encoding glutamine (Gln) were changed from caa (11.5) to cag (32.7); one codon encoding serine (Ser) was changed from agt (8.7) to tcc (18.7); and one codon encoding alanine (Ala) was changed from gca (12.7) to gcc (29.8).

The techniques of oligonucleotide-directed site-specific mutagenesis employed to effect the modifications in structure or sequence of the DNA molecule are known to those of skill in the art. The target DNA sequences which are to be mutagenized can be cDNA, genomic DNA or synthesized DNA sequences. Generally, these DNA sequences are cloned into an appropriate vector, e.g., a bacteriophage M13 vector, and single-stranded template DNA is prepared from a plaque generated by the recombinant bacteriophage. The single-stranded DNA is annealed to the synthetic oligonucleotides and the mutagenesis and subsequent steps are performed by methods well known in the art. See, e.g., M. Smith and S. Gillam, in *Genetic Engineering: Principles and Methods*, Plenum Press 3:1–32 (1981) (review) and T. Kunkel, Proc. Natl. Acad. Sci. USA 82:488–492 (1985). See also, Sambrook et al. (1989), supra. The synthetic oligonucleotides can be synthesized on a DNA synthesizer (e.g., Applied Biosystems) and purified by electrophoresis by methods known in the art. The length of the selected or prepared oligodeoxynucleotides using this method can vary. There are no absolute size limits. As a matter of convenience, for use in the process of this invention, the shortest length of the oligodeoxynucleotide is generally approximately 20 nucleotides and the longest length is generally approximately 60 to 100 nucleotides. The size of the oligonucleotide primers are determined by the requirement for stable hybridization of the primers to the regions of the gene in which the mutations are to be induced, and by the limitations of the currently available methods for synthesizing oligonucleotides. The factors to be considered in designing oligonucleotides for use in oligonucleotide-directed mutagenesis (e.g., overall size, size of portions flanking the mutation(s)) are described by M. Smith and S. Gillam in *Genetic Engineering: Principles and Methods*, Plenum Press 3:1–32 (1981). In general, the overall length of the oligonucleotide will be such as to optimize stable, unique hybridization at the mutation site with the 5' and 3' extensions from the mutation site being of sufficient size to avoid editing of the mutation(s) by the exonuclease activity of the DNA polymerase. Oligonucleotides used for mutagenesis in the present invention will generally be at least about 20 nucleotides, usually about 40 to 60 nucleotides in length and usually will not exceed about 100 nucleotides in length. The oligonucleotides will usually contain at least about five bases 3' of the altered codons.

In the preferred mutagenesis protocol of the present invention, the INS containing expression vectors contain the BLUESCRIPT plasmid vector as a backbone. This enables the preparation of double-stranded as well as single-stranded DNA. Single-stranded uracil containing DNA is prepared according to a standard protocol as follows: The plasmid is transformed into a F' bacterial strain (e.g. DH5aF'). A colony is grown and infected with the helper phage M13-VCS [Stratagene #20025; 1×10$^{11}$ pfu/ml]. This phage is used to infect a culture of the *E. coli* strain CJ236 and single-stranded DNA is isolated according to standard methods. 0.25 ug of single-stranded DNA is annealed with the synthesized oligonucleotides (5 ul of each oligo, dissolved at a concentration of 5 OD$_{260}$/ml. The synthesized oligonucleotides are usually about 40 to 60 nucleotides in length and are designed to contain a perfect match of approximately 10 nucleotides at each end. They may contain as many changes as desired within the remaining 20–40 nucleotides. The oligonucleotides are designed to cover the region of interest and they may be next to each other or there may be gaps between them. Up to six different oligonucleotides have been used at the same time, although it is believed that the use of more than six oligonucleotides at the same time would also work in the method of this invention. After annealing, elongation with T4 polymerase produces the second strand which does not contain uracil. The free ends are ligated using ligase. This results in double-stranded DNA which can be used to transform *E. coli* strain HB101. The mutated strand which does not contain uracil produces double-stranded DNA, which contains the introduced mutations. Individual colonies are picked and the mutations are quickly verified by sequence analysis. Alternatively or additionally, this mutagenesis method can (and has been) used to select for different combinations of oligonucleotides which result in different mutant phenotypes. This facilitates the analysis of the regions important for function and is helpful in subsequent experiments because it allows the analysis of exact sequences involved in the INS. In addition to the exemplified mutagenesis of the INS-1 region of HIV-1 described herein, this method has also been used to mutate in one step a region of 150 nucleotides using three tandemly arranged oligonucleotides that introduced a total of 35 mutations. The upper limit of changes is not clear, but it is estimated that regions of approximately 500 nucleotides can be changed in 20% of their nucleotides in one step using this protocol.

The exemplified method of mutating by using oligonucleotide-directed site-specific mutagenesis may be varied by using other methods known in the art. For example, the mutated gene can be synthesized directly using overlapping synthetic deoxynucleotides (see, e.g., Edge et al., Nature 292:756 (1981); Nambair et al., Science 223:1299 (1984); Jay et al., J. Biol. Chem. 259:6311 (1984); or by using a combination of polymerase chain reaction generated DNAs or cDNAs and synthesized oligonucleotides.

4. Determination of Stability of the Mutated mRNA

The steady state level and/or stability of the resultant mutated mRNAs can be tested in the same manner as the steady state level and/or stability of the unmodified mRNA containing the inhibitory/instability regions are tested (e.g., by Northern blotting), as discussed in section 1, above. The mutated mRNA can be analyzed along with (and thus compared to) the unmodified mRNA containing the inhibitory/instability region(s) and with an unmodified indicator mRNA, if desired. As exemplified, the HIV-1 $p17^{gag}$ mutants are compared to the unmutated HIV-1 $p17^{gag}$ in transfection experiments by subsequent analysis of the mRNAs by Northern blot analysis. The proteins produced by these mRNAs are measured by immunoblotting and other methods known in the art, such as ELISA. See infra.

VI. INDUSTRIAL APPLICABILITY

Genes which can be mutated by the methods of this invention include those whose mRNAs are known or suspected of containing INS regions in their mRNAs. These genes include, for example, those coding for growth factors, interferons, interleukins, the fos proto-oncogene protein, and HIV-1 gag, env and pol, as well as other viral mRNAs in addition to those exemplified herein. Genes mutated by the methods of this invention can be expressed in the native host cell or organism or in a different cell or organism. The mutated genes can be introduced into a vector such as a plasmid, cosmid, phage, virus or mini-chromosome and inserted into a host cell or organism by methods well known in the art. In general, the mutated genes or constructs containing these mutated genes can be utilized in any cell, either eukaryotic or prokaryotic, including mammalian cells (e.g., human (e.g., HeLa), monkey (e.g., Cos), rabbit (e.g., rabbit reticulocytes), rat, hamster (e.g., CHO and baby hamster kidney cells) or mouse cells (e.g., L cells), plant cells, yeast cells, insect cells or bacterial cells (e.g., E. coli). The vectors which can be utilized to clone and/or express these mutated genes are the vectors which are capable of replicating and/or expressing the mutated genes in the host cell in which the mutated genes are desired to be replicated and/or expressed. See, e.g., F. Ausubel et al., Current Protocols in Molecular Biology, Greene Publishing Associates and Wiley-Interscience (1992) and Sambrook et al. (1989) for examples of appropriate vectors for various types of host cells. The native promoters for such genes can be replaced with strong promoters compatible with the host into which the gene is inserted. These promoters may be inducible. The host cells containing these mutated genes can be used to express large amounts of the protein useful in enzyme preparations, pharmaceuticals, diagnostic reagents, vaccines and therapeutics.

Genes altered by the methods of the invention or constructs containing said genes may also be used for in-vivo or in-vitro gene replacement. For example, a gene which produces an mRNA with an inhibitory instability region can be replaced with a gene that has been modified by the method of the invention in situ to ultimately increase the amount of protein expressed. Such gene include viral genes and/or cellular genes. Such gene replacement might be useful, for example, in the development of a vaccine and/or genetic therapy.

The constructs and/or proteins made by using constructs encoding the exemplified altered gag, env, and pol genes could be used, for example, in the production of diagnostic reagents, vaccines and therapies for AIDS and AIDS related diseases. The inhibitory/instability elements in the exemplified HIV-1 gag gene may be involved in the establishment of a state of low virus production in the host. HIV-1 and the other lentiviruses cause chronic active infections that are not cleared by the immune system. It is possible that complete removal of the inhibitory/instability sequence elements from the lentiviral genome would result in constitutive expression. This could prevent the virus from establishing a latent infection and escaping immune system surveillance. The success in increasing expression of $p17^{gag}$ by eliminating the inhibitory sequence element suggests that one could produce lentiviruses without any negative elements. Such lentiviruses could provide a novel approach towards attenuated vaccines.

For example, vectors expressing high levels of Gag can be used in immunotherapy and immunoprophylaxis, after expression in humans. Such vectors include retroviral vectors and also include direct injection of DNA into muscle cells or other receptive cells, resulting in the efficient expression of gag, using the technology described, for example, in Wolff et al., *Science* 247:1465–1468 (1990), Wolff et al.; *Human Molecular Genetics* 1(6):363–369 (1992) and Ulmer et al., *Science* 259:1745–1749 (1993). Further, the gag constructs could be used in transdominant inhibition of HIV expression after the introduction into humans. For this application, for example, appropriate vectors or DNA molecules expressing high levels of $p_{55}^{gag}$ or $p37^{gag}$ would be modified to generate transdominant gag mutants, as described, for example, in Trono et al., *Cell* 59:113–120 (1989). The vectors would be introduced into humans, resulting in the inhibition of HIV production due to the combined mechanisms of gag transdominant inhibition and of immunostimulation by the produced gag protein. In addition, the gag constructs of the invention could be used in the generation of new retroviral vectors based on the expression of lentiviral gag proteins. Lentiviruses have unique characteristics that may allow the targeting and efficient infection of non-dividing cells. Similar applications are expected for vectors expressing high levels of env.

Identification of similar inhibitory/instability elements in SIV indicates that this virus may provide a convenient model to test these hypotheses.

The exemplified constructs can also be used to simply and rapidly detect and/or further define the boundaries of inhibitory/instability sequences in any mRNA which is known or suspected to contain such regions, e.g., in mRNAs encoding various growth factors, interferons or interleukins, as well as other viral mRNAs in addition to those exemplified herein.

The following examples illustrate certain embodiments of the present invention, but should not be construed as limiting its scope in any way. Certain modifications and variations will be apparent to those skilled in the art from the teachings of the foregoing disclosure and the following examples, and these are intended to be encompassed by the spirit and scope of the invention.

EXAMPLE 1

HIV-1 GAG Gene

The interaction of the Rev regulatory protein of human immunodeficiency virus type 1 (HIV-1) with its RNA target, named the Rev-responsive element (RRE), is necessary for expression of the viral structure proteins (for reviews see G. Pavlakis and B. Felber, New Biol. 2:20–31 (1990); B. Cullen and W. Greene, Cell 58:423–426 (1989); and C. Rosen and G. Pavlakis, AIDS J. 4:499–509 (1990)). Rev acts by promoting the nuclear export and increasing the stability of the RRE-containing mRNAs. Recent results also indicate a role for REV in the efficient polysome association of these mRNAs (S. Arrigo and I. Chen, Gene Dev. 5:808–819 (1991), D. D'Agostino et al., Mol. Cell Biol. 12:1375–1386 (1992)). Since the RRE-containing HIV-1 mRNAs do not efficiently produce protein in the absence of Rev, it has been postulated that these mRNAs are defective and contain inhibitory/instability sequences variously designated as INS, CRS, or IR (M. Emerman et al. Cell 57:1155–1165 (1989); S. Schwartz et al., J. Virol. 66:150–159 (1992); C. Rosen et al., Proc. Natl. Acad. Sci. USA 85:2071–2075 (1988); M. Hadzopoulou-Cladaras et al., J. Virol. 63:1265–1274 (1989); F. Maldarelli et al., J. Virol. 65:5732–5743 (1991); A. W. Cochrane et al., J. Virol. 65:5305–5313 (1991)). The nature and function of these inhibitory/instability sequences have not been characterized in detail. It has been postulated that inefficiently used splice sites may be necessary for Rev function (D. Chang and P. Sharp, Cell 59:789–795 (1989)); the presence of such splice sites may confer Rev-dependence to HIV-1 mRNAs.

Analysis of HIV-1 hybrid constructs led to the initial characterization of 'some inhibitory/instability sequences in the gag and pol regions of HIV-1 (S. Schwartz et al., J. Virol. 66:150–159 (1992); F. Maldarelli et al., J Virol 65:5732–5743 (1991); A. W. Cochrane et al., J. Virol. 65:5305–5313 (1991)). The identification of an inhibitory/instability RNA element located in the coding region of the p17$^{gag}$ matrix protein of HIV-1 was also reported (S. Schwartz et al., J. Virol. 66:150–159 (1992)). It was shown that this sequence acted in cis to inhibit HIV-1 tat expression after insertion into a tat cDNA. The inhibition could be overcome by Rev-RRE, demonstrating that this element plays a role in regulation by Rev.

1. p17$^{gag}$ Expression Plasmid

To further study the inhibitory/instability element in p17$^{gag}$, a p17$^{gag}$ expression plasmid (p17, FIG. 1) was constructed. The p17$^{gag}$ sequence was engineered to contain a translational stop codon immediately after the coding sequence and thus could produce only p17$^{gag}$ (the construction of this plasmid is described below). The major 5' splice site of HIV-1 upstream of the gag AUG has been deleted from this vector (B. Felber et al., Proc. Natl. Acad. Sci. USA 86:1495–1499 (1989)). To investigate whether plasmid p17 could produce p17$^{gag}$ in the absence of Rev and the RRE, p17 was transfected into HLtat cells (S. Schwartz et al., J. Virol. 64:2519–2529 (1990)) (see below). These cells constitutively produce HIV-1 Tat protein, which is necessary for transactivation of the HIV-1 LTR promoter. Plasmid p17 was transfected in the absence or presence of Rev, and the production of p17$^{gag}$ was analyzed by western immunoblotting. The results revealed that very low levels of p17$^{gag}$ protein were produced (FIG. 2A). The presence of Rev did not increase gag expression, as expected, since this mRNA did not contain the RRE. Next, a plasmid that contained both the p17$^{gag}$ coding sequence and the RRE (p17R, FIG. 1) was constructed. Like p17, this plasmid produced very low levels of p17$^{gag}$ in the absence of Rev. High levels of p17$^{gag}$ were produced only in the presence of Rev (FIG. 2A). These experiments suggested that an inhibitory/instability element was located in the p17$^{gag}$ coding sequence.

Expression experiments using various eucaryotic vectors have indicated that several other retroviruses do not contain such inhibitory/instability sequences within their coding sequences (see for example, J. Wills et al., J. Virol. 63:4331–43 (1989) and V. Morris et al., J. Virol. 62:349–53 (1988)). To verify these results, the p17$^{gag}$ (matrix) gene of HIV-1 in plasmid p17 was replaced with the coding sequence for p19$^{gag}$ (matrix) which is the homologous protein of the Rous sarcoma virus (RSV, strain SR-A). The resulting plasmid, p19 (FIG. 1), was identical to plasmid p17, except for the gag coding sequence. The production of p19$^{gag}$ protein from plasmid p19 was analyzed by western immunoblotting, which revealed that this plasmid produced high levels of p19$^{gag}$ (FIG. 2A). These experiments demonstrated that the p19$^{gag}$ coding sequence of RSV, in contrast to p17$^{gag}$ of HIV-1, could be efficiently expressed in this vector, indicating that the gag region of RSV did not contain any inhibitory/instability elements. A derivative of plasmid p19 that contained the RRE, named p19R (FIG. 1) was also constructed. Interestingly, only very low levels of p19$^{gag}$ protein were produced from the RRE-containing plasmid p19R in the absence of Rev. This observation indicated that the introduced RRE and 3' HIV-1 sequences exerted an inhibitory effect on p19$^{gag}$ expression from plasmid p19R, which is in agreement with recent data indicating that in the absence of Rev, a longer region at the 3' end of the virus including the RRE acts as an inhibitory/instability element (G. Nasioulas, G. Pavlakis, B. Felber, manuscript in preparation). In conclusion, the high levels of expression of RSV p19$^{gag}$ in the same vector reinforced the conclusion that an inhibitory/instability sequence within HIV-1 p17$^{gag}$ coding region was responsible for the very low levels of expression.

It was next determined whether the inhibitory/instability effect of the p17$^{gag}$ coding sequence was detected also at the mRNA level. Northern blot analysis of RNA extracted from HLtat cells transfected with p17 or transfected with p17R demonstrated that p17R produced lower mRNA levels in the absence of Rev (FIG. 3A) (See Example 3). A two- to eight-fold increase in p17R mRNA levels was observed after coexpression with Rev. Plasmid p17 produced mRNA levels similar to those produced by p17R in the absence of Rev. Notably, Rev decreased the levels of mRNA and protein produced by mRNAs that do not contain RRE. This inhibitory effect of Rev in cotransfection experiments has been observed for many other non-RRE-containing mRNAs, such as luciferase and CAT (L. Solomin et al., J. Virol 64:6010–6017 (1990); D. M. Benko et al., New Biol 2:1111–1122 (1990)). These results established that the inhibitory element in gag also affects the mRNA levels and are in agreement with previous findings (S. Schwartz et al., J. Virol. 66:150–159 (1992)). Quantitations of the mRNA and protein levels produced by p17R in the absence or presence of Rev were performed by scanning densitometry of appropriate serial dilutions of the samples, and indicated that the difference was greater at the level of protein (60- to 100-fold) than at the level of mRNA (2- to 8-fold). This result is compatible with previous findings of effects of Rev on mRNA localization and polysomal loading of both gag and env mRNAs (S. Arrigo et al., Gene Dev 5:808–819 (1991); D. D'Agostino et al., Mol. Cell. Biol. 12:1375–1386 (1992); M. Emerman et al., Cell 57:1155–1165 (1989); B. Felber et al., Proc. Natl. Acad. Sci. USA 86:1495–1499 (1989), M. Malim et al., Nature (London) 338:254–257 (1989)). Northern blot analysis of the mRNAs produced by the RSV gag expression plasmids revealed that p19 produced high mRNA levels (FIG. 3B). This further demonstrated that the p19$^{gag}$ coding sequence of RSV does not contain inhibitory elements. The presence of the RRE and 3' HIV-1 sequences in plasmid p19R resulted in decreased mRNA levels in the absence of Rev, further suggesting that inhibitory elements were present in these sequences. Taken together, these results established that gag expression in HIV-1 is fundamentally different from that in RSV. The HIV-1 p17$^{gag}$ coding sequence contains a strong inhibitory element while the RSV p19$^{gag}$ coding sequence does not. Interestingly, plasmid p19 contains the 5' splice site used to generate the RSV env mRNA, which is located downstream of the gag AUG. This 5' splice site is not utilized in the described expression vectors (FIG. 3B). Mutation of the invariable GT dinucleotide of this 5' splice site to AT did not affect p19$^{gag}$ expression significantly (data not shown). On the other hand, the HIV-1 p17 expression plasmid did not contain any known splice sites, yet was not expressed in the absence of Rev. These results further indicate that sequences other than inefficiently used splice sites are responsible for inhibition of gag expression.

2. Mutated p17$^{gag}$ vectors

To investigate the exact nature of the inhibitory element in HIV-1 gag, site-directed mutagenesis of the p17$^{gag}$ coding sequence with four different oligonucleotides, as indicated in FIG. 4, was performed. Each oligonucleotide introduced several point mutations over an area of 19–22 nucleotides. These mutations did not affect the amino acid sequence of the p17$^{gag}$ protein, since they introduced silent codon changes. First, all four oligonucleotides were used simultaneously in mutagenesis using a single-stranded DNA template as described (T. Kunkel, Proc. Natl. Acad. Sci. USA 82:488–492 (1985); S. Schwartz et al., Mol. Cell. Biol. 12:207–219 (1992)). This allowed the simultaneous introduction of many point mutations over a large region of 270 nt in vector p17. A mutant containing all four oligonucleotides was isolated and named p17M1234. Compared to p17, this plasmid contained a total of 28 point mutations distributed primarily in regions with high AU-content. The phenotype of the mutant was assessed by transfections into HLtat cells and subsequent analysis of p17$^{gag}$ expression by immunoblotting. Interestingly, p17M1234 produced high levels of p17$^{gag}$ protein, higher than those produced by p17R in the presence of Rev (FIG. 2A). This result demonstrated that the inhibitory/instability signals in p17$^{gag}$ mRNA had been inactivated in plasmid p17M1234. As expected, the presence of Rev protein did not increase expression from p17M1234, but instead, had a slight inhibitory effect on gag expression. Thus, p17$^{gag}$ expression from the mutant p17M1234 displayed the same general properties as the p19$^{gag}$ of RSV, that is, a high constitutive level of Rev-independent gag expression. Northern blot analysis revealed that the mRNA levels produced by p17M1234 were increased compared to those produced by p17 (FIG. 3A).

To further examine the nature and exact location of the minimal inhibitory/instability element, the p17$^{gag}$ coding sequence in plasmid p17 was mutated with only one of the four mutated oligonucleotides at a time. This procedure resulted in four mutant plasmids, named p17M1, p17M2, p17M3, and p17M4, according to the oligonucleotide that each contains. None of these mutants produced significantly higher levels of p17$^{gag}$ protein compared to plasmid p17 (FIG. 5), indicating that the inhibitory/instability element was not affected. The p17 coding sequence was next mutated with two oligonucleotides at a time. The resulting mutants were named p17M12, p17M13, p17M14, p17M23, p17M24, and p17M34. Protein production from these mutants was minimally increased compared with that from p17, and it was considerably lower than that from p17M1234 (FIG. 5). In addition, a triple oligonucleotide mutant, p17M123, also failed to express high levels of p17$^{gag}$ (data not shown). These findings may suggest that multiple inhibitory/instability signals are present in the coding sequence of p17$^{gag}$. Alternatively, a single inhibitory/instability element may span a large region, whose inactivation requires mutagenesis with more than two oligonucleotides. This possibility is consistent with previous data suggesting that a 218-nucleotide inhibitory/instability element in the p17$^{gag}$ coding sequence is required for strong inhibition of gag expression. Further deletions of this sequence resulted in gradual loss of inhibition (S. Schwartz et al., J. Virol. 66:150–159 (1992)). The inhibitory/instability element may coincide with a specific secondary structure on the mRNA. It is currently being investigated whether a specific structure is important for the function of the inhibitory/instability element.

The p17$^{gag}$ coding sequence has a high content of A and U nucleotides, unlike the coding sequence of p19$^{gag}$ of RSV (S. Schwartz et al., J. Virol. 66:150–159 (1992); G. Myers and G. Pavlakis, in *The Retroviridae* J. Levy, Eds. (Plenum Press, New York, N.Y., 1992), pp. 1–37). Four regions with high AU content are present in the p17$^{gag}$ coding sequence and have been implicated in the inhibition of gag expression (S. Schwartz et al., J. Virol. 66:150–159 (1992)). Lentiviruses have a high AU content compared to the mammalian genome. Regions of high AU content are found in the gag/pol and env regions, while the multiply spliced mRNAs have a lower AU content (G. Myers and G. Pavlakis, in *The Retroviridae*, J. Levy, Eds. (Plenum Press, New York, N.Y., 1992), pp. 1–37), supporting the possibility that the inhibitory/instability elements are associated with mRNA regions with high AU content. It has been shown that a specific oligonucleotide sequence, AUUUA, found at the AU-rich 3' untranslated regions of some unstable mRNAs, may confer RNA instability (G. Shaw and R. Kamen, Cell 46:659–667 (1986)). Although this sequence is not present in the p17$^{gag}$ sequence, it is found in many copies within gag/pol and env regions. The association of instability elements with AU-rich regions is not universal, since the RRE together with 3' HIV sequences, which shows a strong inhibitory/instability activity in our vectors, is not AU-rich. These observations suggest the presence of more than one type of inhibitory/instability sequences. In addition to reducing the AU content, some of the mutations introduced in plasmid p17 changed rarely used codons to more favored codons for human cells. Although the use of rare codons could be an alternative explanation for poor HIV gag expression, this type of translational regulation is not favored by these results, since the presence of Rev corrects the defect in gag expression. In addition, the observation that the presence of non-translated sequences reduced gag expression (for example, the RRE sequence in p17R), suggests that translation of the inhibitory/instability region is not necessary for inhibition. Introduction of RRE and 3' HIV sequences in p17M1234 was also able to decrease gag expression, verifying that independent negative elements not acting co-translationally are responsible for poor expression.

3. Identification and Elimination of Additional INS Sequences in the p24 and p15 Regions of the gag Gene To examine the effect of removal of INS in the $p_{17}^{gag}$ coding region (the $p17^{gag}$ coding region spans nucleotides 336–731, as described in the description of FIG. 1.(B) above, and contains the first of three parts (i.e., p17, p24, and p15) of the gag coding region, as indicated on in FIGS. 1.(A) and (B)) on the expression of the complete gag gene expression vectors were constructed in which additional sequences of the gag gene were inserted 3' to the mutationally altered $p17^{gag}$ coding region, downstream of the stop codon, of vector p17M1234. Three vectors containing increasing lengths of gag sequences were studied: p17M1234(731–1081), p17M1234(731–1424) and p17M1234(731–2165), as shown in FIG. 1.(C). Levels of expression of $p17^{gag}$ were measured, with the results indicating that region of the mRNA encoding the second part of the gag protein (i.e., the part encoding the $p24^{gag}$ protein, which spans nucleotides 731–1424) contains only a weak INS, as determined by a small reduction in the amount of $p17^{gag}$ protein expressed by p17M1234 as compared with the amount of $p17^{gag}$ protein expressed by p17M1234 (731–1424), while the region of the mRNA encoding the third part of the gag protein (i.e., the part encoding the $p15^{gag}$ protein, which spans nucleotides 1425–2165) contains a strong INS, as determined by a large reduction in the amount of gag protein expressed by p17M1234(731–2165) as compared with the amount of protein expressed by p17M1234 and p17M1234(731–1424).

4. p37M1234 Vector

The above analysis allowed the construction of vector p37M1234, which expressed high levels of $p37^{gag}$ precursor protein (which contains both the $p17^{gag}$ and $p24^{gag}$ protein regions). Vector p37M1234 was constructed by removing the stop codon at the end of the gene encoding the altered $p17^{gag}$ protein and fusing the nucleotide sequence encoding the $p24^{gag}$ protein into the correct reading frame by oligonucleotide mutagenesis. This restored the nucleotide sequence so that it encoded the fused $p17^{gag}$ and $p24^{gag}$ protein (i.e., the $p37^{gag}$ protein) as it is encoded by HIV-1. Since the presence of the $p37^{gag}$ or of the $p24^{gag}$ protein can be quantitated easily by commercially available ELISA kits, vector p37M1234 can be used for inserting and testing additional fragments suspected of containing INS. Examples of such uses are shown below.

5. Vectors p17M1234(731–1081)NS and p55BM1234

Other vectors which were constructed in a similar manner as was P37M1234 were p17M1234(731–1081)NS and p55BM1234 (FIG. 1.(C)). The levels of gag expression from each of these three vectors which allow the translation of the region downstream (3') of the p17 coding region, were respectively similar to the level of gag expression from the vectors containing the nucleotide sequences 3' to a stop codon (i.e., vectors p17M1234(731–1081), p17M1234 (731–1424) and p17M1234(731–2165), described above). These results also demonstrate that the INS regions in the gag gene are not affected by translation or lack thereof through the INS region. These results demonstrate the use of p17M1234 to detect additional INS sequences in the HIV-1 gag coding region (i.e., in the 1424–2165 encoding region of HIV-1 gag). Thus, these results also demonstrate how a gene containing one or more inhibitory/instability regions can be mutated to eliminate one inhibitory/instability region and then used to further locate additional inhibitory/instability regions within that gene, if any.

6. Vectors p37M1-10D and p55M1-10

As described above, experiments indicated the presence of INS in the p24 and p15 region of HIV-1 in addition to those identified and eliminated in the $p17^{gag}$ region of HIV-1. This is depicted schematically in FIG. 6 on page 7180 of Schwartz et al., J. Virol. 66:7176–7182 (1992). In that figure, cgagM1234 is identical to p55BM1234.

By studying the expression of $p24^{gag}$ protein in vectors encoding the $p24^{gag}$ protein containing additional gag and pol sequences, it was found that vectors that contained the complete gag gene and part of the pol gene (e.g. vector p55BM1234, see FIG. 6) were not expressed at high levels, despite the elimination of INS-1 in the $p17^{gag}$ region as described above. The inventors have hypothesized that this is caused by the presence of multiple INS regions able to act independently of each other. To eliminate the additional INS, several mutant HIV-1 oligonucleotides were constructed (see Table 2) and incorporated in various gag expression vectors. For example, oligonucleotides M6gag, M7gag, M8gag and M10gag were introduced into p37M1234, resulting in p37M1-10D and the same oligonucleotides were introduced into p55BM1234, resulting in p55BM1-10. These experiments revealed a dramatic improvement of expression of $p37^{gag}$ (which is the $p17^{gag}$ and $p24^{gag}$ precursor) and $p55^{gag}$ (which is the intact gag precursor molecule produced by HIV-1) upon the incorporation in the expression vectors p37M1234 and p55BM1234 of additional mutations contained in the oligonucleotides M6gag, M7gag, M8gag and M10gag (described in Table 2). FIG. 6 shows that expression was dramatically improved after the introduction of additional mutations.

Of particular interest was p37M1-10D, which produced very high levels of gag. This has been the highest producing gag construct (see FIG. 6). Interestingly, addition of gag and pol sequences as in vectors p55BM1-10 and p55AM1-10 (FIG. 6) reduced the levels of gag expression. Upon further mutagenesis, the inhibitory effects of this region were partially eliminated as shown in FIG. 6 for vector p55M1-13P0. Introduction of mutations defined by the gag region nucleotides M10gag, M11gag, M12gag, M13gag, and pol region nucleotide M0pol increased the levels of gag expression approximately six fold over vectors such as p55BM1-10.

The HIV-1 promoter was replaced by the human cytomegalovirus early promoter (CMV) in plasmids p37M1-10D and p55M1-13P0 to generate plasmids pCMV37M1-10D and pCMV55M1-13P0, respectively. For this, a fragment containing the CMV promoter was amplified by PCR (nucleotides −670 to +73, where +1 is the start of transcription, see, Boshart, et al., Cell, 41, 521 (1985)). This fragment was exchanged with the StuI-BssHII fragment in gag vectors p37M1-10D and p55M1-13P0, resulting in the replacement of the HIV-1 promoter with that of CMV. The resulting plasmids were compared to those containing the HIV-1 promoter after transfection in human cells, and gave similar high expression of gag. Therefore, the high expression of gag can be achieved in the total absence of any other viral protein. The exchange of the HIV-1 with other promoters is beneficial if constitutive expression is desirable and also for expression in other mammalian cells, such as mouse cells, in which the HIV-1 promoter is weak.

The constructed vectors p37M1-10D and P55BM1-10 can be used for the Rev independent production of p37$^{gag}$ and p55$^{gag}$ proteins, respectively. In addition, these vectors can be used as convenient reporters, to identify and eliminate additional INS in different RNA molecules.

Using the protocols described herein, regions have been identified within the gp41 (the transmembrane part of HIV-1 env) coding area and at the post-env 3' region of HIV-1 which contain INS. The elimination of INS from gag, pol and env regions will allow the expression of high levels of authentic HIV-1 structural proteins in the absence of the Rev regulatory factor of HIV-1. The mutated coding sequences can be incorporated into appropriate gene transfer vectors which may allow the targeting of specific cells and/or more efficient gene transfer. Alternatively, the mutated coding sequences can be used for direct expression in human or other cells in vitro or in vivo with the goal being the production of high protein levels and the generation of a strong immune response. The ultimate goal in either case is subsequent protection from HIV infection and disease.

The described experiments demonstrate that the inhibitory/instability sequences are required to prevent HIV-1 expression. This block to the expression of viral structural proteins can be overcome by the Rev-RRE interaction. In the absence of INS, HIV-1 expression would be similar to simpler retroviruses and would not require Rev. Thus, the INS is a necessary component of Rev regulation. Sequence comparisons suggest that the INS element identified here is conserved in all HIV-1 isolates, although this has not been verified experimentally. The majority (22 of 28) of the mutated nucleotides in gag are conserved in all HIV-1 isolates, while 22 of 28 are conserved also in HIV-2 (G. Myers, et al., Eds. *Human retroviruses and AIDS. A compilation and analysis of nucleic acid and amino acid sequences* (Los Alamos National Laboratory, Los Alamos, N.Mex., 1991), incorporated herein by reference). Several lines of evidence indicate that all lentiviruses and other complex retroviruses such as the HTLV group contain similar INS regulatory elements. Strong INS elements have been identified in the gag region of HTLV-I and SIV (manuscript in preparation). This suggests that INS are important regulatory elements, and may be responsible for some of the biological characteristics of the complex retroviruses. The presence of INS in SIV and HTLV-I suggests that these elements are conserved among complex retroviruses. Since INS inhibit expression, it must be concluded that their presence is advantageous to the virus, otherwise they would be rapidly eliminated by mutations.

The observations that the inhibitory/instability sequences act in the absence of any other viral proteins and that they can be inactivated by mutagenesis suggest that these elements may be targets for the binding of cellular factors that interact with the mRNA and inhibit post transcriptional steps of gene expression. The interaction of HIV-1 mRNAs with such factors may cause nuclear retention, resulting in either further splicing or rapid degradation of the mRNAs. It has been proposed that components of the splicing machinery interact with splice sites in HIV-1 mRNAs and modulated mRNA expression (A. Cochrane et al., J. Virol. 65:5305–5313 (1991); D. Chang and P. Sharp, Cell 59:789–795 (1989); X. Lu et al., Proc. Natl. Acad. Sci. USA 87:7598–7602 (1990)). However, it is not likely that the inhibitory/instability elements described here are functional 5' or 3' splice sites. Thorough mapping of HIV-1 splice sites performed by several laboratories using the Reverse Transcriptase-PCR technique failed to detect any splice sites within gag (S. Schwartz et al., J. Virol. 64:2519–2529 (1990); J. Guatelli et al., J. Virol. 64:4093–4098 (1990); E. D. Gerrett et al., J. Virol. 65:1653–1657 (1991); M. Robert-Guroff et al., J. Virol. 64:3391–3398 (1990); S. Schwartz et al., J. Virol. 64:5448–5456 (1990); S. Schwartz et al., Virology 183:677–686 (1991)). The suggestions that Rev may act by dissociating unspliced mRNA from the spliceosomes (D. Chang and P. Sharp, Cell 59:789–795 (1989)) or by inhibiting splicing (J. Kjems et al., Cell 67:169–178 (1991)) are not easily reconciled with the knowledge that all retroviruses produce structural proteins from mRNAs that contain unutilized splice sites. Splicing of all retroviral mRNAs, including HIV-1 mRNAs in the absence of Rev, is inefficient compared to splicing of cellular mRNAs (J. Kjems et al., Cell 67:169–178 (1991); A. Krainer et al., Gene Dev. 4:1158–1171 (1990); R. Katz and A. Skalka, Mol. Cell. Biol. 10:696–704 (1990); C. Stoltzfus and S. Fogarty, J. Virol. 63:1669–1676 (1989)). The majority of the retroviruses do not produce Rev-like proteins, yet they efficiently express proteins from partially spliced mRNAs, suggesting that inhibition of expression by unutilized splice sites is not a general property of retroviruses. Experiments using constructs expressing mutated HIV-1 gag and env mRNAs lacking functional splice sites showed that only low levels of these mRNAs accumulated in the absence of Rev and that their expression was Rev-dependent (M. Emerman et al., Cell 57:1155–1165 (1989); B. Felber et al., Proc. Natl. Acad. Sci. USA 86:1495–1499 (1989); M. Malim et al., Nature (London) 338:254–257 (1989)). This led to the conclusion that Rev acts independently of splicing (B. Felber et al., Proc. Natl. Acad. Sci. USA 86:1495–1499 (1989); M. Malim et al., Nature (London) 338:254–257 (1989)) and to the proposal that inhibitory/instability elements other than splice sites are present on HIV-1 mRNAs (C. Rosen et al., Proc. Natl. Acad. Sci. USA 85:2071–2075 (1988); M. Hadzopoulou-Cladaras, et al., J. Virol. 63:1265–1274 (1989); B. Felber et al., Proc. Natl. Acad. Sci. USA 86:1495–1499 (1989)).

Construction of the Gag Expression Plasmids

Plasmid p17R has been described as pNL17R (S. Schwartz et al., J. Virol. 66:150–159 (1992)). Plasmid p17 was generated from p17R by digestion with restriction enzyme Asp718 followed by religation. This procedure deleted the RRE and HIV-1 sequences spanning nt 8021–8561 upstream of the 3' LTR. To generate mutants of $p17^{gag}$, the $p17^{gag}$ coding sequence was subcloned into a modified pBLUESCRIPT vector (Stratagene) and generated single stranded uracil-containing DNA. Site-directed mutagenesis was performed as described (T. Kunkel, Proc. Natl. Acad. Sci. USA 82:488–492 (1985); S. Schwartz et al., Mol. Cell Biol. 12:207–219 (1992)). Clones containing the appropriate mutations were selected by sequencing of double-stranded DNA. To generate plasmid p19R, plasmid p17R was first digested with BssHII and EcoRI, thereby deleting the entire $p17^{gag}$ coding sequence, six nucleotides upstream of the $p17^{gag}$ AUG and nine nucleotides of linker sequences 3' of the $p17^{gag}$ stop codon. The $p17^{gag}$ coding sequence in p17R was replaced by a PCR-amplified DNA fragment containing the RSV $p19^{gag}$ coding sequence (R. Weiss et al., *RNA Tumor Viruses. Molecular Biology of Tumor Viruses* (Cold Spring Harbor Laboratory, Cold Spring Harbor, N.Y., 1985)). This fragment contained eight nucleotides upstream of the RSV gag AUG and the $p19^{gag}$ coding sequence immediately followed by a translational stop codon. The RSV gag fragment was derived form the infectious RSV proviral clone S-RA (R. Weiss et al., *RNA Tumor Viruses. Molecular Biology of Tumor Viruses* (Cold Spring Harbor Laboratory, Cold Spring Harbor, N.Y., 1985)). p19 was derived from p19R by excising an Asp 718 fragment containing the RRE and 3' HIV-1 sequences spanning nt 8021–8561.

Transfection of HLtat Cells with Gag Expression Plasmids

HLtat cells (S. Schwartz et al., J. Virol. 64:2519–2529 (1990)) were transfected using the calcium coprecipitation technique (F. Graham et al. and A. Van der Eb, Virology 52:456–460 (1973)) as described (B. Felber et al., Proc. Natl. Acad. Sci. USA 86:1495–1499 (1989)), using 5 μg of p17, p17R, p17M1234, p19, or p19R in the absence (−) or presence (+) of 2 μg of the Rev-expressing plasmid pL3crev (B. Felber et al., Proc. Natl. Acad. Sci. USA 86:1495–1499 (1989)). The total amount of DNA in transfections was adjusted to 17 μg per 0.5 ml of precipitate per 60 mm plate using pUC19 carrier DNA. Cells were harvested 20 h after transfected and cell extracts were subjected to electrophoresis on 12.5%-denaturing polyacrylamide gels and analyzed

EXAMPLE 2

HIV-1 ENV Gene

Fragments of the env gene were inserted into vectors p19 or p37M1234 and the expression of the resulting plasmids were analyzed by transfections into HLtat cells. It was found that several fragments inhibited protein expression. One of the strong INS identified was in the fragment containing nucleotides 8206–8561 ("fragment [8206–8561]"). To eliminate this INS, the following oligonucleotides were synthesized and used in mutagenesis experiments as specified supra. The fragment was derived from the molecular clone pNL43, which is almost identical to HXB2. The numbering system used herein follows the numbering of molecular clone HXB2 throughout. The synthesized oligonucleotides follow the pNL43 sequence.

The oligonucleotides which were used to mutagenize fragment [8206–8561], and which made changes in the env coding region between nucleotides 8210–8555 (the letters in lower case indicate mutated nucleotides) were:

```
#1:
8194-8261
GAATAGTGCTGTTAACcTcCTgAAcGCtACcGCtATcGCcGTgGCgGAaGGaACcGAc    (SEQ ID NO:10)
AGGGTTATAG

#2
8262-8323
AAGTATTACAAGCcGCcTAccGcGCcATcaGaCAtATcCCccGccGcATccGcCAGGG    (SEQ ID NO:11)
CTTG

#3
8335-8392
GCTATAAGATGGGcGGtAAaTGGagcAAgtcctccGTcATcGGcTGGCCTGCTGTAAG    (SEQ ID NO:12)

#4
8393-8450
GGAAAGAATGcGcaGgGCcGAaCCcGCcGCcGAcGGaGTtGGcGCcGTATCTCGAGAC    (SEQ ID NO:13)

#5
8451-8512
CTAGAAAAACAcGGcGCcATtACctcctctAAcACcGCcGCcAAtAAcGCcGCTTGTG    (SEQ ID NO:14)
CCTG

#6
8513-8572
GCTAGAAGCACAgGAaGAaGAgGAaGTcGGcTTcCCcGTtACcCCTCAGGTACCTTTA    (SEQ ID NO:15)
AG
``` by immunoblotting using either human HIV-1 patient serum (Scripps) or a rabbit anti-p19$^{gag}$ serum. pRSV-luciferase (J. de Wet et al., Mol. Cell. Biol. 7:725–737 (1987)) that contains the firefly luciferase gene linked to the RSV LTR promoter, was used as an internal standard to control for transfection efficiency and was quantitated as described (L. Solomin et al., J. Virol. 64:6010–6017 (1990)). The results are set forth in FIG. 2.

Northern Blot Analysis

HLtat cells were transfected as described above and harvested 20 h post transfection. Total RNA was prepared by the heparin/DNase method (Z. Krawczyk and C. Wu, Anal. Biochem. 165:20–27 (1987)), and 20 μg of total RNA was subjected to northern blot analysis as described (M. Hadzopoulou-Cladaras et al., J. Virol. 63:1265–1274 (1989)). The filters were hybridized to a nick-translated PCR-amplified DNA fragment spanning nt 8304–9008 in the HIV-1 3' LTR. The results are set forth in FIG. 3.

The expression of env was increased by the elimination of the INS in fragment [8206–8561] as determined by analysis of both mRNA and protein.

To further characterize in detail the INS in HIV-1 env, the coding region of env was divided into different fragments, which were produced by PCR using appropriate synthetic oligonucleotides, and cloned in vector p37M1-10D. This vector was produced from p37M1234 by additional mutagenesis as described above. After introduction into human cells, vector p37M1-10D produces high levels of p37$^{gag}$ protein. Any strong INS element will inhibit the expression of gag if ligated in the same vector. The summary of the env fragments used is shown in FIG. 11. The results of these experiments show that, like in HIV-1 gag, there exist multiple regions inhibiting expression in HIV-1 env, and combinations of such regions result in additive or synergistic inhibition. For example, while fragments 1, 2, or 3 individually inhibit expression by 2–6 fold, the combination of these fragments inhibits expression by 30 fold. Based on these results, additional mutant oligonucleotides have been synthesized for the correction of env INS. These oligonucleotides have been introduced in the expression vectors for HIV-1 env p120pA and p120R270 (see FIG. 7) for the development of Rev-independent HIV-1 env expression plasmids as discussed in detail below.

1. The mRNAs for gp160 and for the Extracellular Domain (gp120) are Defective and their Expression Depends on the Presence of RRE in cis and Rev in Trans 1.1 Positive and Negative Determinants for env mRNA Expression of HIV Previous experiments on the identification and characterization of the env expressing cDNAs had demonstrated that Env is produced from mRNAs that contain exon 4AE, 4BE, or 5E. (Schwartz et al., J. Virol. 64:5448–5456 (1990); Schwartz et al., Mol. Cell. Biol. 12:207–219 (1992). All constructs generated to study the determinants of env expression are derived from pNL15E. This plasmid contains the HIV-1 LTR promoter, the complete env cDNA 15E, and the HIV 3' LTR including the polyadenylation signal (Schwartz, et al. J. Virol. 64:5448–5456 (1990) (FIG. 7). pNL15E was generated from the molecular clone pNL4-3 (pNL4-3 is identical to pNL43 herein) (Adachi et al., J. Virol. 59:284–291 (1986) and lacks the splice acceptor site for exon 6D, which was used to generate the tev mRNA (Benko et al., J. Virol. 64:2505–2518 (1990). The Env expression plasmids were transfected in the presence or absence of the Rev-expressing plasmid pL3crev (Felber et al., J. Virol. 64:3734–3741 (1990) into HLtat cells (Schwartz et al., J. Virol. 64:2519–2529 (1990), which constitutively express Tat (one-exon Tat). One day later, the cells were harvested for analyses of RNA and protein. Total RNA was extracted and analyzed on Northern blots. Protein production was measured by Western blots to detect cell-associated Env. In the absence of Rev, NL15E mRNA was efficiently spliced and produced Nef; in the presence of Rev, most of the RNA remained unspliced and produces the Env precursor gp160, which is processed to gp120, the secreted portion of the precursor and gp41.

To allow for the effects of INS to be distinguished and studied separately from splicing, splice sites known to exist within some of the fragments used were eliminated as discussed below. Analysis of the resulting expression vectors included size determination of the produced mRNA, providing the verification that splicing does not interfere with the interpretation of the data.

1.2 Env Expression is Rev-dependent also in the Absence of Functional Splice Sites To study the effect of splicing on env expression, the splice donor at nt 5592 was removed by site-directed mutagenesis (changing GCAGTA to GaAtTc, and thus introducing an EcoRI site), which resulted in plasmid 15ESD- (FIG. 7). The mRNA from this construct was efficiently spliced and produced a small mRNA encoding Nef (FIG. 8). Sequence analysis revealed that this spliced mRNA was generated by the use of an alternative splice donor located at nt 5605 (TACATgtaatg) and the common splice acceptor site at nt 7925. In contrast to published work (Lu et al., Proc. Natl. Acad. Sci. USA 87:7598–7602 (1990), expression of Env from this mutant depended on Rev. Next, the splice acceptor site was mutated at nt 7925. Since previous cDNA cloning had revealed that in addition to the splice acceptor site at nt 7925 there are two additional splice acceptor sites at nt 7897 and nt 7901 (Schwartz, et al. J. Virol. 64:2519–2529 (1990), this region of 43 bp encompassing nt 7884 to nt 7926 was removed. This resulted in plSEDSS (FIG. 7). Northern blot analysis of mRNA from HLtat cells transfected with this construct confirmed that the 15EDSS mRNA is not spliced (FIG. 8B). Although all functional splice sites have been removed from p15EDSS, Rev is still required for Env production (FIG. 8A). Taken together with data obtained by studying gag expression, these results suggest that the presence of inefficiently used splice sites is not the primary determinant for Rev-dependent Env expression. It is known that at least two unused splice sites are present in this mRNA (the alternative splice donor at nt 5605 and the splice donor of exon 6D at nt 6269). Therefore, it cannot be ruled out that initial spliceosome formation can occur, which does not lead to the execution of splicing. It is possible that this is sufficient to retain the mRNA in the nucleus and, since no splicing occurs, that this would lead to degradation of the mRNA. Alternatively, it is possible that splice-site-independent RNA elements similar to those identified within the gag/pol region (INS) are responsible for the Rev dependency (Schwartz et al., J. Virol. 66:7176–7182 (1992); Schwartz et al., J. Virol. 66:150–159(1992).

1.3 Identification of Negative Elements within gp120 mRNA

Figure 9B:
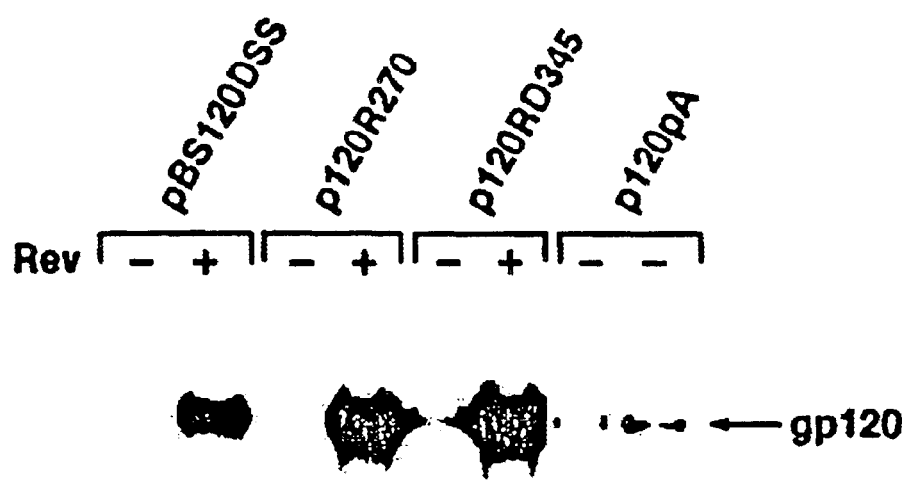

To distinguish between these possibilities, a series of constructs were designed that allowed the determination of the location of such INS elements. First, a stop codon followed by the restriction sites for NruI and MluI was introduced at the cleavage site between the extracellular gp120 and the transmembrane protein gp41 at nt 7301 in plasmid NL15EDSS, resulting in p120DSS (FIG. 7). Immunoprecipitation of gp120 from the medium of cells transfected with p120DSS confirmed the production of high levels of gp120 only in the presence of Rev (FIG. 9B). The release of gp120 is very efficient, since only barely detectable amounts remain associated with the cells (data not shown). This finding rules out the possibility that the translation of the gp41 portion of the env cDNA is responsible for the defect in env expression. Next, the region 3' of the stop codon of gp120 (consisting of gp41, including the RRE and 3' LTR) with the SV40 polyadenylation signal (FIG. 7) was replaced. This construct, p120pA, produced very low levels of gp120 in the absence of Rev (FIG. 9B). Background levels of Env were produced from p120DR (FIG. 7), which was generated from pBS120DSS by removing the 5' portion of gp41 including the RRE (MluI to HpaI at nt 8200) (FIG. 9B). These results demonstrate the presence of a major INS-like sequence within the gp120 portion. To study the effect of Rev on this mRNA, different RREs (RRE330, RRE270, and RRED345 (Solomin et al., J. Virol. 64:6010–6017 (1990) were inserted into p120pA downstream of the gp120 stop codon, resulting in p120R330, p120R270, and p120RD345, respectively (FIG. 7). Immunoprecipitations demonstrated that the presence of Rev in trans and the RRE in cis could rescue the defect in the gp120 expression plasmid. High levels of gp120 were produced from p120R330 (data not shown), p120R27Q, and p120RD345 (FIG. 9B) in the presence of Rev.

Northern blot analysis (FIG. 8A) confirmed the protein data. The presence of Rev resulted in the accumulation of high levels of mRNA produced by pBS120DSS, p120R270, and p120RD345. Low but detectable levels of RNA were produced from p120DpA and p120DR.

2. Identification of INS Elements Located within the env mRNA Regions Using Two Strategies To identify elements that have a down regulatory effect in vivo, fragments of env cDNA were inserted into two different test expression vectors, p19 and p37M1-10D. These vectors contain a strong promoter for rapid detection of the gene product, such as the HIV-1 LTR in the presence of Tat, and an indicator gene that is expressed at high levels and can easily be assayed such as p19$^{gag}$ of RSV or the mutated p37$^{gag}$ gene of HIV-1 (p37M1-10D), neither of which contains any known INS-like elements. Expression vector p19 contains the HIV-1 LTR promoter, the RSV p19$^{gag}$ matrix gene, and HIV-1 sequences starting at KpnI (nt 8561) including the complete 3' LTR (Schwartz, et al., J. Virol. 66:7176–7182 (1992). Upon transfection into HLtat cells high levels of p19$^{gag}$ are constitutively produced and are visualized on Western blots. Expression vector p37M1-10D contains the HIV-1 LTR promoter, the mutant p37gag (M1-10), and the 3' portion of the virus starting at KpnI (nt 8561). Upon transfection into HLtat cells this plasmid constitutively produces p37$^{gag}$ that can be quantitated by the HIV-1 p24$^{gag}$ antigen capture assay.

2.1 Identification of INS Elements Using the RSV gag Expression Vector

INS elements within the gp41 and gp120 portions were identified. To this end, the vector p19 was used and the following fragments (FIG. 10) were inserted: (A) nt 7684 to 7959; (B) nt 7684 to 7884 and nt 7927 to 7959; this is similar to fragment A but has the region of the splice acceptors 7A, 7B and 7 deleted; (C) nt 7595 to 7884 and nt 7927 to 7959, having the splice sites deleted as in B; (D) nt 7939 to 8066; (E) nt 7939 to 8416; (F) nt 8200 to 8561 (HpaI-KpnI); (G) nt 7266 to 7595 containing the intact RRE; (H) nt 5523 to 6190, having the splice donor SD5 deleted.

Fragments A, B, and D did not affect Gag⁻ expression, whereas fragment G (RRE) decreased gag expression approximately 5×. Fragment C, E, and H lowered Gag expression by about 10–20-fold indicating the presence of INS elements.

Interestingly, it was observed that the insertion of element F spanning 350 bp in plasmid p19 abolished production of Gag, indicating the presence of a strong INS within this element. The presence of the RRE in cis and Rev in trans resulted in production of high levels of RSV p19$^{gag}$. Fragment F also had a smaller downregulatory effect on the expression of the INS-corrected p17$^{gag}$ of HIV-1 (p17M1234). These experiments revealed the presence of multiple elements located within the env mRNA that cause inhibition of p19$^{gag}$ expression.

2.2 Elimination of the INS within Fragment F

Six synthetic oligonucleotides (Table 3) were generated that introduced 103 point mutations within this region of 330 nt without affecting the amino acid composition of Env. The mutated fragment F was tested in p19 to verify that the INS elements are destroyed. The introduction of the mutations within oligo#1 only marginally affected the expression of p19$^{gag}$, whereas the presence of all oligos (#1 to #6) completely inactivated the INS effect of fragment F. This is another example that more than one region within an INS element needed to by mutagnenized to eliminate the INS effect.

It is noteworthy that this INS element is present in all the multiply spliced Rev-independent mRNAs, such as tat, rev and nef. Experiments were performed to define the function of fragment F within the class of the small mRNAs by removing this fragment from the tat cDNA. In the context of this mRNA, this element confers only a weak INS effect (3–5- fold inhibition), which suggests that inhibition of expression in env mRNA may require the presence of at least two distinct elements. These results suggested that the INS effect within env is based on multiple interacting components. Alternatively, the relative location and interactions among multiple INS components may be important for the magnitude of the INS effect. Therefore, more than one type of analysis in different vectors may be necessary for the identification and elimination of INS.

2.3. Identification of INS Elements using p37M1-10D Expression Vector

The env coding region was subdivided into different consecutive fragments. These fragments and combinations of thereof were PCR-amplified using oligos as indicated in FIG. 11 and inserted downstream of the mutated p37$^{gag}$ gene in p37M1-10D. The plasmids were transfected into HLtat cells that were harvested the next day and analyzed for p24$^{gag}$ expression. FIG. 11 shows that the presence of fragments 2, 3, 5 as well as the combination 1+2+3 lowered gag expression substantially. Different oligos (Table 4) were synthesized that change the AT-rich domains including the three AATAAA elements located within the env coding region by changing the nucleotide but not the amino acid composition of Env. In a first approach, these oligos 1–19 are being introduced into plasmid p120R270 with the goal or producing gp120 in a Rev-independent manner. Oligonucleotides such as oligos 20–26 will then be introduced into the gp41 portion, the two env portions combined and the complete gp160 expressed in a Rev-independent manner.

EXAMPLE 3

Proto-Oncogene C-Fos

Fragments of the fos gene were inserted into the vector p19 and the expression of the resulting plasmids were analyzed by transfections into HLtat cells. It was found that several fragments inhibited protein expression. A strong INS was identified in the fragment containing nucleotides 3328–3450 ("fragment [3328–3450]") (nucleotides of the fos gene are numbered according to Genebank sequence entry HUMCFOT, ACCESSION # V01512). In addition, a weaker element was identified in the coding region.

To eliminate these INS the following oligonucleotides were synthesized and are used in mutagenesis experiments as specified supra.

To eliminate the INS in the fos non-coding region, the following oligonucleotides, which make changes in the fos non-coding region between nucleotides [3328–3450] (the letters in lower case indicate mutated nucleotides), were synthesized and are used to mutagenize fragment [3328–3450]: mutagenesis experiments as specified supra:

```
#1:
3349-3391
TGAAAACGTTcgcaTGTGTcgcTAcgTTgcTTAcTAAGATGGA
(SEQ ID NO:16)

#2:
3392-3434
TTCTCAGATAccTAgcTTcaTATTgccTTaTTgTCTACCTTGA
(SEQ ID NO:17)
```

These oligonucleotides are used to mutagenize fos fragment [3328–3450] inserted into vectors p19, p17M1234 or p37M1234 and the expression of the resulting plasmids are analyzed after transfection into HLtat cells.

The expression of fos is expected to be increased by the elimination of this INS region.

To further define and eliminate the INS elements in the coding region, additional longer fragments of fos are introduced into vector p37M1234. The INS element in the coding region is first mapped more precisely using this expression vector and is then corrected using the following oligonucleotides:

```
#1
2721-2770
GCCCTGTGAGtaGGCActGAAGGacAGcCAtaCGtaACatACAAGTGCCA        (SEQ ID NO:18)

#2
2670-2720
AGCAGCAGCAATGAaCCTagtagcGAtagcCTgAGtagcCCtACGCTGCTG       (SEQ ID NO:19)

#3
2620-2669
ACCCCGAGGCaGAtagCTTtCCatccTGcGCtGCcGCtCACCGCAAGGGC        (SEQ ID NO:20)

#4
2502-2562
CTGCACAGTGGaagCCTcGGaATGGGcCCtATGGCtACcGAatTGGAaCCaCTGTGCA (SEQ ID NO:21)
CTC
```

The expression of fos is expected to be increased by the elimination of this INS region.

EXAMPLE 4

HIV-1 Pol Gene

Vector p37M1234 was used to eliminate an inhibitory/instability sequence from the pol gene of HIV-1 which had been characterized by A W Cochrane et al., "Identification and characterization of intragenic sequences which repress human immunodeficiency virus structural gene expression", J. Virol. 65:5305–5313 (1991). These investigators suggested that a region in pol (HIV nucleotides 3792–4052), termed CRS, was important for inhibition. A larger fragment spanning this region, which contained nucleotides 3700–4194, was inserted into the vector p37M1234 and its effects on the expression of p37gag from the resulting plasmid (plasmid p37M1234RCRS) (see FIG. 12) was analyzed after transfection into HLtat cells.

Severe inhibition of gag expression (10 fold, see FIG. 13) was observed.

In an effort to eliminate this INS, the following oligonucleotides were synthesized (the letters in lower case indicated mutated nucleotides) and used in mutagenesis experiments.

First, it was observed that one AUUUA potential instability element was within the INS region. This was eliminated by mutagenesis using oligonucleotide M10pol and resulted in plasmid p37M1234RCRSP10. The expression of gag from this plasmid was not improved, demonstrating that elimination of the AUUUA element alone did not eliminate the INS. See FIG. 12. Therefore, additional mutagenesis was performed and it was shown that a combination of mutations introduced in plasmid p37M1234RCRS was necessary and sufficient to produce high levels of gag proteins, which were similar to the plasmid lacking CRS. The mutations necessary for the elimination of the INS are shown in FIG. 13.

The above results demonstrate that HIV-1 pol contains INS elements that can be detected and eliminated with the techniques described.

These results also suggest that regions outside of the minimal inhibitory region in CRS as defined by A. W. Cochrane et al., supra, influence the levels of expression. These results suggest that the RNA structure of the region is important for the inhibition of expression.

TABLE 1

Correspondence between Sequence Identification Numbers and Nucleotides in FIG. 4

| Sequence ID Nos. | FIG. 4 |
|---|---|
| SEQ ID NO: 1 | nucleotides 336–731 |
| SEQ ID NO: 2 | nucleotides 402–452 |
| SEQ ID NO: 3 | nucleotides 536–583, above line |
| SEQ ID NO: 4 | nucleotides 585–634, above line |
| SEQ ID NO: 5 | nucleotides 654–703, above line |
| SEQ ID NO: 6 | nucleotides 402–452, below line (M1) |
| SEQ ID NO: 7 | nucleotides 536–583, below line (M2) |
| SEQ ID NO: 8 | nucleotides 585–634, below line (M3) |
| SEQ ID NO: 9 | nucleotides 654–703, below line (M4) |

TABLE 2

Synthetic oligonucleotides used in the mutagenesis of HIV-1 gag and pol regions

The upper sequence is the wild-type HIV-1 as found in $HIV_{HXB2R}$ while the bottom is the mutant oligonucleotide sequence. The location of the sequence is indicated in parentheses.

```
M5gag (778-824)
CACCTAGAACTTTAAATGCATGGGTAAAAGTAGTAGAAGAGAAGGCT           (SEQ ID NO:22)
         XX X  X  X      X  X  X
CACCTAGAACccTgAAcGCcTGGGTgAAgGTgGTAGAAGAGAAGGCT           (SEQ ID NO:23)
```

TABLE 2-continued

Synthetic oligonucleotides used
in the mutagenesis of HIV-1 gag and pol regions

The upper sequence is the wild-type HIV-1 as
found in HIV$_{HXB2R}$ while the bottom is the mutant
oligonucleotide sequence. The location of the sequence is
indicated in parentheses.

```
M6gag (871-915)
CCACCCCACAAGATTTAAACACCATGCTAAACACAGTGGGGGGAC              (SEQ ID NO:24)
          X  XX X      X   X X     X
CCACCCCACAgGAccTgAACACgATGtTgAACACcGTGGGGGAC               (SEQ ID NO:25)

M7gag (1105-1139)
CAGTAGGAGAAATTTATAAAAGATGGATAATCCTG                         (SEQ ID NO:26)
              X X  X X   X
CAGTAGGAGAgATcTAcAAGAGgTGGATAATCCTG                         (SEQ ID NO:27)

M8gag (1140-1175)
GGATTAAATAAAATAGTAAGAATGTATAGCCCTACC                        (SEQ ID NO:28)
     X  X  X  X   X X
GGATTgAAcAAgATcGTgAGgATGTATAGCCCTACC                        (SEQ ID NO:29)

M9gag (1228-1268)
ACCGGTTCTATAAAACTCTAAGAGCCGAGCAAGCTTCACAG                   (SEQ ID NO:30)
            X   X   X  XX X   X
ACCGGTTCTAcAagACcCTgcGgGCtGAGCAAGCTTCACAG                   (SEQ ID NO:31)

M10gag (1321-1364)
ATTGTAAGACTATTTTAAAAGCATTGGGACCAGCGGCTACACTA                (SEQ ID NO:32)
         X XX X  X  XX X  X
ATTGTAAGACcATcCTgAAgGCtcTcGGcCCAGCGGCTACACTA(SEQ ID NO:33)

M11gag (1416-1466)
AGAGTTTTGGCTGAAGCAATGAGCCAAGTAACAAATTCAGCTACCATAATG         (SEQ ID NO:34)
         X  X  X        X X X X X   X
AGAGTTTTGGCcGAgGCgATGAGCCAgGTgACgAAcTCgGCgACCATAATG         (SEQ ID NO:35)

M12gag (1470-1520)
CAGAGAGGCAATTTTAGGAACCAAAGAAAGATTGTTAAGTGTTTCAATTGT         (SEQ ID NO:36)
         X XX       XX X    X X
CAGAGAGGCAAcTTccGGAACCAgcGgAAGATcGTcAAGTGTTTCAATTGT         (SEQ ID NO:37)

M13gag (1527-1574)
GAAGGGCACACAGCCAGAAATTGCAGGGCCCCTAGGAAAAAGGGCTGT           (SEQ ID NO:38)
            X     X X         XX  X
GAAGGGCACACcGCCAGgAAcTGCcGGGCCCCccGGAAgAAGGGCTGT           (SEQ ID NO:39)

M14gag (1581-1631)
TGTGGAAAGGAAGGACACCAAATGAAAGATTGTACTGAGAGACAGGCTAAT         (SEQ ID NO:40)
          X X    X    X X X  X  X X
TGTGGAAAGGAgGGgCACCAgATGAAgGAcTGcACgGAGcGgCAGGCTAAT         (SEQ ID NO:41)

M0pol (1823-1879)                                           (K to R differ-
                                                            ence
                                                            introduced)
CCCCTCGTCACAATAAAGATAGGGGGCAACTAAAGGAAGCTCTATTAGATACAGGAG   (SEQ ID NO:42)
            X   X   X         X      X  XX X
CCCCTCGTCACAgTAAgGATcGGGGGGCAACTcAAGGAAGCgCTgcTcGATACAGGAG  (SEQ ID NO:43)

M1pol (1936-1987)
GATAGGGGGAATTGGAGGTTTTATCAAAGTAAGACAGTATGATCAGATACTC        (SEQ ID NO:44)
          X X X X X    X X X    X X
GATAGGGGgATcGGgGGcTTcATCAAgGTgAGgCAGTAcGAcCAGATACTC         (SEQ ID NO:45)

M2pol (2105-2152)
CCTATTGAGACTGTACCAGTAAAATTAAAGCCAGGAATGGATGGCCCA            (SEQ ID NO:46)
            X  X X X  X  X   X X
CCTATTGAGACgGTgCCcGTgAAgTTgAAGCCgGGgATGGATGGCCCA            (SEQ ID NO:47)

M3.2pol (2162-2216)
CAATGGCCATTGACAGAAGAAAAAATAAAAGCATTAGTAGAAATTTGTACAGAGA     (SEQ ID NO:48)
             X   X X X X X    X   X
CAATGGCCATTGACgGAAGAgAAgATcAAgGCcTTAGTcGAAATcTGTACAGAGA     (SEQ ID NO:49)

M4pol (2465-2515)
TTCAGGAAGTATACTGCATTTACCATACCTAGTATAAACAATGAGACACCA         (SEQ ID NO:50)
            X X  X X    X X X X         X
TTCAGGAAGTAcACgGCgTTcACCATcCCgAGcATcAACAACGAGACACCA         (SEQ ID NO:51)
```

TABLE 2-continued

Synthetic oligonucleotides used
in the mutagenesis of HIV-1 gag and pol regions

The upper sequence is the wild-type HIV-1 as
found in HIV$_{HXB2R}$ while the bottom is the mutant
oligonucleotide sequence. The location of the sequence is
indicated in parentheses.

```
M5pol                                                            (2873-2921)
TTAGTGGGGAAATTGAATTGGGCAAGTCAGATTTACCCAGGGATTAAAG                (SEQ ID NO:52)
         XX   X   X X   X      X
TTAGTGGGGAAgTGAAcTGGGCgAGcCAGATcTACCCgGGGATTAAAG                 (SEQ ID NO:53)

M6pol (3098-3150)
GGCCAATGGACATATCAAATTTATCAAGAGCCATTTAAAAATCTGAAAACAGG            (SEQ ID NO:54)
            X X X X X       X X X X
GGCCAATGGACgTAcCAgATcTAcCAgGAGCCgTTcAAgAAcCTGAAAACAGG            (SEQ ID NO:55)

M7pol (3242-3290)
TGGGGAAAGACTCCTAAATTTAAACTGCCCATACAAAAGGAAACATGGG                (SEQ ID NO:56)
            X X X X X    X X    X
TGGGGAAAGACgCCgAAgTTcAAgCTGCCCATcCAgAAGGAgACATGGG                (SEQ ID NO:57)

M8pol (3520-3569)
GAAGACTGAGTTACAAGCAATTTATCTAGCTTTGCAGGATTCGGGATTAG               (SEQ ID NO:58)
          X X X X X X XX      X
GAAGACTGAGcTgCAgGCgATcTAcCTgGCgcTGCAGGAcTCGGGATTAG               (SEQ ID NO:59)

M8.2pol (3643-3698)
GTTAGTCAATCAAATAATAGAGCAGTTAATAAAAAAGGAAAAGGTCTATCTGGCAT         (SEQ ID NO:60)
        X   X X      X X X X     X     X
GTTAGTCAAcCAAATcATcGAGCAGcTgATcAAgAAGGAgAAGGTgTATCTGGCAT         (SEQ ID NO:61)

M9pol (3749-3800)
GTCAGTGCTGGAATCAGGAAAGTACTATTTTTAGATGGAATAGATAAGGCCC             (SEQ ID NO:62)
        X   X   X X    XX X X X X
GTCAGTGCTGGgATCcGGAAgGTgCTATTccTgGAcGGgATcGATAAGGCCC             (SEQ ID NO:63)

M9.2pol (3806-3863)
GAACATGAGAAATATCACAGTAATTGGAGAGCAATGGCTAGTGATTTTAACCTGCCAC       (SEQ ID NO:64)
           X X   XXX X   XXX X     X X X X
GAACATGAGAAgTAcCACtccAAcTGGcGcGCtATGGCcAGcGAcTTcAACCTGCCAC       (SEQ ID NO:65)

M10pol (3950-4001)
GGAATATGGCAACTAGATTGTACACATTTAGAAGGAAAAGTTATCCTGGTAG             (SEQ ID NO:66)
          X X X X X XX X X X X
GGAATATGGCAgCTgGAcTgCAcGcAccTgGAgGGgAAgGTgATCCTGGTAG             (SEQ ID NO:67)

M11pol (4031-4096)
GCAGAAGTTATTCCAGCAGAAACAGGGCAGGAAACAGCATATTTTCTTTTAAAATTAG       (SEQ ID NO:68)
-CAGGAAGA X  X  X     X        X  X  X  X  X  XX X   X X
GCAGAAGTTATcCCtGCtGAAACtGGGCAGGAgACcGCcTAcTTcCTgcTcAAAcTcG       (SEQ ID NO:69)
-CAGGAAGA M12pol (4097-4151)
TGGCCAGTAAAAACAATACATACTGACAATGGCAGCAATTTCACCGGTGCTACGG          (SEQ ID NO:70)
         X X X X X      X X     X    X
TGGCCAGTgAAgACgATcCAcACgGACAAcGGaAGCAAcTTCACtGGTGCTACGG          (SEQ ID NO:71)

M13pol (4220-4271)
GGAGTAGTAGAATCTATGAATAAAGAATTAAAGAAAATTATAGGACAGGTAA             (SEQ ID NO:72)
             X   X X XX     X X X
GGAGTAGTAGAATCcATGAAcAAgGAAcTgAAGAAgATcATcGGACAGGTAA             (SEQ ID NO:73)

M12pol-p (4097-4151) (indicates the sequence found in
p37M1234RCRSP10+P12p

TGGCCAGTAAAAACAATACAcACgGACAAcGGaAGCAAcTTCACtGGTGCTACGG          (SEQ ID NO:74)
```

TABLE 3

| Sequences of mutant oligos designed to eliminate the INS effect of fragment F |
|---|
| The six oligonucleotides used to eliminate the INS effect of fragment F (oligos #1 to #6) are set forth above in Example 2 (SEQ. ID. NOS. 10–15). |

TABLE 4

Sequence of mutant oligos designed to destroy INS elements within the env coding region The wildtype (top) and the mutant oligo (below) of 26 different regions are shown. mutant oligos for env of HIV-1:

```
M1 (5834-5878) 46-mer
CTTGGGATGTTGATGATCTGTAGTGCTACAGAAAAATTGTGGGTC          (SEQ ID NO:75)
         X       X  X  X  X  X  X  XX
CTTGGGATGcTGATGATcTGcAGcGCcACcGAgAAgcTGTGGGTC          (SEQ ID NO:76)

M2 (5886-5908) 24-mer
ATTATGGGGTACCTGTGTGGAAG                                (SEQ ID NO:77)
       X  X  X
ATTATGGcGTgCCcGTGTGGAAG                                (SEQ ID NO:78)

M3 (5920-5956) 38-mer
CACTCTATTTTGTGCATCAGATGCTAAAGCATATGAT                  (SEQ ID NO:79)
         X  X  X  X  X  X  X
CACTCTATTcTGcGCcTCcGAcGCcAAgGCATATGAT                  (SEQ ID NO:80)

M4 (5957-5982) 27-mer
ACAGAGGTACATAATGTTTGGGCCAC                             (SEQ ID NO:81)
        X  X  X  X
ACAGAGGTgCAcAAcGTcTGGGCCAC                             (SEQ ID NO:82)

M5 (6006-6057) 53-mer
CCAACCCACAAGAAGTAGTATTGGTAAATGTGACAGAAAATTTTAACATGTG   (SEQ ID NO:83)
       X  X  X  X  XX    X  X     X  X  X  X
CCAACCCcCAgGAgGTgGTgcTGGTgAAcGTGACcGAgAAcTTcAACATGTG   (SEQ ID NO:84)

M6 (6135-6179) 46-mer
TAACCCCACTCTGTGTTAGTTTAAAGTGCACTGATTTGAAGAATG          (SEQ ID NO:85)
       X     X  X  XX X        X  XX
TAACCCCcCTCTGcGTgAGccTgAAGTGCACcGAccTGAAGAATG          (SEQ ID NO:86)

M7 (6251-6280) 31-mer
ATCAGCACAAGCATAAGAGGTAAGGTGCAG                         (SEQ ID NO:87)
        X     XX X  X
ATCAGCACcAGCATccGcGGcAAGGTGCAG                         (SEQ ID NO:88)

M8 (6284-6316) 34-mer
GAATATGCATTTTTTTATAAACTTGATATAATA                      (SEQ ID NO:89)
        X  X  X  X  X  X
GAATATGCcTTcTTcTAcAAgCTgGATATAATA                      (SEQ ID NO: 90)

M9 (6317-6343) (28-mer)
CCAATAGATAATGATACTACCAGCTAT                            (SEQ ID NO:91)
       X   X  X  X
CCAATAGcTAAgGAcACcACCAGCTAT                            (SEQ ID NO:92)

M10 (6425-6469) (46-mer)
GCCCCGGCTGGTTTTGCGATTCTAAAATGTAATAATAAGACGTTC          (SEQ ID NO:93)
        X  X  X     X  X  X  X  X  X
GCCCCGGCcGGcTTcGCGATcCTgAAgTGcAAcAAcAAGACGTTC          (SEQ ID NO:94)

M11 (6542-6583) (42-mer)
GAACTGCTGTTAAATGGCAGTCTAGCAGAAGAAGAGGTAGTA             (SEQ ID NO:95)
         X X  X     X  X  X  X  X
CAACTGCTGcTgAAcGGCAGcCTgGCcGAgGAgGAGGTAGTA             (SEQ ID NO:96)

M12 (6590-6624) (35-mer)
TCTGTCAATTTCACGGACAATGCTAAAACCATAAT                    (SEQ ID NO:97)
```

TABLE 4-continued

Sequence of mutant oligos designed to
destroy INS elements within the env coding region The wildtype (top) and the mutant oligo (below)
of 26 different regions are shown.
mutant oligos for env of HIV-1:

```
         X  X    X X X
TCTGCCAAcTTCAccGACAAcGCcAAgACCATAAT                    (SEQ ID NO:98)

M13 (6632-6663) (32-mer)
CTGAACACATCTGTAGAAATTAATTGTACAAG                       (SEQ ID NO:99)
      X  X  X X  X X
CTGAACCAgTCcGTgGAgATcAAcTGTACAAG                       (SEQ ID NO:100)

M14 (6667-6697) (31-mer)
CAACAACAATACAAGAAAAAGAATCCGTATC                        (SEQ ID NO:101)
         X  X  X  XX X
CAACAACAAcACcGGcAAgcGcATCCGTATC                        (SEQ ID NO:102)

M15 (6806-6852) (47-mer)
GCTAGCAAATTAAGAGAACAATTTGGAAATAATAAAACAATAATCTT        (SEQ ID NO:103)
         XX XX X  X  X  X X X X  X
GCTAGCAAgcTgcGcGAgcCAgTACGGgAAcAAcAAgACcATAATCTT       (SEQ ID NO:104)

M16 (nt 6917-6961) (45-mer)
TTCTACTGTAATTCAACACAACTGTTTAATAGTACTTGGTTTAAT          (SEQ ID NO:105)
          X  X  X  X  X       X  X  X  X
TTCTACTGgAAcTCcACcCAgCTGTTcAAcAGcACcTGGTTTAAT          (SEQ ID NO:106)

M17 (nt 7006-7048) (43-mer)
CACAATCACCCTCCCATGCAGAATAAAACAAATTATAAACATG            (SEQ ID NO:107)
          X  X  X   X X X X X
CACAATCACcCTgCCcTGCcGcATCAAgCAgATCATAAACATG            (SEQ ID NO:108)

M18 (nt 7084-7129) (46-mer)
CATCAGTGGACAAATTAGATGTTCATCAAATATTACAGGGCTGCTA         (SEQ ID NO:109)
          X  X  XX X  X X X  X  X  X  X
CATCAGCGGcCAgATccGcTGcTCcTCcAAcATcACcGGGCTGCTA         (SEQ ID NO:110)

M19 (nt 7195-7252) (58-mer)
GAGGGACAATTGGAGAAGTGAATTATATAAATATAAAGTAGTAAAAATTGAACCATTA   (SEQ ID NO:111)
          X     X  X  XX X  X  X  X  X  X  X  X
GAGGGACAAcTGGAGgAGcGAgcTgTAcAAgTAcAAgGTgGTgAAgATcGAACCATTA   (SEQ ID NO:112)

M20 (nt 7594-7633) (40-mer)
GCCTTGGAATGCTAGTTGGAGTAATAAATCTCTGGAACAG               (SEQ ID NO:113)
          X  X  X     X  X X  X
GCCTTGGAAcGCcAGcTGGAGcAAcAAgTCcCTGGAACAG               (SEQ ID NO:114)

M21 (nt 7658-7689) (32-mer)
GAGTGGGACAGAGAAATTAACAATTACACAAG                       (SEQ ID NO:115)
           X X X X   X
GAGTGGGACcGcGAgATcAACAAcTACACAAG                       (SEQ ID NO:116)

M22 (nt 7694-7741) (48-mer)
ATACACTCCTTAATTGAAGAATCGCAAAACCAGCAAGAAAAGAATGAA       (SEQ ID NO:117)
           X  X  X  X  X  X     X  X  X
ATACACTCCcTgATcGAgGAgTCcCAgAACCAgCAgGAgAAGAATGAA       (SEQ ID NO:118)

M23 (nt 7954-7993) (40-mer)
CAGGCCCGAAGGAATAGAAGAAGAAGGTGGAGAGAGAGAC               (SEQ ID NO:119)
           X  X  X  X  X  X  X
CAGGCCCGAgGGcATcGAgGAgGAgGGcGGcGAGAGAGAC               (SEQ ID NO:120)

M24 (nt 8072-8121) (50-mer)
TACCACCGCTTGAGAGACTTACTCTTGATTGTAACGAGGATTGTGGAACT     (SEQ ID NO:121)
           X  XX  XX  X   X X        X
TACCACCGCcTGcGcGACcTgCTCcTGATcGTgACGAGGATcGTGGAACT     (SEQ ID NO:122)

M25 (nt 8136-8179) (44-mer)
GGTGGGAAGCCCTCAAATATTGGTGGAATCTCCTACAGTATTGG           (SEQ ID NO:123)
            X     X X     X     X
GGTGGGAgGCCCTCAAgTAcTGGTGGAAcCTCCTcCAGTATTGG           (SEQ ID NO:124)
```

TABLE 4-continued

Sequence of mutant oligos designed to destroy INS elements within the env coding region The wildtype (top) and the mutant oligo (below) of 26 different regions are shown. mutant oligos for env of HIV-1:

```
M26 (nt 8180-8219) (40-mer)
AGTCAGGAACTAAAGAATAGTGCTGTTAGCTTGCTCAATG                (SEQ ID NO:125)
        X  X     X  X  X  X X X
AGTCAGGAgCTgAAGAAcAGcGCcGTgAaCcTGCTCAATG                (SEQ ID NO:126)
```

Comments:
Although the vast majority of oligonucleotides follow the HXB2 sequence, some exceptions are noted:
In oligo M15, nt 6807 follows the pNL43 sequence. (Specifically, nt 6807 is C in NL43 but A in HBX2.) Oligo M26 has the nucleotide sequence derived from pNL43.

EXAMPLE 5

Use of or P37M1-10D or P5SM1-13P0 in Immunoprophylaxis or Immunotherapy

In postnatal gene therapy, new genetic information has been introduced into tissues by indirect means such as removing target cells from the body, infecting them with viral vectors carrying the new genetic information, and then reimplanting them into the body; or by direct means such as encapsulating formulations of DNA in liposomes; entrapping DNA in proteoliposomes containing viral envelope receptor proteins; calcium phosphate co-precipitating DNA; and coupling DNA to a polylysine-glycoprotein carrier complex. In addition, in vivo infectivity of cloned viral DNA sequences after direct intrahepatic injection with or without formation of calcium phosphate coprecipitates has also been described. mRNA sequences containing elements that enhance stability have also been shown to be efficiently translated in *Xenopus laevis* embryos, with the use of cationic lipid vesicles. See, e.g., J. A. Wolff, et al., *Science* 247:1465–1468 (1990) and references cited therein.

Recently, it has also been shown that injection of pure RNA or DNA directly into skeletal muscle results in significant expression of genes within the muscle cells. J. A. Wolff, et al., *Science* 247:1465–1468 (1990). Forcing RNA or DNA introduced into muscle cells by other means such as by particle-acceleration (N. -S. Yang, et al. *Proc. Natl. Acad. Sci. USA* 87:9568–9572 (1990); S. R. Williams et al., *Proc. Natl. Acad. Sci. USA* 88:2726–2730 (1991)) or by viral transduction should also allow the DNA or RNA to be stably maintained and expressed. In the experiments reported in Wolff et al., RNA or DNA vectors were used to express reporter genes in mouse skeletal muscle cells, specifically cells of the quadriceps muscles. Protein expression was readily detected and no special delivery system was required for these effects. Polynucleotide expression was also obtained when the composition and volume of the injection fluid and the method of injection were modified from the described protocol. For example, reporter enzyme activity was reported to have been observed with 10 to 100 μl of hypotonic, isotonic, and hypertonic sucrose solutions, Opti-MEM, or sucrose solutions containing 2mM $CaCl_2$ and also to have been observed when the 10- to 100-μl injections were performed over 20 min. with a pump instead of within 1 min.

Enzymatic activity from the protein encoded by the reporter gene was also detected in abdominal muscle injected with the RNA or DNA vectors, indicating that other muscles can take up and express polynucleotides. Low amounts of reporter enzyme were also detected in other tissues (liver, spleen, skin, lung, brain and blood) injected with the RNA and DNA vectors. Intramuscularly injected plasmid DNA has also been demonstrated to be stably expressed in non-human primate muscle. S. Jiao et al., *Hum. Gene Therapy* 3:21–33 (1992).

It has been proposed that the direct transfer of genes into human muscle in situ may have several potential clinical applications. Muscle is potentially a suitable tissue for the heterologous expression of a transgene that would modify disease states in which muscle is not primarily involved, in addition to those in which it is. For example, muscle tissue could be used for the heterologous expression of proteins that can immunize, be secreted in the blood, or clear a circulating toxic metabolite. The use of RNA and a tissue that can be repetitively accessed might be useful for a reversible type of gene transfer, administered much like conventional pharmaceutical treatments. See J. A. Wolff, et al., *Science* 247:1465–1468 (1990) and S. Jiao et al., *Hum. Gene Therapy* 3:21–33 (1992).

It had been proposed by J. A. Wolff et al., supra, that the intracellular expression of genes encoding antigens might provide alternative approaches to vaccine development. This hypothesis has been supported by a recent report that plasmid DNA encoding influenza A nucleoprotein injected into the quadriceps of BALB/c mice resulted in the generation of influenza A nucleoprotein-specific cytotoxic T lymphocytes (CTLs) and protection from a subsequent challenge with a heterologous strain of influenza A virus, as measured by decreased viral lung titers, inhibition of mass loss, and increased survival. J. B. Ulmer et al., *Science* 259:1745–1749 (1993).

Therefore, it appears that the direct injection of RNA or DNA vectors encoding the viral antigen can be used for endogenous expression of the antigen to generate the viral antigen for presentation to the immune system without the need for self-replicating agents or adjuvants, resulting in the generation of antigen-specific CTLs and protection from a subsequent challenge with a homologous or heterologous strain of virus.

CTLs in both mice and humans are capable of recognizing epitopes derived from conserved internal viral proteins and are thought to be important in the immune response against viruses. By recognition of epitopes from conserved viral proteins, CTLs may provide cross-strain protection. CTLs specific for conserved viral antigens can respond to different strains of virus, in contrast to antibodies, which are generally strain-specific.

Thus, direct injection of RNA or DNA encoding the viral antigen has the advantage of being without some of the limitations of direct peptide delivery or viral vectors. See J. A. Ulmer et al., supra, and the discussions and references therein). Furthermore, the generation of high-titer antibodies to expressed proteins after injection of DNA indicates that this may be a facile and effective means of making antibody-based vaccines targeted towards conserved or non-conserved antigens, either separately or in combination with CTL vaccines targeted towards conserved antigens. These may also be used with traditional peptide vaccines, for the generation of combination vaccines. Furthermore, because protein expression is maintained after DNA injection, the persistence of B and T cell memory may be enhanced, thereby engendering long-lived humoral and cell-mediated immunity.

1. Vectors for the Immunoprophylaxis or Immunotherapy against HIV-1

The mutated gag genomic sequences in vectors p37M1-10D or p55M1-13P0 (FIG. 6) will be inserted in expression vectors using a strong constitutive promoter such as CMV or RSV, or an inducible promoter such as HIV-1.

The vector will be introduced into animals or humans in a pharmaceutically acceptable carrier using one of several techniques such as injection of DNA directly into human tissues; electroporation or transfection of the DNA into primary human cells in culture (ex vivo), selection of cells for desired properties and reintroduction of such cells into the body, (said selection can be for the successful homologous recombination of the incoming DNA to an appropriate preselected genomic region); generation of infectious particles containing the gag gene, infection of cells ex vivo and reintroduction of such cells into the body; or direct infection by said particles in vivo.

Substantial levels of protein will be produced leading to an efficient stimulation of the immune system.

In another embodiment of the invention, the described constructs will be modified to express mutated gag proteins that are unable to participate in virus particle formation. It is expected that such gag proteins will stimulate the immune system to the same extent as the wild-type gag protein, but be unable to contribute to increased HIV-1 production. This modification should result in safer vectors for immunotherapy and immunophrophylaxis.

EXAMPLE 6

Inhibition of HIV-1 Expression Using Transdominant (TD)- TD-GAG-TD REV OR TD GAG-PRO-TD REV GENES Direct injection of DNA or use of vectors other than retroviral vectors will allow the constitutive high level of trans-dominant gag (TDgag) in cells. In addition, the approach taken by B. K. Felber et al., *Science* 239:184–187 (1988) will allow the generation of retroviral vectors, e.g. mouse-derived retroviral vectors, encoding HIV-1 TDgag, which will not interfere with the infection of human cells by the retroviral vectors. In the approach of Felber, et al., supra, it was shown that fragments of the HIV-1 LTR containing the promoter and part of the polyA signal can be incorporated without detrimental effects within mouse retroviral vectors and remain transcriptionally silent. The presence of Tat protein stimulated transcription from the HIV-1 LTR and resulted in the high level expression of genes linked to the HIV-1 LTR.

The generation of hybrid TDgag-TDRev or TDgag-pro-TDRev genes and the introduction of expression vectors in human cells will allow the efficient production of two proteins that will inhibit HIV-1 expression. The incorporation of two TD proteins in the same vector is expected to amplify the effects of each one on viral replication. The use of the HIV-1 promoter in a matter similar to one described in B. K. Felber, et al., supra, will allow high level gag and rev expression in infected cells. In the absence of infection, expression will be substantially lower. Alternatively, the use of other strong promoters will allow the constitutive expression of such proteins. This approach could be highly beneficial, because of the production of a highly immunogenic gag, which is not able to participate in the production of infectious virus, but which, in fact, antagonizes such production. This can be used as an efficient immuniprophylactic or immunotherapeutic approach against AIDS.

Examples of trans-dominant mutants are described in Trono et al., *Cell* 59:112–120 (1989).

1. Generation of Constructs Encoding Transdominant gag Mutant Proteins

Gag mutant proteins that can act as trans-dominant mutants, as described, for example, in Trono et al., supra, will be generated by modifying vector p37M1-10D or p55M1-13P0 to produce transdominant gag proteins at high constitutive levels.

The transdominant gag protein will stimulate the immune system and will inhibit the production of infectious virus, but will not contribute to the production of infectious virus.

The added safety of this approach makes it more acceptable for human application.

Those skilled in the art will recognize that any gene encoding a mRNA containing an inhibitory/instability sequence or sequences can be modified in accordance with the exemplified methods of this invention or their functional equivalents.

Modifications of the above described modes for carrying out the invention that are obvious to those of skill in the fields of genetic engineering, protein chemistry, medicine, and related fields are intended to be within the scope of the following claims.

Every reference cited hereinbefore is hereby incorporated by reference in its entirety.

What is claimed is:

1. A synthetic gene encoding a HIV-1 gag or HIV-1 env protein normally expressed in an eukaryotic cell wherein at least one rarely-used or less preferred codon in a natural gene encoding said protein has been replaced by a preferred codon encoding the same amino acid, and wherein said rarely-used or less preferred codon contains an inhibitory/instability region, said synthetic gene expressing said protein at a level which is higher than that expressed by said natural gene in an in vitro mammalian cell culture system under identical conditions.

2. An expression vector comprising the synthetic gene of claim 1.

3. A mammalian cell comprising the synthetic gene of claim 2.

4. A method for preparing a synthetic gene encoding a protein normally expressed by mammalian cells, comprising identifying rarely-used and less-preferred codons containing an inhibitory/instability region in the natural gene encoding said protein and replacing one or more of said rarely-used or less-preferred codons with a preferred codon encoding the same amino acid as the replaced codon, so that a synthetic gene is prepared.

* * * * *

SEQUENCE LISTING (1) GENERAL INFORMATION:

(iii) NUMBER OF SEQUENCES: 130

(2) INFORMATION FOR SEQ ID NO: 1:

```
        (i) SEQUENCE CHARACTERISTICS:
            (A) LENGTH: 396 BASE PAIRS
            (B) TYPE: NUCLEIC ACID
            (C) STRANDEDNESS: SINGLE
            (D) TOPOLOGY: LINEAR (xi) SEQUENCE DESCRIPTION:SEQ ID NO: 1:

ATGGGTGCGA GAGCGTCAGT ATTAAGCGGG GGAGAATTAG ATCGATGGGA AAAAATTCGG      60

TTAAGGCCAG GGGGAAAGAA AAAATATAAA TTAAAACATA TAGTATGGGC AAGCAGGGAG     120

CTAGAACGAT TCGCAGTTAA TCCTGGCCTG TTAGAAACAT CAGAAGGCTG TAGACAAATA     180

CTGGGACAGC TACAACCATC CCTTCAGACA GGATCAGAAG AACTTAGATC ATTATATAAT     240

ACAGTAGCAA CCCTCTATTG TGTGCATCAA AGGATAGAGA TAAAAGACAC CAAGGAAGCT     300

TTAGACAAGA TAGAGGAAGA GCAAAACAAA AGTAAGAAAA AAGCACAGCA AGCAGCAGCT     360

GACACAGGAC ACAGCAATCA GGTCAGCCAA AATTAC                              396

(2) INFORMATION FOR SEQ ID NO: 2:

(i) SEQUENCE CHARACTERISTICS:
            (A) LENGTH: 51 BASE PAIRS
            (B) TYPE: NUCLEIC ACID
            (C) STRANDEDNESS: SINGLE
            (D) TOPOLOGY: LINEAR (xi) SEQUENCE DESCRIPTION:SEQ ID NO: 2:

CCAGGGGGAA AGAAAAAATA TAAATTAAAA CATATAGTAT GGGCAAGCAG G               51

(2) INFORMATION FOR SEQ ID NO: 3:

(i) SEQUENCE CHARACTERISTICS:
            (A) LENGTH: 48 BASE PAIRS
            (B) TYPE: NUCLEIC ACID
            (C) STRANDEDNESS: SINGLE
            (D) TOPOLOGY: LINEAR (xi) SEQUENCE DESCRIPTION:SEQ ID NO: 3:

CCTTCAGACA GGATCAGAAG AACTTAGATC ATTATATAAT ACAGTAGC                   48

(2) INFORMATION FOR SEQ ID NO: 4:

(i) SEQUENCE CHARACTERISTICS:
            (A) LENGTH: 50 BASE PAIRS
            (B) TYPE: NUCLEIC ACID
            (C) STRANDEDNESS: SINGLE
            (D) TOPOLOGY: LINEAR (xi) SEQUENCE DESCRIPTION:SEQ ID NO: 4:

ACCCTCTATT GTGTGCATCA AAGGATAGAG ATAAAAGACA CCAAGGAAGC                 50

(2) INFORMATION FOR SEQ ID NO: 5:

(i) SEQUENCE CHARACTERISTICS:
            (A) LENGTH: 50 BASE PAIRS
            (B) TYPE: NUCLEIC ACID
            (C) STRANDEDNESS: SINGLE
            (D) TOPOLOGY: LINEAR (xi) SEQUENCE DESCRIPTION:SEQ ID NO: 5:

GAGCAAAACA AAAGTAAGAA AAAAGCACAG CAAGCAGCAG CTGACACAGG                 50

(2) INFORMATION FOR SEQ ID NO: 6:

(i) SEQUENCE CHARACTERISTICS:
```

(A) LENGTH: 51 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 6:

CCAGGGGGAA AGAAGAAGTA CAAGCTAAAG CACATCGTAT GGGCAAGCAG G          51

(2) INFORMATION FOR SEQ ID NO: 7:

(i) SEQUENCE CHARACTERISTICS:
        (A) LENGTH: 48 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 7:

CCTTCAGACA GGATCAGAGG AGCTTCGATC ACTATACAAC ACAGTAGC              48

(2) INFORMATION FOR SEQ ID NO: 8:

(i) SEQUENCE CHARACTERISTICS:
        (A) LENGTH: 50 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 8:

ACCCTCTATT GTGTGCACCA GCGGATCGAG ATCAAGGACA CCAAGGAAGC            50

(2) INFORMATION FOR SEQ ID NO: 9:

(i) SEQUENCE CHARACTERISTICS:
        (A) LENGTH: 50 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 9:

GAGCAAAACA AGTCCAAGAA GAAGGCCCAG CAGGCAGCAG CTGACACAGG            50

(2) INFORMATION FOR SEQ ID NO: 10:

(i) SEQUENCE CHARACTERISTICS:
        (A) LENGTH: 68 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 10:

GAATAGTGCT GTTAACCTCC TGAACGCTAC CGCTATCGCC GTGGCGGAAG GAACCGACAG    60

GGTTATAG                                                            68

(2) INFORMATION FOR SEQ ID NO: 11:

(i) SEQUENCE CHARACTERISTICS:
        (A) LENGTH: 62 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 11:

AAGTATTACA AGCCGCCTAC CGCGCCATCA GACATATCCC CCGCCGCATC CGCCAGGGCT    60
TG                                                                  62

(2) INFORMATION FOR SEQ ID NO: 12:

(i) SEQUENCE CHARACTERISTICS:
        (A) LENGTH: 58 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 12:

```
GCTATAAGAT GGGCGGTAAA TGGAGCAAGT CCTCCGTCAT CGGCTGGCCT GCTGTAAG          58
```

(2) INFORMATION FOR SEQ ID NO: 13:

(i) SEQUENCE CHARACTERISTICS:
        (A) LENGTH: 58 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 13:

```
GGAAAGAATG CGCAGGGCCG AACCCGCCGC CGACGGAGTT GGCGCCGTAT CTCGAGAC          58
```

(2) INFORMATION FOR SEQ ID NO: 14:

(i) SEQUENCE CHARACTERISTICS:
        (A) LENGTH: 62 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 14:

```
CTAGAAAAAC ACGGCGCCAT TACCTCCTCT AACACCGCCG CCAATAACGC CGCTTGTGCC        60
TG                                                                      62
```

(2) INFORMATION FOR SEQ ID NO: 15:

(i) SEQUENCE CHARACTERISTICS:
        (A) LENGTH: 60 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 15:

```
GCTAGAAGCA CAGGAAGAAG AGGAAGTCGG CTTCCCCGTT ACCCCTCAGG TACCTTTAAG        60
```

(2) INFORMATION FOR SEQ ID NO: 16:

(i) SEQUENCE CHARACTERISTICS:
        (A) LENGTH: 43 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 16:

```
TGAAAACGTT CGCATGTGTC GCTACGTTGC TTACTAAGAT GGA                         43
```

(2) INFORMATION FOR SEQ ID NO: 17:

(i) SEQUENCE CHARACTERISTICS:
        (A) LENGTH: 43 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 17:

```
TTCTCAGATA CCTAGCTTCA TATTGCCTTA TTGTCTACCT TGA                         43
```

(2) INFORMATION FOR SEQ ID NO: 18:

(i) SEQUENCE CHARACTERISTICS:
        (A) LENGTH: 50 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 18:

```
GCCCTGTGAG TAGGCACTGA AGGACAGCCA TACGTAACAT ACAAGTGCCA         50
```

(2) INFORMATION FOR SEQ ID NO: 19:

(i) SEQUENCE CHARACTERISTICS:
        (A) LENGTH: 51 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 19:

```
AGCAGCAGCA ATGAACCTAG TAGCGATAGC CTGAGTAGCC CTACGCTGCT G       51
```

(2) INFORMATION FOR SEQ ID NO: 20:

(i) SEQUENCE CHARACTERISTICS:
        (A) LENGTH: 50 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 20:

```
ACCCCGAGGC AGATAGCTTT CCATCCTGCG CTGCCGCTCA CCGCAAGGGC         50
```

(2) INFORMATION FOR SEQ ID NO: 21:

(i) SEQUENCE CHARACTERISTICS:
        (A) LENGTH: 61 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 21:

```
CTGCACAGTG GAAGCCTCGG AATGGGCCCT ATGGCTACCG AATTGGAACC ACTGTGCACT C   61
```

(2) INFORMATION FOR SEQ ID NO: 22:

(i) SEQUENCE CHARACTERISTICS:
        (A) LENGTH: 47 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 22:

```
CACCTAGAAC TTTAAATGCA TGGGTAAAAG TAGTAGAAGA GAAGGCT           47
```

(2) INFORMATION FOR SEQ ID NO: 23:

(i) SEQUENCE CHARACTERISTICS:
        (A) LENGTH: 47 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 23:

```
CACCTAGAAC CCTGAACGCC TGGGTGAAGG TGGTAGAAGA GAAGGCT           47
```

(2) INFORMATION FOR SEQ ID NO: 24:

(i) SEQUENCE CHARACTERISTICS:
        (A) LENGTH: 45 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 24:

CCACCCCACA AGATTTAAAC ACCATGCTAA ACACAGTGGG GGGAC                45

(2) INFORMATION FOR SEQ ID NO: 25:

(i) SEQUENCE CHARACTERISTICS:
        (A) LENGTH: 45 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 25:

CCACCCCACA GGACCTGAAC ACGATGTTGA ACACCGTGGG GGGAC                45

(2) INFORMATION FOR SEQ ID NO: 26:

(i) SEQUENCE CHARACTERISTICS:
        (A) LENGTH: 35 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 26:

CAGTAGGAGA AATTTATAAA AGATGGATAA TCCTG                35

(2) INFORMATION FOR SEQ ID NO: 27:

(i) SEQUENCE CHARACTERISTICS:
        (A) LENGTH: 35 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 27:

CAGTAGGAGA GATCTACAAG AGGTGGATAA TCCTG                35

(2) INFORMATION FOR SEQ ID NO: 28:

(i) SEQUENCE CHARACTERISTICS:
        (A) LENGTH: 36 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 28:

GGATTAAATA AAATAGTAAG AATGTATAGC CCTACC                36

(2) INFORMATION FOR SEQ ID NO: 29:

(i) SEQUENCE CHARACTERISTICS:
        (A) LENGTH: 36 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 29:

GGATTGAACA AGATCGTGAG GATGTATAGC CCTACC                36

(2) INFORMATION FOR SEQ ID NO: 30:

(i) SEQUENCE CHARACTERISTICS:
        (A) LENGTH: 41 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 30:

ACCGGTTCTA TAAAACTCTA AGAGCCGAGC AAGCTTCACA G                            41

(2) INFORMATION FOR SEQ ID NO: 31:

(i) SEQUENCE CHARACTERISTICS:
        (A) LENGTH: 41 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 31:

ACCGGTTCTA CAAGACCCTG CGGGCTGAGC AAGCTTCACA G                            41

(2) INFORMATION FOR SEQ ID NO: 32:

(i) SEQUENCE CHARACTERISTICS:
        (A) LENGTH: 44 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 32:

ATTGTAAGAC TATTTTAAAA GCATTGGGAC CAGCGGCTAC ACTA                         44

(2) INFORMATION FOR SEQ ID NO: 33:

(i) SEQUENCE CHARACTERISTICS:
        (A) LENGTH: 44 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 33:

ATTGTAAGAC CATCCTGAAG GCTCTCGGCC CAGCGGCTAC ACTA                         44

(2) INFORMATION FOR SEQ ID NO: 34:

(i) SEQUENCE CHARACTERISTICS:
        (A) LENGTH: 51 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 34:

AGAGTTTTGG CTGAAGCAAT GAGCCAAGTA ACAAATTCAG CTACCATAAT G                 51

(2) INFORMATION FOR SEQ ID NO: 35:

(i) SEQUENCE CHARACTERISTICS:
        (A) LENGTH: 51 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 35:

AGAGTTTTGG CCGAGGCGAT GAGCCAGGTG ACGAACTCGG CGACCATAAT G                 51

(2) INFORMATION FOR SEQ ID NO: 36:

(i) SEQUENCE CHARACTERISTICS:
        (A) LENGTH:  51 BASE PAIRS
        (B) TYPE:  NUCLEIC ACID
        (C) STRANDEDNESS:  SINGLE
        (D) TOPOLOGY:  LINEAR (xi) SEQUENCE DESCRIPTION:  SEQ ID NO: 36:

CAGAGAGGCA ATTTTAGGAA CCAAAGAAAG ATTGTTAAGT GTTTCAATTG T            51

(2) INFORMATION FOR SEQ ID NO: 37:

(i) SEQUENCE CHARACTERISTICS:
        (A) LENGTH:  51 BASE PAIRS
        (B) TYPE:  NUCLEIC ACID
        (C) STRANDEDNESS:  SINGLE
        (D) TOPOLOGY:  LINEAR (xi) SEQUENCE DESCRIPTION:  SEQ ID NO: 37:

CAGAGAGGCA ACTTCCGGAA CCAGCGGAAG ATCGTCAAGT GTTTCAATTG T            51

(2) INFORMATION FOR SEQ ID NO: 38:

(i) SEQUENCE CHARACTERISTICS:
        (A) LENGTH:  48 BASE PAIRS
        (B) TYPE:  NUCLEIC ACID
        (C) STRANDEDNESS:  SINGLE
        (D) TOPOLOGY:  LINEAR (xi) SEQUENCE DESCRIPTION:  SEQ ID NO: 38:

GAAGGGCACA CAGCCAGAAA TTGCAGGGCC CCTAGGAAAA AGGGCTGT               48

(2) INFORMATION FOR SEQ ID NO: 39:

(i) SEQUENCE CHARACTERISTICS:
        (A) LENGTH:  48 BASE PAIRS
        (B) TYPE:  NUCLEIC ACID
        (C) STRANDEDNESS:  SINGLE
        (D) TOPOLOGY:  LINEAR (xi) SEQUENCE DESCRIPTION:  SEQ ID NO: 39:

GAAGGGCACA CCGCCAGGAA CTGCCGGGCC CCCCGGAAGA AGGGCTGT               48

(2) INFORMATION FOR SEQ ID NO: 40:

(i) SEQUENCE CHARACTERISTICS:
        (A) LENGTH:  51 BASE PAIRS
        (B) TYPE:  NUCLEIC ACID
        (C) STRANDEDNESS:  SINGLE
        (D) TOPOLOGY:  LINEAR (xi) SEQUENCE DESCRIPTION:  SEQ ID NO: 40:

TGTGGAAAGG AAGGACACCA AATGAAAGAT TGTACTGAGA GACAGGCTAA T            51

(2) INFORMATION FOR SEQ ID NO: 41:

(i) SEQUENCE CHARACTERISTICS:
        (A) LENGTH:  51 BASE PAIRS
        (B) TYPE:  NUCLEIC ACID
        (C) STRANDEDNESS:  SINGLE
        (D) TOPOLOGY:  LINEAR (xi) SEQUENCE DESCRIPTION:  SEQ ID NO: 41:

TGTGGAAAGG AGGGGCACCA GATGAAGGAC TGCACGGAGC GGCAGGCTAA T            51

(2) INFORMATION FOR SEQ ID NO: 42:

(i) SEQUENCE CHARACTERISTICS:

(A) LENGTH: 58 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 42:

CCCCTCGTCA CAATAAAGAT AGGGGGGCAA CTAAAGGAAG CTCTATTAGA TACAGGAG        58

(2) INFORMATION FOR SEQ ID NO: 43:

(i) SEQUENCE CHARACTERISTICS:
        (A) LENGTH: 58 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 43:

CCCCTCGTCA CAGTAAGGAT CGGGGGGCAA CTCAAGGAAG CGCTGCTCGA TACAGGAG        58

(2) INFORMATION FOR SEQ ID NO: 44:

(i) SEQUENCE CHARACTERISTICS:
        (A) LENGTH: 52 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 44:

GATAGGGGGA ATTGGAGGTT TTATCAAAGT AAGACAGTAT GATCAGATAC TC        52

(2) INFORMATION FOR SEQ ID NO: 45:

(i) SEQUENCE CHARACTERISTICS:
        (A) LENGTH: 52 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 45:

GATAGGGGGG ATCGGGGGCT TCATCAAGGT GAGGCAGTAC GACCAGATAC TC        52

(2) INFORMATION FOR SEQ ID NO: 46:

(i) SEQUENCE CHARACTERISTICS:
        (A) LENGTH: 48 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 46:

CCTATTGAGA CTGTACCAGT AAAATTAAAG CCAGGAATGG ATGGCCCA        48

(2) INFORMATION FOR SEQ ID NO: 47:

(i) SEQUENCE CHARACTERISTICS:
        (A) LENGTH: 48 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 47:

CCTATTGAGA CGGTGCCCGT GAAGTTGAAG CCGGGGATGG ATGGCCCA        48

(2) INFORMATION FOR SEQ ID NO: 48:

(i) SEQUENCE CHARACTERISTICS:
        (A) LENGTH: 55 BASE PAIRS (B) TYPE:  NUCLEIC ACID
            (C) STRANDEDNESS:  SINGLE
            (D) TOPOLOGY:  LINEAR (xi) SEQUENCE DESCRIPTION:  SEQ ID NO: 48:

CAATGGCCAT TGACAGAAGA AAAAATAAAA GCATTAGTAG AAATTTGTAC AGAGA          55

(2) INFORMATION FOR SEQ ID NO: 49:

(i) SEQUENCE CHARACTERISTICS:
            (A) LENGTH:  55 BASE PAIRS
            (B) TYPE:  NUCLEIC ACID
            (C) STRANDEDNESS:  SINGLE
            (D) TOPOLOGY:  LINEAR (xi) SEQUENCE DESCRIPTION:  SEQ ID NO: 49:

CAATGGCCAT TGACGGAAGA GAAGATCAAG GCCTTAGTCG AAATCTGTAC AGAGA          55

(2) INFORMATION FOR SEQ ID NO: 50:

(i) SEQUENCE CHARACTERISTICS:
            (A) LENGTH:  51 BASE PAIRS
            (B) TYPE:  NUCLEIC ACID
            (C) STRANDEDNESS:  SINGLE
            (D) TOPOLOGY:  LINEAR (xi) SEQUENCE DESCRIPTION:  SEQ ID NO: 50:

TTCAGGAAGT ATACTGCATT TACCATACCT AGTATAAACA ATGAGACACC A              51

(2) INFORMATION FOR SEQ ID NO: 51:

(i) SEQUENCE CHARACTERISTICS:
            (A) LENGTH:  51 BASE PAIRS
            (B) TYPE:  NUCLEIC ACID
            (C) STRANDEDNESS:  SINGLE
            (D) TOPOLOGY:  LINEAR (xi) SEQUENCE DESCRIPTION:  SEQ ID NO: 51:

TTCAGGAAGT ACACGGCGTT CACCATCCCG AGCATCAACA ACGAGACACC A              51

(2) INFORMATION FOR SEQ ID NO: 52:

(i) SEQUENCE CHARACTERISTICS:
            (A) LENGTH:  49 BASE PAIRS
            (B) TYPE:  NUCLEIC ACID
            (C) STRANDEDNESS:  SINGLE
            (D) TOPOLOGY:  LINEAR (xi) SEQUENCE DESCRIPTION:  SEQ ID NO: 52:

TTAGTGGGGA AATTGAATTG GGCAAGTCAG ATTTACCCAG GGATTAAAG                 49

(2) INFORMATION FOR SEQ ID NO: 53:

(i) SEQUENCE CHARACTERISTICS:
            (A) LENGTH:  49 BASE PAIRS
            (B) TYPE:  NUCLEIC ACID
            (C) STRANDEDNESS:  SINGLE
            (D) TOPOLOGY:  LINEAR (xi) SEQUENCE DESCRIPTION:  SEQ ID NO: 53:

TTAGTGGGGA AGGTGAACTG GGCGAGCCAG ATCTACCCGG GGATTAAAG                 49

(2) INFORMATION FOR SEQ ID NO: 54:

(i) SEQUENCE CHARACTERISTICS:
            (A) LENGTH:  53 BASE PAIRS
            (B) TYPE:  NUCLEIC ACID

```
        (C) STRANDEDNESS:  SINGLE
        (D) TOPOLOGY:  LINEAR (xi) SEQUENCE DESCRIPTION:  SEQ ID NO: 54:

GGCCAATGGA CATATCAAAT TTATCAAGAG CCATTTAAAA ATCTGAAAAC AGG          53

(2) INFORMATION FOR SEQ ID NO: 55:

(i) SEQUENCE CHARACTERISTICS:
        (A) LENGTH:  53 BASE PAIRS
        (B) TYPE:  NUCLEIC ACID
        (C) STRANDEDNESS:  SINGLE
        (D) TOPOLOGY:  LINEAR (xi) SEQUENCE DESCRIPTION:  SEQ ID NO: 55:

GGCCAATGGA CGTACCAGAT CTACCAGGAG CCGTTCAAGA ACCTGAAAAC AGG          53

(2) INFORMATION FOR SEQ ID NO: 56:

(i) SEQUENCE CHARACTERISTICS:
        (A) LENGTH:  49 BASE PAIRS
        (B) TYPE:  NUCLEIC ACID
        (C) STRANDEDNESS:  SINGLE
        (D) TOPOLOGY:  LINEAR (xi) SEQUENCE DESCRIPTION:  SEQ ID NO: 56:

TGGGGAAAGA CTCCTAAATT TAAACTGCCC ATACAAAAGG AAACATGGG              49

(2) INFORMATION FOR SEQ ID NO: 57:

(i) SEQUENCE CHARACTERISTICS:
        (A) LENGTH:  49 BASE PAIRS
        (B) TYPE:  NUCLEIC ACID
        (C) STRANDEDNESS:  SINGLE
        (D) TOPOLOGY:  LINEAR (xi) SEQUENCE DESCRIPTION:  SEQ ID NO: 57:

TGGGGAAAGA CGCCGAAGTT CAAGCTGCCC ATCCAGAAGG AGACATGGG              49

(2) INFORMATION FOR SEQ ID NO: 58:

(i) SEQUENCE CHARACTERISTICS:
        (A) LENGTH:  50 BASE PAIRS
        (B) TYPE:  NUCLEIC ACID
        (C) STRANDEDNESS:  SINGLE
        (D) TOPOLOGY:  LINEAR (xi) SEQUENCE DESCRIPTION:  SEQ ID NO: 58:

GAAGACTGAG TTACAAGCAA TTTATCTAGC TTTGCAGGAT TCGGGATTAG             50

(2) INFORMATION FOR SEQ ID NO: 59:

(i) SEQUENCE CHARACTERISTICS:
        (A) LENGTH:  50 BASE PAIRS
        (B) TYPE:  NUCLEIC ACID
        (C) STRANDEDNESS:  SINGLE
        (D) TOPOLOGY:  LINEAR (xi) SEQUENCE DESCRIPTION:  SEQ ID NO: 59:

GAAGACTGAG CTGCAGGCGA TCTACCTGGC GCTGCAGGAC TCGGGATTAG             50

(2) INFORMATION FOR SEQ ID NO: 60:

(i) SEQUENCE CHARACTERISTICS:
        (A) LENGTH:  56 BASE PAIRS
        (B) TYPE:  NUCLEIC ACID
        (C) STRANDEDNESS:  SINGLE
```

(D) TOPOLOGY: LINEAR (xi) SEQUENCE DESCRIPTION: SEQ ID NO: 60:

GTTAGTCAAT CAAATAATAG AGCAGTTAAT AAAAAAGGAA AAGGTCTATC TGGCAT         56

(2) INFORMATION FOR SEQ ID NO: 61:

(i) SEQUENCE CHARACTERISTICS:
        (A) LENGTH: 56 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 61:

GTTAGTCAAC CAAATCATCG AGCAGCTGAT CAAGAAGGAG AAGGTGTATC TGGCAT         56

(2) INFORMATION FOR SEQ ID NO: 62:

(i) SEQUENCE CHARACTERISTICS:
        (A) LENGTH: 52 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 62:

GTCAGTGCTG GAATCAGGAA AGTACTATTT TTAGATGGAA TAGATAAGGC CC             52

(2) INFORMATION FOR SEQ ID NO: 63:

(i) SEQUENCE CHARACTERISTICS:
        (A) LENGTH: 52 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 63:

GTCAGTGCTG GGATCCGGAA GGTGCTATTC CTGGACGGGA TCGATAAGGC CC             52

(2) INFORMATION FOR SEQ ID NO: 64:

(i) SEQUENCE CHARACTERISTICS:
        (A) LENGTH: 58 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 64:

GAACATGAGA AATATCACAG TAATTGGAGA GCAATGGCTA GTGATTTTAA CCTGCCAC       58

(2) INFORMATION FOR SEQ ID NO: 65:

(i) SEQUENCE CHARACTERISTICS:
        (A) LENGTH: 58 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 65:

GAACATGAGA AGTACCACTC CAACTGGCGC GCTATGGCCA GCGACTTCAA CCTGCCAC       58

(2) INFORMATION FOR SEQ ID NO: 66:

(i) SEQUENCE CHARACTERISTICS:
        (A) LENGTH: 52 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 66:

GGAATATGGC AACTAGATTG TACACATTTA GAAGGAAAAG TTATCCTGGT AG        52

(2) INFORMATION FOR SEQ ID NO: 67:

(i) SEQUENCE CHARACTERISTICS:
        (A) LENGTH: 52 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 67:

GGAATATGGC AGCTGGACTG CACGCACCTG GAGGGGAAGG TGATCCTGGT AG        52

(2) INFORMATION FOR SEQ ID NO: 68:

(i) SEQUENCE CHARACTERISTICS:
        (A) LENGTH: 66 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 68:

GCAGAAGTTA TTCCAGCAGA AACAGGGCAG GAAACAGCAT ATTTTCTTTT AAAATTAGCA    60

GGAAGA                                                              66

(2) INFORMATION FOR SEQ ID NO: 69:

(i) SEQUENCE CHARACTERISTICS:
        (A) LENGTH: 66 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 69:

GCAGAAGTTA TCCCTGCTGA AACTCGGCAG GAGACCGCCT ACTTCCTGCT CAAACTCGCA    60

GGAAGA                                                              66

(2) INFORMATION FOR SEQ ID NO: 70:

(i) SEQUENCE CHARACTERISTICS:
        (A) LENGTH: 55 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 70:

TGGCCAGTAA AAACAATACA TACTGACAAT GGCAGCAATT TCACCGGTGC TACGG    55

(2) INFORMATION FOR SEQ ID NO: 71:

(i) SEQUENCE CHARACTERISTICS:
        (A) LENGTH: 55 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 71:

TGGCCAGTGA AGACGATCCA CACGGACAAC GGAAGCAACT TCACTGGTGC TACGG    55

(2) INFORMATION FOR SEQ ID NO: 72:

(i) SEQUENCE CHARACTERISTICS:
        (A) LENGTH: 52 BASE PAIRS (B) TYPE: NUCLEIC ACID
        (C) STRANDEDNESS: SINGLE
        (D) TOPOLOGY: LINEAR (xi) SEQUENCE DESCRIPTION: SEQ ID NO: 72:

GGAGTAGTAG AATCTATGAA TAAAGAATTA AAGAAAATTA TAGGACAGGT AA          52

(2) INFORMATION FOR SEQ ID NO: 73:

(i) SEQUENCE CHARACTERISTICS:
        (A) LENGTH: 52 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 73:

GGAGTAGTAG AATCCATGAA CAAGGAACTG AAGAAGATCA TCGGACAGGT AA          52

(2) INFORMATION FOR SEQ ID NO: 74:

(i) SEQUENCE CHARACTERISTICS:
        (A) LENGTH: 55 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 74:

TGGCCAGTAA AAACAATACA CACGGACAAC GGAAGCAACT TCACTGGTGC TACGG       55

(2) INFORMATION FOR SEQ ID NO: 75:

(i) SEQUENCE CHARACTERISTICS:
        (A) LENGTH: 45 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 75:

CTTGGGATGT TGATGATCTG TAGTGCTACA GAAAAATTGT GGGTC                  45

(2) INFORMATION FOR SEQ ID NO: 76:

(i) SEQUENCE CHARACTERISTICS:
        (A) LENGTH: 45 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 76:

CTTGGGATGC TGATGATCTG CAGCGCCACC GAGAAGCTGT GGGTC                  45

(2) INFORMATION FOR SEQ ID NO: 77:

(i) SEQUENCE CHARACTERISTICS:
        (A) LENGTH: 23 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 77:

ATTATGGGGT ACCTGTGTGG AAG                                          23

(2) INFORMATION FOR SEQ ID NO: 78:

(i) SEQUENCE CHARACTERISTICS:
        (A) LENGTH: 23 BASE PAIRS
        (B) TYPE: NUCLEIC ACID

```
        (C) STRANDEDNESS: SINGLE
        (D) TOPOLOGY: LINEAR (xi) SEQUENCE DESCRIPTION: SEQ ID NO: 78:

ATTATGGCGT GCCCGTGTGG AAG                                          23

(2) INFORMATION FOR SEQ ID NO: 79:

(i) SEQUENCE CHARACTERISTICS:
        (A) LENGTH: 37 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 79:

CACTCTATTT TGTGCATCAG ATGCTAAAGC ATATGAT                            37

(2) INFORMATION FOR SEQ ID NO: 80:

(i) SEQUENCE CHARACTERISTICS:
        (A) LENGTH: 37 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 80:

CACTCTATTC TGCGCCTCCG ACGCCAAGGC ATATGAT                            37

(2) INFORMATION FOR SEQ ID NO: 81:

(i) SEQUENCE CHARACTERISTICS:
        (A) LENGTH: 26 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 81:

ACAGAGGTAC ATAATGTTTG GGCCAC                                       26

(2) INFORMATION FOR SEQ ID NO: 82:

(i) SEQUENCE CHARACTERISTICS:
        (A) LENGTH: 26 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 82:

ACAGAGGTGC ACAACGTCTG GGCCAC                                       26

(2) INFORMATION FOR SEQ ID NO: 83:

(i) SEQUENCE CHARACTERISTICS:
        (A) LENGTH: 52 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 83:

CCAACCCACA AGAAGTAGTA TTGGTAAATG TGACAGAAAA TTTTAACATG TG           52

(2) INFORMATION FOR SEQ ID NO: 84:

(i) SEQUENCE CHARACTERISTICS:
        (A) LENGTH: 52 BASE PAIRS
        (B) TYPE: NUCLEIC ACID
        (C) STRANDEDNESS: SINGLE
```

(D) TOPOLOGY: LINEAR (xi) SEQUENCE DESCRIPTION: SEQ ID NO: 84:

CCAACCCCCA GGAGGTGGTG CTGGTGAACG TGACCGAGAA CTTCAACATG TG                52

(2) INFORMATION FOR SEQ ID NO: 85:

(i) SEQUENCE CHARACTERISTICS:
        (A) LENGTH: 45 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 85:

TAACCCCACT CTGTGTTAGT TTAAAGTGCA CTGATTTGAA GAATG                        45

(2) INFORMATION FOR SEQ ID NO: 86:

(i) SEQUENCE CHARACTERISTICS:
        (A) LENGTH: 45 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 86:

TAACCCCCCT CTGCGTGAGC CTGAAGTGCA CCGACCTGAA GAATG                        45

(2) INFORMATION FOR SEQ ID NO: 87:

(i) SEQUENCE CHARACTERISTICS:
        (A) LENGTH: 30 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 87:

ATCAGCACAA GCATAAGAGG TAAGGTGCAG                                         30

(2) INFORMATION FOR SEQ ID NO: 88:

(i) SEQUENCE CHARACTERISTICS:
        (A) LENGTH: 30 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 88:

ATCAGCACCA GCATCCGCGG CAAGGTGCAG                                         30

(2) INFORMATION FOR SEQ ID NO: 89:

(i) SEQUENCE CHARACTERISTICS:
        (A) LENGTH: 33 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 89:

GAATATGCAT TTTTTTATAA ACTTGATATA ATA                                     33

(2) INFORMATION FOR SEQ ID NO: 90:

(i) SEQUENCE CHARACTERISTICS:
        (A) LENGTH: 33 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 90:

GAATATGCCT TCTTCTACAA GCTGGATATA ATA                          33

(2) INFORMATION FOR SEQ ID NO: 91:

(i) SEQUENCE CHARACTERISTICS:
        (A) LENGTH: 27 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 91:

CCAATAGATA ATGATACTAC CAGCTAT                                 27

(2) INFORMATION FOR SEQ ID NO: 92:

(i) SEQUENCE CHARACTERISTICS:
        (A) LENGTH: 27 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 92:

CCAATAGCTA AGGACACCAC CAGCTAT                                 27

(2) INFORMATION FOR SEQ ID NO: 93:

(i) SEQUENCE CHARACTERISTICS:
        (A) LENGTH: 45 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 93:

GCCCCGGCTG GTTTTGCGAT TCTAAAATGT AATAATAAGA CGTTC             45

(2) INFORMATION FOR SEQ ID NO: 94:

(i) SEQUENCE CHARACTERISTICS:
        (A) LENGTH: 45 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 94:

GCCCCGGCCG GCTTCGCGAT CCTGAAGTGC AACAACAAGA CGTTC             45

(2) INFORMATION FOR SEQ ID NO: 95:

(i) SEQUENCE CHARACTERISTICS:
        (A) LENGTH: 42 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 95:

CAACTGCTGT TAAATGGCAG TCTAGCAGAA GAAGAGGTAG TA                42

(2) INFORMATION FOR SEQ ID NO: 96:

(i) SEQUENCE CHARACTERISTICS:
        (A) LENGTH: 42 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 96:

CAACTGCTGC TGAACGGCAG CCTGGCCGAG GAGGAGGTAG TA                                42

(2) INFORMATION FOR SEQ ID NO: 97:

(i) SEQUENCE CHARACTERISTICS:
        (A) LENGTH: 35 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 97:

TCTGTCAATT TCACGGACAA TGCTAAAACC ATAAT                                         35

(2) INFORMATION FOR SEQ ID NO: 98:

(i) SEQUENCE CHARACTERISTICS:
        (A) LENGTH: 35 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 98:

TCTGCCAACT TCACCGACAA CGCCAAGACC ATAAT                                         35

(2) INFORMATION FOR SEQ ID NO: 99:

(i) SEQUENCE CHARACTERISTICS:
        (A) LENGTH: 32 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 99:

CTGAACACAT CTGTAGAAAT TAATTGTACA AG                                            32

(2) INFORMATION FOR SEQ ID NO: 100:

(i) SEQUENCE CHARACTERISTICS:
        (A) LENGTH: 32 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 100:

CTGAACCAGT CCGTGGAGAT CAACTGTACA AG                                            32

(2) INFORMATION FOR SEQ ID NO: 101:

(i) SEQUENCE CHARACTERISTICS:
        (A) LENGTH: 31 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 101:

CAACAACAAT ACAAGAAAAA GAATCCGTAT C                                             31

(2) INFORMATION FOR SEQ ID NO: 102:

(i) SEQUENCE CHARACTERISTICS:
        (A) LENGTH: 31 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 102:

CAACAACAAC ACCGGCAAGC GCATCCGTAT C                                31

(2) INFORMATION FOR SEQ ID NO: 103:

(i) SEQUENCE CHARACTERISTICS:
        (A) LENGTH: 47 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 103:

GCTAGCAAAT TAAGAGAACA ATTTGGAAAT AATAAAACAA TAATCTT                47

(2) INFORMATION FOR SEQ ID NO: 104:

(i) SEQUENCE CHARACTERISTICS:
        (A) LENGTH: 47 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 104:

GCTAGCAAGC TGCGCGAGCA GTACGGGAAC AACAAGACCA TAATCTT                47

(2) INFORMATION FOR SEQ ID NO: 105:

(i) SEQUENCE CHARACTERISTICS:
        (A) LENGTH: 45 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 105:

TTCTACTGTA ATTCAACACA ACTGTTTAAT AGTACTTGGT TTAAT                  45

(2) INFORMATION FOR SEQ ID NO: 106:

(i) SEQUENCE CHARACTERISTICS:
        (A) LENGTH: 45 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 106:

TTCTACTGGA ACTCCACCCA GCTGTTCAAC AGCACCTGGT TTAAT                  45

(2) INFORMATION FOR SEQ ID NO: 107:

(i) SEQUENCE CHARACTERISTICS:
        (A) LENGTH: 43 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 107:

CACAATCACC CTCCCATGCA GAATAAAACA AATTATAAAC ATG                    43

(2) INFORMATION FOR SEQ ID NO: 108:

(i) SEQUENCE CHARACTERISTICS:
        (A) LENGTH: 43 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 108:

```
CACAATCACC CTGCCCTGCC GCATCAAGCA GATCATAAAC ATG                    43
```

(2) INFORMATION FOR SEQ ID NO: 109:

(i) SEQUENCE CHARACTERISTICS:
        (A) LENGTH: 46 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 109:

```
CATCAGTGGA CAAATTAGAT GTTCATCAAA TATTACAGGG CTGCTA                 46
```

(2) INFORMATION FOR SEQ ID NO: 110:

(i) SEQUENCE CHARACTERISTICS:
        (A) LENGTH: 46 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 110:

```
CATCAGCGGC CAGATCCGCT GCTCCTCCAA CATCACCGGG CTGCTA                 46
```

(2) INFORMATION FOR SEQ ID NO: 111:

(i) SEQUENCE CHARACTERISTICS:
        (A) LENGTH: 58 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 111:

```
GAGGGACAAT TGGAGAAGTG AATTATATAA ATATAAAGTA GTAAAAATTG AACCATTA    58
```

(2) INFORMATION FOR SEQ ID NO: 112:

(i) SEQUENCE CHARACTERISTICS:
        (A) LENGTH: 58 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 112:

```
GAGGGACAAC TGGAGGAGCG AGCTGTACAA GTACAAGGTG GTGAAGATCG AACCATTA    58
```

(2) INFORMATION FOR SEQ ID NO: 113:

(i) SEQUENCE CHARACTERISTICS:
        (A) LENGTH: 40 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 113:

```
GCCTTGGAAT GCTAGTTGGA GTAATAAATC TCTGGAACAG                        40
```

(2) INFORMATION FOR SEQ ID NO: 114:

(i) SEQUENCE CHARACTERISTICS:
        (A) LENGTH: 40 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 114:

```
GCCTTGGAAC GCCAGCTGGA GCAACAAGTC CCTGGAACAG                        40
```

(2) INFORMATION FOR SEQ ID NO: 115:

(i) SEQUENCE CHARACTERISTICS:
        (A) LENGTH: 32 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 115:

GAGTGGGACA GAGAAATTAA CAATTACACA AG                              32

(2) INFORMATION FOR SEQ ID NO: 116:

(i) SEQUENCE CHARACTERISTICS:
        (A) LENGTH: 32 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 116:

GAGTGGGACC GCGAGATCAA CAACTACACA AG                              32

(2) INFORMATION FOR SEQ ID NO: 117:

(i) SEQUENCE CHARACTERISTICS:
        (A) LENGTH: 48 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 117:

ATACACTCCT TAATTGAAGA ATCGCAAAAC CAGCAAGAAA AGAATGAA             48

(2) INFORMATION FOR SEQ ID NO: 118:

(i) SEQUENCE CHARACTERISTICS:
        (A) LENGTH: 48 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 118:

ATACACTCCC TGATCGAGGA GTCCCAGAAC CAGCAGGAGA AGAATGAA             48

(2) INFORMATION FOR SEQ ID NO: 119:

(i) SEQUENCE CHARACTERISTICS:
        (A) LENGTH: 40 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 119:

CAGGCCCGAA GGAATAGAAG AAGAAGGTGG AGAGAGAGAC                      40

(2) INFORMATION FOR SEQ ID NO: 120:

(i) SEQUENCE CHARACTERISTICS:
        (A) LENGTH: 40 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 120:

CAGGCCCGAG GGCATCGAGG AGGAGGGCGG CGAGAGAGAC                      40

(2) INFORMATION FOR SEQ ID NO: 121:

(i) SEQUENCE CHARACTERISTICS:
        (A) LENGTH: 50 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 121:

```
TACCACCGCT TGAGAGACTT ACTCTTGATT GTAACGAGGA TTGTGGAACT          50
```

(2) INFORMATION FOR SEQ ID NO: 122:

(i) SEQUENCE CHARACTERISTICS:
        (A) LENGTH: 50 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 122:

```
TACCACCGCC TGCGCGACCT GCTCCTGATC GTGACGAGGA TCGTGGAACT          50
```

(2) INFORMATION FOR SEQ ID NO: 123:

(i) SEQUENCE CHARACTERISTICS:
        (A) LENGTH: 44 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 123:

```
GGTGGGAAGC CCTCAAATAT TGGTGGAATC TCCTACAGTA TTGG                44
```

(2) INFORMATION FOR SEQ ID NO: 124:

(i) SEQUENCE CHARACTERISTICS:
        (A) LENGTH: 44 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 124:

```
GGTGGGAGGC CCTCAAGTAC TGGTGGAACC TCCTCCAGTA TTGG                44
```

(2) INFORMATION FOR SEQ ID NO: 125:

(i) SEQUENCE CHARACTERISTICS:
        (A) LENGTH: 40 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 125:

```
AGTCAGGAAC TAAAGAATAG TGCTGTTAGC TTGCTCAATG                     40
```

(2) INFORMATION FOR SEQ ID NO: 126:

(i) SEQUENCE CHARACTERISTICS:
        (A) LENGTH: 40 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 126:

```
AGTCAGGAGC TGAAGAACAG CGCCGTGAAC CTGCTCAATG                     40
```

(2) INFORMATION FOR SEQ ID NO: 127:

(i) SEQUENCE CHARACTERISTICS:
        (A) LENGTH: 495 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 127:

```
GGTACCAGCA CACAAAGGAA TTGGAGGAAA TGAACAAGTA GATAAATTAG TCAGTGCTGG      60
AATCAGGAAA GTACTATTTT TAGATGGAAT AGATAAGGCC CAAGATGAAC ATGAGAAATA     120
TCACAGTAAT TGGAGAGCAA TGGCTAGTGA TTTTAACCTG CCACCTGTAG TAGCAAAAGA     180
AATAGTAGCC AGCTGTGATA AATGTCAGCT AAAAGGAGAA GCCATGCATG GACAAGTAGA     240
CTGTAGTCCA GGAATATGGC AACTAGATTG TACACATTTA GAAGGAAAAG TTATCCTGGT     300
AGCAGTTCAT GTAGCCAGTG GATATATAGA AGCAGAAGTT ATTCCAGCAG AAACAGGGCA     360
GGAAACAGCA TATTTTCTTT TAAAATTAGC AGGAAGATGG CCAGTAAAAA CAATACATAC     420
TGACAATGGC AGCAATTTCA CCGGTGCTAC GGTTAGGGCC GCCTGTTGGT GGGCGGGAAT     480
CAAGCAGGAA TTTGG                                                      495
```

(2) INFORMATION FOR SEQ ID NO: 128:

(i) SEQUENCE CHARACTERISTICS:
        (A) LENGTH: 7228 BASE PAIRS
        (B) TYPE: NUCLEIC ACID
        (C) STRANDEDNESS: SINGLE
        (D) TOPOLOGY: LINEAR (xi) SEQUENCE DESCRIPTION: SEQ ID NO: 128:

```
TGGAAGGGCT AATTTGGTCC CAAAAAAGAC AAGAGATCCT TGATCTGTGG ATCTACCACA      60
CACAAGGCTA CTTCCCTGAT TGGCAGAACT ACACACCAGG GCCAGGGATC AGATATCCAC     120
TGACCTTTGG ATGGTGCTTC AAGTTAGTAC CAGTTGAACC AGAGCAAGTA GAAGAGGCCA     180
AATAAGGAGA GAAGAACAGC TTGTTACACC CTATGAGCCA GCATGGGATG GAGGACCCGG     240
AGGGAGAAGT ATTAGTGTGG AAGTTTGACA GCCTCCTAGC ATTTCGTCAC ATGGCCCGAG     300
AGCTGCATCC GGAGTACTAC AAAGACTGCT GACATCGAGC TTTCTACAAG GGACTTTCCG     360
CTGGGGACTT TCCAGGGAGG TGTGGCCTGG GCGGGACTGG GGAGTGGCGA GCCCTCAGAT     420
GCTACATATA AGCAGCTGCT TTTTGCCTGT ACTGGGTCTC TCTGGTTAGA CCAGATCTGA     480
GCCTGGGAGC TCTCTGGCTA ACTAGGGAAC CCACTGCTTA AGCCTCAATA AAGCTTGCCT     540
TGAGTGCTCA AGTAGTGTG TGCCCGTCTG TTGTGTGACT CTGGTAACTA GAGATCCCTC     600
AGACCCTTTT AGTCAGTGTG GAAAATCTCT AGCAGTGGCG CCCGAACAGG ACTTGAAAG     660
CGAAAGTAAA GCCAGAGGAG ATCTCTCGAC GCAGGACTCG GCTTGCTGAA GCGCGCGTCG     720
ACAGAGAGAT GGGTGCGAGA GCGTCAGTAT TAAGCGGGGG AGAATTAGAT CGATGGGAAA     780
AAATTCGGTT AAGGCCAGGG GGAAAGAAGA AGTACAAGCT AAAGCACATC GTATGGGCAA     840
GCAGGGAGCT AGAACGATTC GCAGTTAATC CTGGCCTGTT AGAAACATCA GAAGGCTGTA     900
GACAAATACT GGGACAGCTA CAACCATCCC TTCAGACAGG ATCAGAGGAG CTTCGATCAC     960
TATACAACAC AGTAGCAACC CTCTATTGTG TGCACCAGCG GATCGAGATC AAGGACACCA    1020
AGGAAGCTTT AGACAAGATA GAGGAAGAGC AAAACAAGTC CAAGAAGAAG GCCCAGCAGG    1080
CAGCAGCTGA CACAGGACAC AGCAATCAGG TCAGCCAAAA TTACCCTATA GTGCAGAACA    1140
TCCAGGGGCA AATGGTACAT CAGGCCATAT CACCTAGAAC TTTAAATGCA TGGGTAAAAG    1200
```

```
TAGTAGAAGA GAAGGCTTTC AGCCCAGAAG TGATACCCAT GTTTTCAGCA TTATCAGAAG    1260

GAGCCACCCC ACAGGACCTG AACACGATGT TGAACACCGT GGGGGGACAT CAAGCAGCCA    1320

TGCAAATGTT AAAAGAGACC ATCAATGAGG AAGCTGCAGA ATGGGATAGA GTGCATCCAG    1380

TGCATGCAGG GCCTATTGCA CCAGGCCAGA TGAGAGAACC AAGGGGAAGT GACATAGCAG    1440

GAACTACTAG TACCCTTCAG GAACAAATAG GATGGATGAC AAATAATCCA CCTATCCCAG    1500

TAGGAGAGAT CTACAAGAGG TGGATAATCC TGGGATTGAA CAAGATCGTG AGGATGTATA    1560

GCCCTACCAG CATTCTGGAC ATAAGACAAG GACCAAAGGA ACCCTTTAGA GACTATGTAG    1620

ACCGGTTCTA TAAAACTCTA AGAGCTGAGC AAGCTTCACA GGAGGTAAAA AATTGGATGA    1680

CAGAAACCTT GTTGGTCCAA AATGCGAACC CAGATTGTAA GACCATCCTG AAGGCTCTCG    1740

GCCCAGCGGC TACACTAGAA GAAATGATGA CAGCATGTCA GGGAGTAGGA GGACCCGGCC    1800

ATAAGGCAAG AGTTTTGTAG GGATCCACTA GTTCTAGACT CGAGGGGGGG CCCGGTACCT    1860

TTAAGACCAA TGACTTACAA GGCAGCTGTA GATCTTAGCC ACTTTTTAAA AGAAAAGGGG    1920

GGACTGGAAG GGCTAATTCA CTCCCAAAGA AGACAAGATA TCCTTGATCT GTGGATCTAC    1980

CACACACAAG GCTACTTCCC TGATTGGCAG AACTACACAC CAGGGCCAGG GGTCAGATAT    2040

CCACTGACCT TTGGATGGTG CTACAAGCTA GTACCAGTTG AGCCAGATAA GGTAGAAGAG    2100

GCCAATAAAG GAGAGAACAC CAGCTTGTTA CACCCTGTGA GCCTGCATGG AATGGATGAC    2160

CCTGAGAGAG AAGTGTTAGA GTGGAGGTTT GACAGCCGCC TAGCATTTCA TCACGTGGCC    2220

CGAGAGCTGC ATCCGGAGTA CTTCAAGAAC TGCTGACATC GAGCTTGCTA CAAGGGACTT    2280

TCCGCTGGGG ACTTTCCAGG GAGGCGTGGC CTGGGCGGGA CTGGGGAGTG GCGAGCCCTC    2340

AGATGCTGCA TATAAGCAGC TGCTTTTTGC CTGTACTGGG TCTCTCTGGT TAGACCAGAT    2400

CTGAGCCTGG GAGCTCTCTG GCTAACTAGG GAACCCACTG CTTAAGCCTC AATAAAGCTT    2460

GCCTTGAGTG CTTCAAGTAG TGTGTGCCCG TCTGTTGTGT GACTCTGGTA ACTAGAGATC    2520

CCTCAGACCC TTTTAGTCAG TGTGGAAAAT CTCTAGCACC CCCCAGGAGG TAGAGGTTGC    2580

AGTGAGCCAA GATCGCGCCA CTGCATTCCA GCCTGGGCAA GAAAACAAGA CTGTCTAAAA    2640

TAATAATAAT AAGTTAAGGG TATTAAATAT ATTTATACAT GGAGGTCATA AAAATATATA    2700

TATTTGGGCT GGGCGCAGTG GCTCACACCT GCGCCCGGCC CTTTGGGAGG CCGAGGCAGG    2760

TGGATCACCT GAGTTTGGGA GTTCCAGACC AGCCTGACCA ACATGGAGAA ACCCCTTCTC    2820

TGTGTATTTT TAGTAGATTT TATTTTATGT GTATTTTATT CACAGGTATT TCTGGAAAAC    2880

TGAAACTGTT TTTCCTCTAC TCTGATACCA CAAGAATCAT CAGCACAGAG GAAGACTTCT    2940

GTGATCAAAT GTGGTGGGAG AGGGAGGTTT TCACCAGCAC ATGAGCAGTC AGTTCTGCCG    3000

CAGACTCGGC GGGTGTCCTT CGGTTCAGTT CCAACACCGC CTGCCTGGAG AGAGGTCAGA    3060

CCACAGGGTG AGGGCTCAGT CCCCAAGACA TAAACACCCA AGACATAAAC ACCCAACAGG    3120

TCCACCCCGC CTGCTGCCCA GGCAGAGCCG ATTCACCAAG ACGGGAATTA GGATAGAGAA    3180

AGAGTAAGTC ACACAGAGCC GGCTGTGCGG GAGAACGGAG TTCTATTATG ACTCAAATCA    3240

GTCTCCCCAA GCATTCGGGG ATCAGAGTTT TTAAGGATAA CTTAGTGTGT AGGGGGCCAG    3300

TGAGTTGGAG ATGAAAGCGT AGGGAGTCGA AGGTGTCCTT TTGCGCCGAG TCAGTTCCTG    3360

GGTGGGGGCC ACAAGATCGG ATGAGCCAGT TTATCAATCC GGGGGTGCCA GCTGATCCAT    3420

GGAGTGCAGG GTCTGCAAAA TATCTCAAGC ACTGATTGAT CTTAGGTTTT ACAATAGTGA    3480

TGTTACCCCA GGAACAATTT GGGGAAGGTC AGAATCTTGT AGCCTGTAGC TGCATGACTC    3540

CTAAACCATA ATTTCTTTTT TGTTTTTTTT TTTTTATTTT TGAGACAGGG TCTCACTCTG    3600
```

```
TCACCTAGGC TGGAGTGCAG TGGTGCAATC ACAGCTCACT GCAGCCCCTA GAGCGGCCGC    3660

CACCGCGGTG GAGCTCCAAT TCGCCCTATA GTGAGTCGTA TTACAATTCA CTGGCCGTCG    3720

TTTTACAACG TCGTGACTGG GAAAACCCTG GCGTTACCCA ACTTAATCGC CTTGCAGCAC    3780

ATCCCCCTTT CGCCAGCTGG CGTAATAGCG AAGAGGCCCG CACCGATCGC CCTTCCCAAC    3840

AGTTGCGCAG CCTGAATGGC GAATGGCGCG AAATTGTAAA CGTTAATATT TTGTTAAAAT    3900

TCGCGTTAAA TTTTTGTTAA ATCAGCTCAT TTTTTAACCA ATAGGCCGAA ATCGGCAAAA    3960

TCCCTTATAA ATCAAAAGAA TAGACCGAGA TAGGGTTGAG TGTTGTTCCA GTTTGGAACA    4020

AGAGTCCACT ATTAAAGAAC GTGGACTCCA ACGTCAAAGG GCGAAAAACC GTCTATCAGG    4080

GCGATGGCCC ACTACGTGAA CCATCACCCT AATCAAGTTT TTTGGGGTCG AGGTGCCGTA    4140

AAGCACTAAA TCGGAACCCT AAAGGGAGCC CCCGATTTAG AGCTTGACGG GGAAAGCCGG    4200

CGAACGTGGC GAGAAAGGAA GGGAAGAAAG CGAAAGGAGC GGGCGCTAGG GCGCTGGCAA    4260

GTGTAGCGGT CACGCTGCGC GTAACCACCA CACCCGCCGC GCTTAATGCG CCGCTACAGG    4320

GCGCGTCCCA GGTGGCACTT TTCGGGGAAA TGTGCGCGGA ACCCCTATTT GTTTATTTTT    4380

CTAAATACAT TCAAATATGT ATCCGCTCAT GAGACAATAA CCCTGATAAA TGCTTCAATA    4440

ATATTGAAAA AGGAAGAGTA TGAGTATTCA ACATTTCCGT GTCGCCCTTA TTCCCTTTTT    4500

TGCGGCATTT TGCCTTCCTG TTTTTGCTCA CCCAGAAACG CTGGTGAAAG TAAAAGATGC    4560

TGAAGATCAG TTGGGTGCAC GAGTGGGTTA CATCGAACTG GATCTCAACA GCGGTAAGAT    4620

CCTTGAGAGT TTTCGCCCCG AAGAACGTTT TCCAATGATG AGCACTTTTA AAGTTCTGCT    4680

ATGTGGCGCG GTATTATCCC GTATTGACGC CGGGCAAGAG CAACTCGGTC GCCGCATACA    4740

CTATTCTCAG AATGACTTGG TTGAGTACTC ACCAGTCACA GAAAAGCATC TTACGGATGG    4800

CATGACAGTA AGAGAATTAT GCAGTGCTGC CATAACCATG AGTGATAACA CTGCGGCCAA    4860

CTTACTTCTG ACAACGATCG GAGGACCGAA GGAGCTAACC GCTTTTTTGC ACAACATGGG    4920

GGATCATGTA ACTCGCCTTG ATCGTTGGGA ACCGGAGCTG AATGAAGCCA TACCAAACGA    4980

CGAGCGTGAC ACCACGATGC CTGTAGCAAT GGCAACAACG TTGCGCAAAC TATTAACTGG    5040

CGAACTACTT ACTCTAGCTT CCCGGCAACA ATTAATAGAC TGGATGGAGG CGGATAAAGT    5100

TGCAGGACCA CTTCTGCGCT CGGCCCTTCC GGCTGGCTGG TTTATTGCTG ATAAATCTGG    5160

AGCCGGTGAG CGTGGGTCTC GCGGTATCAT TGCAGCACTG GGGCCAGATG GTAAGCCCTC    5220

CCGTATCGTA GTTATCTACA CGACGGGGAG TCAGCAACT ATGGATGAAC GAAATAGACA    5280

GATCGCTGAG ATAGGTGCCT CACTGATTAA GCATTGGTAA CTGTCAGACC AAGTTTACTC    5340

ATATATACTT TAGATTGATT TAAAACTTCA TTTTTAATTT AAAAGGATCT AGGTGAAGAT    5400

CCTTTTTGAT AATCTCATGA CCAAAATCCC TTAACGTGAG TTTTCGTTCC ACTGAGCGTC    5460

AGACCCCGTA GAAAAGATCA AAGGATCTTC TTGAGATCCT TTTTTTCTGC GCGTAATCTG    5520

CTGCTTGCAA ACAAAAAAAC CACCGCTACC AGCGGTGGTT TGTTTGCCGG ATCAAGAGCT    5580

ACCAACTCTT TTTCCGAAGG TAACTGGCTT CAGCAGAGCG CAGATACCAA ATACTGTCCT    5640

TCTAGTGTAG CCGTAGTTAG GCCACCACTT CAAGAACTCT GTAGCACCGC CTACATACCT    5700

CGCTCTGCTA ATCCTGTTAC CAGTGGCTGC TGCCAGTGGC GATAAGTCGT GTCTTACCGG    5760

GTTGGACTCA AGACGATAGT TACCGGATAA GGCGCAGCGG TCGGGCTGAA CGGGGGGTTC    5820

GTGCACACAG CCCAGCTTGG AGCGAACGAC CTACACCGAA CTGAGATACC TACAGCGTGA    5880

GCTATGAGAA AGCGCCACGC TTCCCGAAGG GAGAAAGGCG GACAGGTATC CGGTAAGCGG    5940
```

```
CAGGGTCGGA ACAGGAGAGC GCACGAGGGA GCTTCCAGGG GGAAACGCCT GGTATCTTTA      6000

TAGTCCTGTC GGGTTTCGCC ACCTCTGACT TGAGCGTCGA TTTTTGTGAT GCTCGTCAGG      6060

GGGGCGGAGC CTATGGAAAA ACGCCAGCAA CGCGGCCTTT TTACGGTTCC TGGCCTTTTG      6120

CTGGCCTTTT GCTCACATGT TCTTTCCTGC GTTATCCCCT GATTCTGTGG ATAACCGTAT      6180

TACCGCCTTT GAGTGAGCTG ATACCGCTCG CCGCAGCCGA ACGACCGAGC GCAGCGAGTC      6240

AGTGAGCGAG GAAGCGGAAG AGCGCCCAAT ACGCAAACCG CCTCTCCCCG CGCGTTGGCC      6300

GATTCATTAA TGCAGCTGGC ACGACAGGTT TCCCGACTGG AAAGCGGGCA GTGAGCGCAA      6360

CGCAATTAAT GTGAGTTAGC TCACTCATTA GGCACCCCAG GCTTTACACT TTATGCTTCC      6420

GGCTCGTATG TTGTGTGGAA TTGTGAGCGG ATAACAATTT CACACAGGAA ACAGCTATGA      6480

CCATGATTAC GCCAAGCTCG GAATTAACCC TCACTAAAGG GAACAAAAGC TGCTGCAGGG      6540

TCCCTAACTG CCAAGCCCCA CAGTGTGCCC TGAGGCTGCC CCTTCCTTCT AGCGGCTGCC      6600

CCCACTCGGC TTTGCTTTCC CTAGTTTCAG TTACTTGCGT TCAGCCAAGG TCTGAAACTA      6660

GGTGCGCACA GAGCGGTAAG ACTGCGAGAG AAAGAGACCA GCTTTACAGG GGGTTTATCA      6720

CAGTGCACCC TGACAGTCGT CAGCCTCACA GGGGGTTTAT CACATTGCAC CCTGACAGTC      6780

GTCAGCCTCA CAGGGGGTTT ATCACAGTGC ACCCTTACAA TCATTCCATT TGATTCACAA      6840

TTTTTTTAGT CTCTACTGTG CCTAACTTGT AAGTTAAATT TGATCAGAGG TGTGTTCCCA      6900

GAGGGGAAAA CAGTATATAC AGGGTTCAGT ACTATCGCAT TTCAGGCCTC CACCTGGGTC      6960

TTGGAATGTG TCCCCCGAGG GGTGATGACT ACCTCAGTTG GATCTCCACA GGTCACAGTG      7020

ACACAAGATA ACCAAGACAC CTCCCAAGGC TACCACAATG GGCCGCCCTC CACGTGCACA      7080

TGGCCGGAGG AACTGCCATG TCGGAGGTGC AAGCACACCT GCGCATCAGA GTCCTTGGTG      7140

TGGAGGGAGG GACCAGCGCA GCTTCCAGCC ATCCACCTGA TGAACAGAAC CTAGGGAAAG      7200

CCCCAGTTCT ACTTACACCA GGAAAGGC                                        7228

(2) INFORMATION FOR SEQ ID NO:129:

(i) SEQUENCE CHARACTERISTICS:
        (A) LENGTH:  7228 BASE PAIRS
        (B) TYPE:  NUCLEIC ACID
        (C) STRANDEDNESS:  SINGLE
        (D) TOPOLOGY:  LINEAR (ix) SEQUENCE DESCRIPTION:  SEQ ID NO: 129:

TGGAAGGGCT AATTTGGTCC CAAAAAAGAC AAGAGATCCT TGATCTGTGG ATCTACCACA        60

CACAAGGCTA CTTCCCTGAT TGGCAGAACT ACACACCAGG GCCAGGGATC AGATATCCAC       120

TGACCTTTGG ATGGTGCTTC AAGTTAGTAC CAGTTGAACC AGAGCAAGTA GAAGAGGCCA       180

ATAAGGAGA GAAGAACAGC TTGTTACACC CTATGAGCCA GCATGGGATG GAGGACCCGG       240

AGGGAGAAGT ATTAGTGTGG AAGTTTGACA GCCTCCTAGC ATTTCGTCAC ATGGCCCGAG       300

AGCTGCATCC GGAGTACTAC AAAGACTGCT GACATCGAGC TTTCTACAAG GGACTTTCCG       360

CTGGGGACTT TCCAGGGAGG TGTGGCCTGG GCGGGACTGG GGAGTGGCGA GCCCTCAGAT       420

GCTACATATA AGCAGCTGCT TTTTGCCTGT ACTGGGTCTC TCTGGTTAGA CCAGATCTGA       480

GCCTGGGAGC TCTCTGGCTA ACTAGGGAAC CCACTGCTTA AGCCTCAATA AAGCTTGCCT       540

TGAGTGCTCA AAGTAGTGTG TGCCCGTCTG TTGTGTGACT CTGGTAACTA GAGATCCCTC       600

AGACCCTTTT AGTCAGTGTG GAAAATCTCT AGCAGTGGCG CCCGAACAGG GACTTGAAAG       660

CGAAAGTAAA GCCAGAGGAG ATCTCTCGAC GCAGGACTCG GCTTGCTGAA GCGCGCGTCG       720
```

-continued

| | |
|---|---|
| ACAGAGAG ATG GGT GCG AGA GCG TCA GTA TTA AGC GGG GGA GAA TTA GAT<br>     Met Gly Ala Arg Ala Ser Val Leu Ser Gly Gly Glu Leu Asp<br>     1        5         10 | 770 |
| CGA TGG GAA AAA ATT CGG TTA AGG CCA GGG GGA AAG AAG AAG TAC AAG<br>Arg Trp Glu Lys Ile Arg Leu Arg Pro Gly Gly Lys Lys Lys Tyr Lys<br>15       20        25        30 | 818 |
| CTA AAG CAC ATC GTA TGG GCA AGC AGG GAG CTA GAA CGA TTC GCA GTT<br>Leu Lys His Ile Val Trp Ala Ser Arg Glu Leu Glu Arg Phe Ala Val<br>       35        40        45 | 866 |
| AAT CCT GGC CTG TTA GAA ACA TCA GAA GGC TGT AGA CAA ATA CTG GGA<br>Asn Pro Gly Leu Leu Glu Thr Ser Glu Gly Cys Arg Gln Ile Leu Gly<br>     50        55        60 | 914 |
| CAG CTA CAA CCA TCC CTT CAG ACA GGA TCA GAG GAG CTT CGA TCA CTA<br>Gln Leu Gln Pro Ser Leu Gln Thr Gly Ser Glu Glu Leu Arg Ser Leu<br>    65        70        75 | 962 |
| TAC AAC ACA GTA GCA ACC CTC TAT TGT GTG CAC CAG CGG ATC GAG ATC<br>Tyr Asn Thr Val Ala Thr Leu Tyr Cys Val His Gln Arg Ile Glu Ile<br>80       85        90 | 1010 |
| AAG GAC ACC AAG GAA GCT TTA GAC AAG ATA GAG GAA GAG CAA AAC AAG<br>Lys Asp Thr Lys Glu Ala Leu Asp Lys Ile Glu Glu Glu Gln Asn Lys<br>95       100       105      110 | 1058 |
| TCC AAG AAG AAG GCC CAG CAG GCA GCA GCT GAC ACA GGA CAC AGC AAT<br>Ser Lys Lys Lys Ala Gln Gln Ala Ala Ala Asp Thr Gly His Ser Asn<br>111      115       120       125 | 1106 |
| CAG GTC AGC CAA AAT TAC CCT ATA GTG CAG AAC ATC CAG GGG CAA ATG<br>Gln Val Ser Gln Asn Tyr Pro Ile Val Gln Asn Ile Gln Gly Gln Met<br>       130       135      140 | 1154 |
| GTA CAT CAG GCC ATA TCA CCT AGA ACT TTA AAT GCA TGG GTA AAA GTA<br>Val His Gln Ala Ile Ser Pro Arg Thr Leu Asn Ala Trp Val Lys Val<br>     145       150       155 | 1202 |
| GTA GAA GAG AAG GCT TTC AGC CCA GAA GTG ATA CCC ATG TTT TCA GCA<br>Val Glu Glu Lys Ala Phe Ser Pro Glu Val Ile Pro Met Phe Ser Ala<br>    160        165      170 | 1250 |
| TTA TCA GAA GGA GCC ACC CCA CAG GAC CTG AAC ACG ATG TTG AAC ACC<br>Leu Ser Glu Gly Ala Thr Pro Gln Asp Leu Asn Thr Met Leu Asn Thr<br>175      180       185       190 | 1298 |
| GTG GGG GGA CAT CAA GCA GCC ATG CAA ATG TTA AAA GAG ACC ATC AAT<br>Val Gly Gly His Gln Ala Ala Met Gln Met Leu Lys Glu Thr Ile Asn<br>       195       200      205 | 1346 |
| GAG GAA GCT GCA GAA TGG GAT AGA GTG CAT CCA GTG CAT GCA GGG CCT<br>Glu Glu Ala Ala Glu Trp Asp Arg Val His Pro Val His Ala Gly Pro<br>     210       215       220 | 1394 |
| ATT GCA CCA GGC CAG ATG AGA GAA CCA AGG GGA AGT GAC ATA GCA GGA<br>Ile Ala Pro Gly Gln Met Arg Glu Pro Arg Gly Ser Asp Ile Ala Gly<br>    225        230      235 | 1442 |
| ACT ACT AGT ACC CTT CAG GAA CAA ATA GGA TGG ATG ACA AAT AAT CCA<br>Thr Thr Ser Thr Leu Gln Glu Gln Ile Gly Trp Met Thr Asn Asn Pro<br>   240        245       250 | 1490 |
| CCT ATC CCA GTA GGA GAG ATC TAC AAG AGG TGG ATA ATC CTG GGA TTG<br>Pro Ile Pro Val Gly Glu Ile Tyr Lys Arg Trp Ile Ile Leu Gly Leu<br>255      260       265       270 | 1538 |
| AAC AAG ATC GTG AGG ATG TAT AGC CCT ACC AGC ATT CTG GAC ATA AGA<br>Asn Lys Ile Val Arg Met Tyr Ser Pro Thr Ser Ile Leu Asp Ile Arg<br>       275       280      285 | 1586 |
| CAA GGA CCA AAG GAA CCC TTT AGA GAC TAT GTA GAC CGG TTC TAT AAA<br>Gln Gly Pro Lys Glu Pro Phe Arg Asp Tyr Val Asp Arg Phe Tyr Lys<br>     290       295       300 | 1634 |
| ACT CTA AGA GCT GAG CAA GCT TCA CAG GAG GTA AAA AAT TGG ATG ACA<br>Thr Leu Arg Ala Glu Gln Ala Ser Gln Glu Val Lys Asn Trp Met Thr<br>    305        310       315 | 1682 |

| | |
|---|---|
| GAA ACC TTG TTG GTC CAA AAT GCG AAC CCA GAT TGT AAG ACC ATC CTG<br>Glu Thr Leu Leu Val Gln Asn Ala Asn Pro Asp Cys Lys Thr Ile Leu<br>320                              325                            330 | 1730 |
| AAG GCT CTC GGC CCA GCG GCT ACA CTA GAA GAA ATG ATG ACA GCA TGT<br>Lys Ala Leu Gly Pro Ala Ala Thr Leu Glu Glu Met Met Thr Ala Cys<br>335                         340                        345                            350 | 1778 |
| CAG GGA GTA GGA GGA CCC GGC CAT AAG GCA AGA GTT TTG TAG<br>Gln Gly Val Gly Gly Pro Gly His Lys Ala Arg Val Leu<br>                        355                            360 | 1820 |
| GGATCCACTA GTTCTAGACT CGAGGGGGGG CCCGGTACCT TTAAGACCAA TGACTTACAA | 1880 |
| GGCAGCTGTA GATCTTAGCC ACTTTTTAAA AGAAAAGGGG GGACTGGAAG GGCTAATTCA | 1940 |
| CTCCCAAAGA AGACAAGATA TCCTTGATCT GTGGATCTAC CACACACAAG GCTACTTCCC | 2000 |
| TGATTGGCAG AACTACACAC CAGGGCCAGG GGTCAGATAT CCACTGACCT TTGGATGGTG | 2060 |
| CTACAAGCTA GTACCAGTTG AGCCAGATAA GGTAGAAGAG GCCAATAAAG GAGAGAACAC | 2120 |
| CAGCTTGTTA CACCCTGTGA GCCTGCATGG AATGGATGAC CCTGAGAGAG AAGTGTTAGA | 2180 |
| GTGGAGGTTT GACAGCCGCC TAGCATTTCA TCACGTGGCC CGAGAGCTGC ATCCGGAGTA | 2240 |
| CTTCAAGAAC TGCTGACATC GAGCTTGCTA CAAGGGACTT TCCGCTGGGG ACTTTCCAGG | 2300 |
| GAGGCGTGGC CTGGGCGGGA CTGGGGAGTG GCGAGCCCTC AGATGCTGCA TATAAGCAGC | 2360 |
| TGCTTTTTGC CTGTACTGGG TCTCTCTGGT TAGACCAGAT CTGAGCCTGG GAGCTCTCTG | 2420 |
| GCTAACTAGG GAACCCACTG CTTAAGCCTC AATAAAGCTT GCCTTGAGTG CTTCAAGTAG | 2480 |
| TGTGTGCCCG TCTGTTGTGT GACTCTGGTA ACTAGAGATC CCTCAGACCC TTTTAGTCAG | 2540 |
| TGTGGAAAAT CTCTAGCACC CCCCAGGAGG TAGAGGTTGC AGTGAGCCAA GATCGCGCCA | 2600 |
| CTGCATTCCA GCCTGGGCAA GAAAACAAGA CTGTCTAAAA TAATAATAAT AAGTTAAGGG | 2660 |
| TATTAAATAT ATTTATACAT GGAGGTCATA AAAATATATA TATTTGGGCT GGGCGCAGTG | 2720 |
| GCTCACACCT GCGCCCGGCC CTTTGGGAGG CCGAGGCAGG TGGATCACCT GAGTTTGGGA | 2780 |
| GTTCCAGACC AGCCTGACCA ACATGGAGAA ACCCCTTCTC TGTGTATTTT TAGTAGATTT | 2840 |
| TATTTTATGT GTATTTTATT CACAGGTATT CTGGAAAAC TGAAACTGTT TTTCCTCTAC | 2900 |
| TCTGATACCA AAGAATCAT CAGCACAGAG GAAGACTTCT GTGATCAAAT GTGGTGGGAG | 2960 |
| AGGGAGGTTT TCACCAGCAC ATGAGCAGTC AGTTCTGCCG CAGACTCGGC GGGTGTCCTT | 3020 |
| CGGTTCAGTT CCAACACCGC CTGCCTGGAG AGAGGTCAGA CCACAGGGTG AGGGCTCAGT | 3080 |
| CCCCAAGACA TAAACACCCA AGACATAAAC ACCCAACAGG TCCACCCCGC CTGCTGCCCA | 3140 |
| GGCAGAGCCG ATTCACCAAG ACGGGAATTA GGATAGAGAA AGAGTAAGTC ACACAGAGCC | 3200 |
| GGCTGTGCGG GAGAACGGAG TTCTATTATG ACTCAAATCA GTCTCCCCAA GCATTCGGGG | 3260 |
| ATCAGAGTTT TTAAGGATAA CTTAGTGTGT AGGGGGCCAG TGAGTTGGAG ATGAAAGCGT | 3320 |
| AGGGAGTCGA AGGTGTCCTT TTGCGCCGAG TCAGTTCCTG GGTGGGGGCC ACAAGATCGG | 3380 |
| ATGAGCCAGT TTATCAATCC GGGGGTGCCA GCTGATCCAT GGAGTGCAGG GTCTGCAAAA | 3440 |
| TATCTCAAGC ACTGATTGAT CTTAGGTTTT ACAATAGTGA TGTTACCCCA GGAACAATTT | 3500 |
| GGGGAAGGTC AGAATCTTGT AGCCTGTAGC TGCATGACTC CTAAACCATA ATTTCTTTTT | 3560 |
| TGTTTTTTTT TTTTTATTTT TGAGACAGGG TCTCACTCTG TCACCTAGGC TGGAGTGCAG | 3620 |
| TGGTGCAATC ACAGCTCACT GCAGCCCCTA GAGCGGCCGC CACCGCGGTG GAGCTCCAAT | 3680 |
| TCGCCCTATA GTGAGTCGTA TTACAATTCA CTGGCCGTCG TTTTACAACG TCGTGACTGG | 3740 |
| GAAAACCCTG GCGTTACCCA ACTTAATCGC CTTGCAGCAC ATCCCCCTTT CGCCAGCTGG | 3800 |

-continued

```
CGTAATAGCG AAGAGGCCCG CACCGATCGC CCTTCCCAAC AGTTGCGCAG CCTGAATGGC    3860

GAATGGCGCG AAATTGTAAA CGTTAATATT TTGTTAAAAT TCGCGTTAAA TTTTTGTTAA    3920

ATCAGCTCAT TTTTTAACCA ATAGGCCGAA ATCGGCAAAA TCCCTTATAA ATCAAAAGAA    3980

TAGACCGAGA TAGGGTTGAG TGTTGTTCCA GTTTGGAACA AGAGTCCACT ATTAAAGAAC    4040

GTGGACTCCA ACGTCAAAGG GCGAAAAACC GTCTATCAGG GCGATGGCCC ACTACGTGAA    4100

CCATCACCCT AATCAAGTTT TTTGGGGTCG AGGTGCCGTA AAGCACTAAA TCGGAACCCT    4160

AAAGGGAGCC CCCGATTTAG AGCTTGACGG GGAAAGCCGG CGAACGTGGC GAGAAAGGAA    4220

GGGAAGAAAG CGAAAGGAGC GGGCGCTAGG GCGCTGGCAA GTGTAGCGGT CACGCTGCGC    4280

GTAACCACCA CACCCGCCGC GCTTAATGCG CCGCTACAGG GCGCGTCCCA GGTGGCACTT    4340

TTCGGGGAAA TGTGCGCGGA ACCCCTATTT GTTTATTTTT CTAAATACAT TCAAATATGT    4400

ATCCGCTCAT GAGACAATAA CCCTGATAAA TGCTTCAATA ATATTGAAAA AGGAAGAGTA    4460

TGAGTATTCA ACATTTCCGT GTCGCCCTTA TTCCCTTTTT TGCGGCATTT TGCCTTCCTG    4520

TTTTTGCTCA CCCAGAAACG CTGGTGAAAG TAAAAGATGC TGAAGATCAG TTGGGTGCAC    4580

GAGTGGGTTA CATCGAACTG GATCTCAACA GCGGTAAGAT CCTTGAGAGT TTTCGCCCCG    4640

AAGAACGTTT TCCAATGATG AGCACTTTTA AAGTTCTGCT ATGTGGCGCG GTATTATCCC    4700

GTATTGACGC CGGGCAAGAG CAACTCGGTC GCCGCATACA CTATTCTCAG AATGACTTGG    4760

TTGAGTACTC ACCAGTCACA GAAAAGCATC TTACGGATGG CATGACAGTA AGAGAATTAT    4820

GCAGTGCTGC CATAACCATG AGTGATAACA CTGCGGCCAA CTTACTTCTG ACAACGATCG    4880

GAGGACCGAA GGAGCTAACC GCTTTTTTGC ACAACATGGG GGATCATGTA ACTCGCCTTG    4940

ATCGTTGGGA ACCGGAGCTG AATGAAGCCA TACCAAACGA CGAGCGTGAC ACCACGATGC    5000

CTGTAGCAAT GGCAACAACG TTGCGCAAAC TATTAACTGG CGAACTACTT ACTCTAGCTT    5060

CCCGGCAACA ATTAATAGAC TGGATGGAGG CGGATAAAGT TGCAGGACCA CTTCTGCGCT    5120

CGGCCCTTCC GGCTGGCTGG TTTATTGCTG ATAAATCTGG AGCCGGTGAG CGTGGGTCTC    5180

GCGGTATCAT TGCAGCACTG GGGCCAGATG GTAAGCCCTC CCGTATCGTA GTTATCTACA    5240

CGACGGGGAG TCAGGCAACT ATGGATGAAC GAAATAGACA GATCGCTGAG ATAGGTGCCT    5300

CACTGATTAA GCATTGGTAA CTGTCAGACC AAGTTTACTC ATATATACTT TAGATTGATT    5360

TAAAACTTCA TTTTTAATTT AAAAGGATCT AGGTGAAGAT CCTTTTTGAT AATCTCATGA    5420

CCAAAATCCC TTAACGTGAG TTTTCGTTCC ACTGAGCGTC AGACCCCGTA GAAAAGATCA    5480

AAGGATCTTC TTGAGATCCT TTTTTTCTGC GCGTAATCTG CTGCTTGCAA ACAAAAAAAC    5540

CACCGCTACC AGCGGTGGTT TGTTTGCCGG ATCAAGAGCT ACCAACTCTT TTTCCGAAGG    5600

TAACTGGCTT CAGCAGAGCG CAGATACCAA ATACTGTCCT TCTAGTGTAG CCGTAGTTAG    5660

GCCACCACTT CAAGAACTCT GTAGCACCGC CTACATACCT CGCTCTGCTA ATCCTGTTAC    5720

CAGTGGCTGC TGCCAGTGGC GATAAGTCGT GTCTTACCGG GTTGGACTCA AGACGATAGT    5780

TACCGGATAA GGCGCAGCGG TCGGGCTGAA CGGGGGGTTC GTGCACACAG CCCAGCTTGG    5840

AGCGAACGAC CTACACCGAA CTGAGATACC TACAGCGTGA GCTATGAGAA AGCGCCACGC    5900

TTCCCGAAGG GAGAAAGGCG GACAGGTATC CGGTAAGCGG CAGGGTCGGA ACAGGAGAGC    5960

GCACGAGGGA GCTTCCAGGG GGAAACGCCT GGTATCTTTA TAGTCCTGTC GGGTTTCGCC    6020

ACCTCTGACT TGAGCGTCGA TTTTTGTGAT GCTCGTCAGG GGGCGGAGC CTATGGAAAA    6080

ACGCCAGCAA CGCGGCCTTT TTACGGTTCC TGGCCTTTTG CTGGCCTTTT GCTCACATGT    6140

TCTTTCCTGC GTTATCCCCT GATTCTGTGG ATAACCGTAT TACCGCCTTT GAGTGAGCTG    6200
```

-continued

```
ATACCGCTCG CCGCAGCCGA ACGACCGAGC GCAGCGAGTC AGTGAGCGAG GAAGCGGAAG    6260

AGCGCCCAAT ACGCAAACCG CCTCTCCCCG CGCGTTGGCC GATTCATTAA TGCAGCTGGC    6320

ACGACAGGTT TCCCGACTGG AAAGCGGGCA GTGAGCGCAA CGCAATTAAT GTGAGTTAGC    6380

TCACTCATTA GGCACCCCAG GCTTTACACT TTATGCTTCC GGCTCGTATG TTGTGTGGAA    6440

TTGTGAGCGG ATAACAATTT CACACAGGAA ACAGCTATGA CCATGATTAC GCCAAGCTCG    6500

GAATTAACCC TCACTAAAGG GAACAAAAGC TGCTGCAGGG TCCCTAACTG CCAAGCCCCA    6560

CAGTGTGCCC TGAGGCTGCC CCTTCCTTCT AGCGGCTGCC CCCACTCGGC TTTGCTTTCC    6620

CTAGTTTCAG TTACTTGCGT TCAGCCAAGG TCTGAAACTA GGTGCGCACA GAGCGGTAAG    6680

ACTGCGAGAG AAAGAGACCA GCTTTACAGG GGGTTTATCA CAGTGCACCC TGACAGTCGT    6740

CAGCCTCACA GGGGGTTTAT CACATTGCAC CCTGACAGTC GTCAGCCTCA CAGGGGGTTT    6800

ATCACAGTGC ACCCTTACAA TCATTCCATT TGATTCACAA TTTTTTTAGT CTCTACTGTG    6860

CCTAACTTGT AAGTTAAATT TGATCAGAGG TGTGTTCCCA GAGGGGAAAA CAGTATATAC    6920

AGGGTTCAGT ACTATCGCAT TTCAGGCCTC CACCTGGGTC TTGGAATGTG TCCCCCGAGG    6980

GGTGATGACT ACCTCAGTTG GATCTCCACA GGTCACAGTG ACACAAGATA ACCAAGACAC    7040

CTCCCAAGGC TACCACAATG GGCCGCCCTC CACGTGCACA TGGCCGGAGG AACTGCCATG    7100

TCGGAGGTGC AAGCACACCT GCGCATCAGA GTCCTTGGTG TGGAGGGAGG GACCAGCGCA    7160

GCTTCCAGCC ATCCACCTGA TGAACAGAAC CTAGGGAAAG CCCCAGTTCT ACTTACACCA    7220

GGAAAGGC                                                             7228
```

(2) INFORMATION FOR SEQ ID NO: 130:

(i) SEQUENCE CHARACTERISTICS:
        (A) LENGTH: 363 AMINO ACIDS
        (B) TYPE: AMINO ACID
        (C) TOPOLOGY: LINEAR (ii) MOLECULE TYPE: PROTEIN (xi) SEQUENCE DESCRIPTION: SEQ ID NO: 130:

```
Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly His Ser Asn Gln Val
        115                 120                 125

Ser Gln Asn Tyr Pro Ile Val Gln Asn Ile Gln Gly Gln Met Val His
    130                 135                 140

Gln Ala Ile Ser Pro Arg Thr Leu Asn Ala Trp Val Lys Val Val Glu
145                 150                 155                 160
```

-continued

```
Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Val His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr Asn Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Ala Ala Thr Leu Glu Glu Met Met Thr Ala Cys Gln Gly
            340                 345                 350

Val Gly Gly Pro Gly His Lys Ala Arg Val Leu
        355                 360
```